US008969066B2

(12) United States Patent
Mendez et al.

(10) Patent No.: US 8,969,066 B2
(45) Date of Patent: Mar. 3, 2015

(54) INDUCTION OF FLOCCULATION IN PHOTOSYNTHETIC ORGANISMS

(75) Inventors: Michael Mendez, San Diego, CA (US); Craig Behnke, San Diego, CA (US); Yan Poon, San Diego, CA (US); Philip Lee, San Diego, CA (US)

(73) Assignee: Sapphire Energy, Inc., San Diego, CA (US)

( * ) Notice: Subject to any disclaimer, the term of this patent is extended or adjusted under 35 U.S.C. 154(b) by 782 days.

(21) Appl. No.: 13/001,027

(22) PCT Filed: Jun. 26, 2009

(86) PCT No.: PCT/US2009/048929
§ 371 (c)(1),
(2), (4) Date: Mar. 15, 2011

(87) PCT Pub. No.: WO2009/158658
PCT Pub. Date: Dec. 30, 2009

(65) Prior Publication Data
US 2011/0159595 A1 Jun. 30, 2011

Related U.S. Application Data

(60) Provisional application No. 61/076,430, filed on Jun. 27, 2008.

(51) Int. Cl.
| | |
|---|---|
| C12N 15/87 | (2006.01) |
| C12N 1/02 | (2006.01) |
| C12N 1/13 | (2006.01) |
| C12P 21/00 | (2006.01) |
| C12P 19/00 | (2006.01) |
| B03D 3/06 | (2006.01) |
| C12N 15/62 | (2006.01) |
| C12N 1/12 | (2006.01) |
| C07K 14/47 | (2006.01) |
| C07K 16/16 | (2006.01) |

(52) U.S. Cl.
CPC .............. *C12N 1/12* (2013.01); *C07K 14/4726* (2013.01); *C07K 16/16* (2013.01); *C12N 1/02* (2013.01)
USPC ........ 435/257.2; 800/278; 800/288; 800/284; 435/71.1; 435/69.8; 435/468; 435/261; 209/5; 530/388.5; 530/395; 530/396

(58) Field of Classification Search
None
See application file for complete search history.

(56) References Cited

U.S. PATENT DOCUMENTS 4,870,015 A 9/1989 Hoffman
5,776,689 A 7/1998 Karin et al.

2003/0211089 A1* 11/2003 Sayre et al. ................ 424/93.21
2009/0005264 A1* 1/2009 Rakestraw et al. ............. 506/14

FOREIGN PATENT DOCUMENTS

CN 1827769 A 9/2006
WO WO 01/98335 A2 12/2001

OTHER PUBLICATIONS

Slifkin et al (Clin. Microbiol. Rev., 3(3), 1990).*
Harwood et al (Current Opinion in Cell Biology, 16, p. 470-476, 2004; Harwood).*
Grima et al (Biotechnology Advances, 20, p. 491-515, 2003; Grima).*
Nair et al (J. Bateriol, 183(5), p. 1740-1747, 2001; Nair).*
Sengupta et al (Indian Journal of Experimental Biology, 35, pp. 103-110, 1997; Sengupta).*
de la Noue et al (Journal of Applied Phycology, 4, pp. 247-254, 1992).*
Vioque (Advances in Experimental Medicine and Biology, 616, pp. 12-22, 2007).*
Oh et al (Biotechnology Letters, 23, pp. 1229-1234, 2001).*
Vandamme et al (Trends in Biotechnology, 31(4), pp. 233-239, 2013).*
Lee et al., Microbial flocculation, a potentially low-cost harvesting technique for marine microalgae for the production of biodiesel. J. Appl. Phycol., 2009, vol. 21, pp. 559-567.
Homan et al., "Monoclonal antibodies to surface glycoconjugates in *Chlamydomonas eugametos* recognize strain-specific O-methyl sugars." Planta, 1987, vol. 170, pp. 328-335.
Javadekar et al., "A mannose-binding protein from the cell surface of flocculent *Saccharomyces cerevisiae* (NCIM 3528): its role in flocculation." Yeast, 2000, vol. 16, pp. 99-110.
Matsuda et al., "Cell walls of algae in the volvocales: Their sensitivity to a cell wall lytic enzyme and labeling with an anti-cell wall glycopeptide of *Chlamydomonas reinhardtii*." Bot. Mag. Tokyo, 1987, vol. 100. pp. 373-384.
Mayfield, et al. Expression and assembly of a fully active antibody in algae. Jan. 21, 2003 100(2)438-442.
Nikitina et al., "The role of cell-surface lectins in the aggregation of azospirilla." Microbiology, 2001, vol. 70, No. 4, pp. 408-412.
Strauss et al., "Mitochondrial associated yeast flocculation—the effect of acetylsalicylic acid." Journal of the Institute of Brewing, 2007, vol. 113, pp. 42-47.
Touhami et al., "Aggregation of yeast cells: direct measurement of discrete lectin-carbohydrate interactions." Microbiology, 2003, vol. 149, pp. 2873-2878.
Wheeler et al., "Genome Analyis of the Unicellular Green Alga *Chlamydomonas reinhardtii* Indicates an Acient Evolutionary Origin of Key Pattern Recognition and Cell-Signaling Protein Families." Genetics, 2008, vol. 179, pp. 193-197.
Bender et al. Characterization of metal-binding bioflocculants producted by the cyanobacterial component of mixed microbual mats. Applied and Environmental Microbiology. 1994. 60(7):2311-2315.

(Continued)

*Primary Examiner* — David T Fox
*Assistant Examiner* — Stephen Uyeno
(74) *Attorney, Agent, or Firm* — James E. Butler; David R. Marsh; Arnold & Porter LLP

(57) ABSTRACT

The present invention provides compositions and methods for producing flocculation moieties in photosynthetic organisms. The photosynthetic organisms are genetically modified to effect production, secretion, or both, of the flocculation moieties. Also provided are methods of flocculating organisms.

10 Claims, 23 Drawing Sheets

(56) References Cited

OTHER PUBLICATIONS

Bo et al., "Development and Application in Yeast Cell Surface Display System," Industrial Microbiology, 2007, vol. 37, No. 6, pp. 53-58.

Nishihara et al., Possible mechanism of co-flocculation between non-flocculent yeasts. Journal of the Institute of Brewing. 2000. 106(1):7-10.

Oh et al. Havesting of *Chlorrella vulgaris* using a bioflocculant from *Paenibacillas* sp. AM49. Biotechnology Letters. 2001. 23:1229-1234.

Schenk et al. Second generation biofuels: High-efficiency microalgae for biodiesel production Bioenerg. Res. 2008. 1:20-43.

European Search Report completed on Jul. 4, 2013, in European Patent Application No. 09771189.9 (4 pages).

Apt et al. In vivo characterization of diatom multipartite plastid targeting signals. Journal of Cell Science (2002) 115:4061-1069.

Liao et al. Antibiotic activity of lectins from marine algae against marine vibrios. J. Ind. Microbiol Biotechnol. (2003) 30:433-439.

Mayfield et al., Expression of human antibodies in eukaryotic microalgae. Vaccine 23 (2005) 1828-1832.

Wang et al. Cell Wall proteomics of the green alga *Haematococcus pluvialis* (Chlorophyceae). Proteomics (2004) 4:692-708.

\* cited by examiner

INDUCTION OF FLOCCULATION IN PHOTOSYNTHETIC ORGANISMS

CROSS REFERENCE TO RELATED APPLICATIONS

This application is a national phase filing of International Patent Application PCT/US2009/048929 entitled INDUCTION OF FLOCCULATION IN PHOTOSYNTHETIC ORGANISMS filed Jun. 26, 2009 which claims the benefit of U.S. Provisional Application No. 61/076,430, entitled INDUCTION OF FLOCCULATION IN PHOTOSYNTHETIC ORGANISMS, filed Jun. 27, 2008, each of which are incorporated herein by reference in their entirety for all purposes.

BACKGROUND

Algae are unicellular organisms, producing oxygen by photosynthesis. One group, the microalgae, are useful for biotechnology applications for many reasons, including their high growth rate and tolerance to varying environmental conditions. The use of microalgae in a variety of industrial processes for commercially important products is known and/or has been suggested. For example, microalgae have uses in the production of nutritional supplements, pharmaceuticals, natural dyes, a food source for fish and crustaceans, biological control of agricultural pests, production of oxygen and removal of nitrogen, phosphorus and toxic substances in sewage treatment, and pollution controls, such as biodegradation of plastics or uptake of carbon dioxide.

Microalgae, like other organisms, contain lipids and fatty acids as membrane components, storage products, metabolites and sources of energy. Some algal strains, diatoms, and cyanobacteria have been found to contain proportionally high levels of lipids (over 30%). Microalgal strains with high oil or lipid content are of great interest in the search for a sustainable feedstock for the production of biofuels.

Some wild-type algae are suitable for use in various industrial applications. However, it is recognized that by modification of algae to improve particular characteristics useful for the aforementioned applications, the relevant processes are more likely to be commercially viable. To this end, algal strains can be developed which have improved characteristics over wild-type strains. Such developments have been made by traditional techniques of screening and mutation and selection. Further, recombinant DNA technologies have been widely suggested for algae. Such approaches may increase the economic validity of production of commercially valuable products.

For the production of some commercial products of interest, organisms producing the products may be grown in liquid environments. It is sometimes beneficial to remove the organisms from the liquid environments. One method of removing organisms is to flocculate or aggregate the organisms to facilitate removal. Flocculants or flocculating agents promote flocculation by causing colloids and other suspended particles (e.g., cells) in liquids to aggregate, forming a floe. Flocculants are used in water treatment processes to improve the sedimentation of small particles. For example, a flocculant may be used in swimming pool or drinking water filtration to aid removal of microscopic particles which would otherwise cause the water to be cloudy and which would be difficult to remove by filtration alone.

Many flocculants are multivalent cations such as aluminium, iron, calcium or magnesium. These positively charged molecules interact with negatively charged particles and molecules to reduce the barriers to aggregation. In addition, many of these chemicals, under appropriate pH and other conditions such, as temperature and salinity, react with water to form insoluble hydroxides which, upon, precipitating, link together to form long chains or meshes, physically trapping small particles into the larger floe.

Flocculation of microalgae using chemical flocculants is known. Long-chain polymer flocculants, such as modified polyacrylamides, are manufactured and sold by the flocculant producing business. These can be supplied in dry or liquid form for use in the flocculation process. The most common liquid polyacrylamide, for example, is supplied as an emulsion with 10-40% actives and the rest is a carrier fluid, surfactants and latex.

Use of chemical flocculants, however, has multiple drawbacks. For instance, use in water treatment and other processes require subsequent removal of flocculants. The addition and removal of flocculants adds to the cost of commercial production of a product of interest, thus decreasing the economic feasibility of production.

SUMMARY

One aspect of the present disclosure provides for vectors comprising a nucleic acid encoding a flocculating moiety and a regulatory element linked to express the flocculating moiety in the nucleus of a photosynthetic organism. The flocculating moieties employed in this invention may comprise carbohydrate binding proteins, antibodies binding to a cell surface antigen of *C. reinhardtii, D. salina, D. tertiolecta,* or *H. pluvialis,* lectin, FhuA protein, pb5 protein, or other proteins that form a tight protein-protein pairing where the pairing leads to flocculation of microalgae. The regulatory elements utilized in the vectors may comprise a constitutive promoter, light-inducible promoter, quorum-sensitive promoter, temperature-sensitive promoter, or nitrogen-starvation, responsive promoter. The vectors disclosed herein may also contain nucleic acids capable of targeting the flocculation moiety to the cell surface and to anchor a portion of the flocculation moiety to be tightly bound on the cell surface. The vectors are utilized to transform non-vascular photosynthetic organisms, such as microalgae, for flocculation. In certain cases, the anchoring moiety can be optional as secreting the flocculation moiety into the culture, depending on the property of a flocculation moiety, is preferable method for flocculation.

Another aspect provides methods of flocculation utilizing non-vascular photosynthetic organisms. Examples of non-vascular photosynthetic organisms are *C. reinhardtii, D. salina, D. tertiolecta, S. dimorphus,* or *H. pluvialis.* The flocculation methods may comprise creating two distinctly different photosynthetic organisms by transforming with different flocculation moieties and causing flocculation by allowing the two flocculation moieties to interact each other. Examples of flocculation moieties comprise protein-protein interaction between FhuA and pb5, interactions between mating-type specific agglutinins, an antibody-antigen pairing, and other proteins capable of recognizing each other as a pair and form a stable protein-protein complex. Examples of methods for the induction of flocculation of non-vascular photosynthetic organisms are changing light condition, culture density, culture temperature, or nutrient availability; adding lectin, protein, heavy metal, cationic or chemical flocculant in the culture; or attaching the aforementioned flocculation agents to a solid support.

Another aspect provides methods to recycle the culture liquid from a liquid environment. Non-vascular photosynthetic organisms can be cultured in a media with defined media known in the art, such as min-70, M-medium, or TAP medium. After flocculation, it is often possible and economically beneficial to recycle the liquid portion of the culture. Disclosed herein are methods to enable the recycling of the liquid comprising growing microorganisms encoding a flocculation moiety; contacting the organism with flocculating moiety and thereby flocculating the organism; and removing the aggregated microorganism from the liquid environment.

One particular aspect provides a method for flocculating a non-vascular photosynthetic organism comprising expressing an exogenous nucleic acid encoding a first flocculation moiety on the external surface of a non-vascular photosynthetic organism and contacting the organism with a second flocculation moiety. The organism can be a member of the genus *Chlamydomonas, Dunaliella, Scenedesmus* or *Hematococcus*, for example *C. reinhardtii, D. salina, D. tertiolecta, S. dimorphus* or *H. pluvialis*, although members of other genera may be used. The first flocculation moiety can be a carbohydrate binding protein such as a lectin and in particular c-type lectin. Other non-limiting examples of carbohydrate binding proteins include DC-SIGN, dectin-1, dectin-2, HECL, langerin, layilin, mincle, MMGL, E-selectin, P-selectin, L-selectin, DEC-205, Endo 180, mannose receptor, phospholipase A2 receptor, sialoadhesin (siglec-1), siglec-2, siglec-3, siglec-4, siglec-5, siglec-6, siglec-7, siglec-8, siglec-9, siglec-10, siglec-11, and galectins. In other embodiments, the first flocculation moiety may be a univalent, monvalent or polyvalent antibody, for example an scFv antibody, that binds to an antigen on the surface of an organism of interest. Examples of such organisms include members of the genus *Chlamydomonas, Dunaliella, Scenedesmus* or *Hematococcus*, such as *C. reinhardtii, D. salina, D. tertiolecta, S. dimorphus* or *H. pluvialis*. Some embodiments may also include the use of a second flocculation moiety. The second flocculation moiety may be on the surface of a solid support or on the surface of a second organism, which may or may not be a non-vascular photosynthetic organism. When the second flocculation moiety is expressed on the surface of a second organism, the second flocculation moiety may be naturally occurring or may be the result of expression of an exogenous nucleotide sequence. In some embodiments, the first and second organisms are the same species, while in other embodiments, the first and second organisms are of different strains, different genera or different kingdoms. For example, in one embodiment the first and second organism are both algae while in another embodiment one organism is an alga while the other is a bacterium or yeast. When the second flocculation moiety is on the surface of a second organism or solid support, the method further comprises combining the first organism with the second organism, with the solid support, or both.

Another aspect provides a non-vascular photosynthetic organism comprising an exogenous protein on the organism's external cell surface, such as a cell membrane or cell wall; the exogenous protein comprising one member of a binding pair. The exogenous protein can be an antibody such as a single chain variable fragment (scFv) antibody or a carbohydrate binding protein such as a lectin, for example a c-type lectin. In other embodiments the exogenous protein is an antigen which is the target of an antibody, and in one embodiment an antibody specific to that antigen. In some embodiments the exogenous protein is a fusion or chimeric protein in which part of the protein serves to anchor the protein to the cell surface. The non-vascular photosynthetic organism may be an alga, for example a green alga, more particularly a member of the genus *Chlamydomonas, Dunaliella, Scenedesmus* or *Hematococcus* and more particularly one of *C. reinhardtii, D. salina, D. tertiolecta, S. dimorphus* or *H. pluvialis*. In one embodiment, the non-vascular photosynthetic organism is a halophile such as *D. salina* or *D. tertiolecta*. In still other embodiments, the carbohydrate binding protein is at least one of DC-SIGN, dectin-1, dectin-2, HECL, langerin, layilin, mincle, E-selectin, P-selectin, L-selectin, DEC-205, Endo 180, mannose receptor, phospholipase A2 receptor, sialoadhesin (siglec-1), siglec-2, siglec-3, siglec-4, siglec-5, siglec-6, siglec-7, siglec-8, siglec-9, siglec-10, siglec-11, or galectins.

Yet another aspect provides a flocculation method comprising transforming a first non-vascular photosynthetic organism with a nucleic acid encoding a first flocculation moiety, transforming a second organism, which may or may not be a non-vascular photosynthetic organism, with a nucleic acid encoding a second flocculation moiety or a protein necessary for the production of a second flocculation moiety that interacts with the first flocculation moiety, expressing the first and second flocculation moieties and contacting the two moieties such that flocculation occurs. The two organisms may be of the same or different genera, the same or different species or the same or different kingdoms. For example, the organisms may be the same species of algae, different species of algae, or an alga and a bacterium or yeast. The first organism, the second organism or both can be members of the genus *Chlamydomonas, Dunaliella, Scenedesmus* or *Hematococcus* such that one or both of the organisms can be *C. reinhardtii, D. salina, D. tertiolecta, S. dimorphus* or *H. pluvialis*. The first or second flocculation moieties can be antibodies, carbohydrate binding proteins or mating-type specific agglutinins.

Still another aspect provides a vector comprising an isolated nucleic acid encoding a flocculation moiety, a regulatory element for expressing the flocculation moiety in the photosynthetic organism, for example in the nucleus, and a targeting element that allows the flocculating moiety to be directed to the surface of the organism or be secreted by the organism. The flocculation moiety can be an antibody or any of the carbohydrate binding proteins described herein. Specific examples of flocculation moieties include antibodies, lectins, FhuA protein and pb5 protein. When the nucleic acid encodes an antibody, it may be to an antigen of the surface of a member of the genus *Chlamydomonas, Dunaliella, Scenedesmus* or *Hematococcus*, for example, *C. reinhardtii, D. salina, D. tertiolecta, S. dimorphus* or *H. pluvialis*. In certain embodiments, the vector further comprises a nucleic acid encoding an anchoring element that anchors the flocculation moiety to the surface of the organism.

Still another aspect provides a host cell comprising any of the preceding vectors. The host cell may or may not be a non-vascular photosynthetic organism. In some embodiments, the host cell is a member of the genus *Chlamydomonas, Dunaliella, Scenedesmus* or *Hematococcus*, for example *C. reinhardtii, D. salina, D. tertiolecta S. dimorphus* or *H. pluvialis*. In another embodiment, the host cell is a bacterium or a yeast.

Yet another method provides a method for recycling liquid, such as water or a wafer based growth medium, comprising growing a non-vascular photosynthetic organism comprising an exogenous nucleic acid encoding a flocculation moiety in a liquid environment, contacting the organism with a second flocculation moiety that binds directly or indirectly to the first flocculation moiety resulting in flocculation of the organism and separating at least a portion of the liquid in the liquid environment from the organism. The first and second flocculation moieties can be any of the moieties described herein, including, but not limited to, antibodies, carbohydrate binding proteins, carbohydrates, heavy metal flocculants, chemical flocculants, cationic flocculants, and mating type agglutinins. The second flocculation moiety may be attached to the surface of a second organism, which may or may not be a non-vascular photosynthetic organism, or may be attached to a solid support.

Still another aspect provides a method of flocculating a non-vascular photosynthetic organism, comprising contacting the non-vascular photosynthetic organism with a second organism, comprising an exogenous nucleic acid encoding an antibody that binds to an antigen on the surface of the non-vascular photosynthetic organism thereby causing flocculation. In one embodiment, the antibody is expressed on the surface of the second organism. In another embodiment, the antibody is a single chain variable fragment (scFv) antibody. In still another embodiment, the exogenous nucleic acid encodes a fusion or chimeric protein that comprises the antibody and an anchoring component that anchors the antibody to the external surface of the cell membrane or cell wall of the second organism. In one embodiment, the second organism is a bacterium, while in another embodiment, the second organism is a yeast. The non-vascular photosynthetic organism may a green alga for example a member of the genus *Chlamydomonas, Dunaliella, Scenedesmus* or *Hematococcus* and more particularly *C. reinhardtii, D. salina, D. tertiolecta, S. dimorphus* or *H. pluvialis.*

Another aspect provides a method of flocculating a non-vascular photosynthetic organism comprising contacting the non-vascular photosynthetic organism with a second organism comprising an exogenous nucleic acid encoding a flocculation moiety that binds to a surface component of the non-vascular photosynthetic organism thereby causing flocculation of the non-vascular photosynthetic organism. The flocculation moiety can be secreted by the second organism, expressed on the surface of the second organism, or both. The second organism can be a yeast, a bacterium, a non-photosynthetic alga or a photosynthetic alga. In some embodiments, the second organism is *E. coli* or *P. pastoris*. The carbohydrate moiety can be at least one of the members of the group selected from DC-SIGN, dectin-1, dectin-2, HECL, langerin, layilin, mincle, MMGL, E-selectin, P-selectin, L-selectin, DEC-205, Endo 180, mannose receptor, phospholipase A2 receptor, sialoadhesin (siglec-1), siglec-2, siglec-3, siglec-5, siglec-6, siglec-7, siglec-8, siglec-9, siglec-10, siglec-11, and galectins. In particular embodiments, the carbohydrate binding protein is a lectin, for example, a c-type lectin.

In any of the embodiments described herein, an exogenous nucleic acid encoding a flocculation moiety, for example an antibody or a carbohydrate binding protein, may further comprise one or more regulatory elements such as a promoter. Promoters may be constitutive or inducible. Inducible promoters include, but are not limited to light-inducible promoters, quorum-sensitive promoters, temperature-sensitive promoters or nitrogen sensitive promoters.

It should be understood that, unless stated otherwise, when reference is made to the expression or presence of a flocculation moiety on the surface of an organism or solid support such reference refers to the external surface of the organism or solid support, that is the surface facing the environment in which the organism to be flocculated is present.

INCORPORATION BY REFERENCE

All publications, patents, and patent applications mentioned in this specification are herein incorporated by reference to the same extent as if each individual publication, patent, or patent application, was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
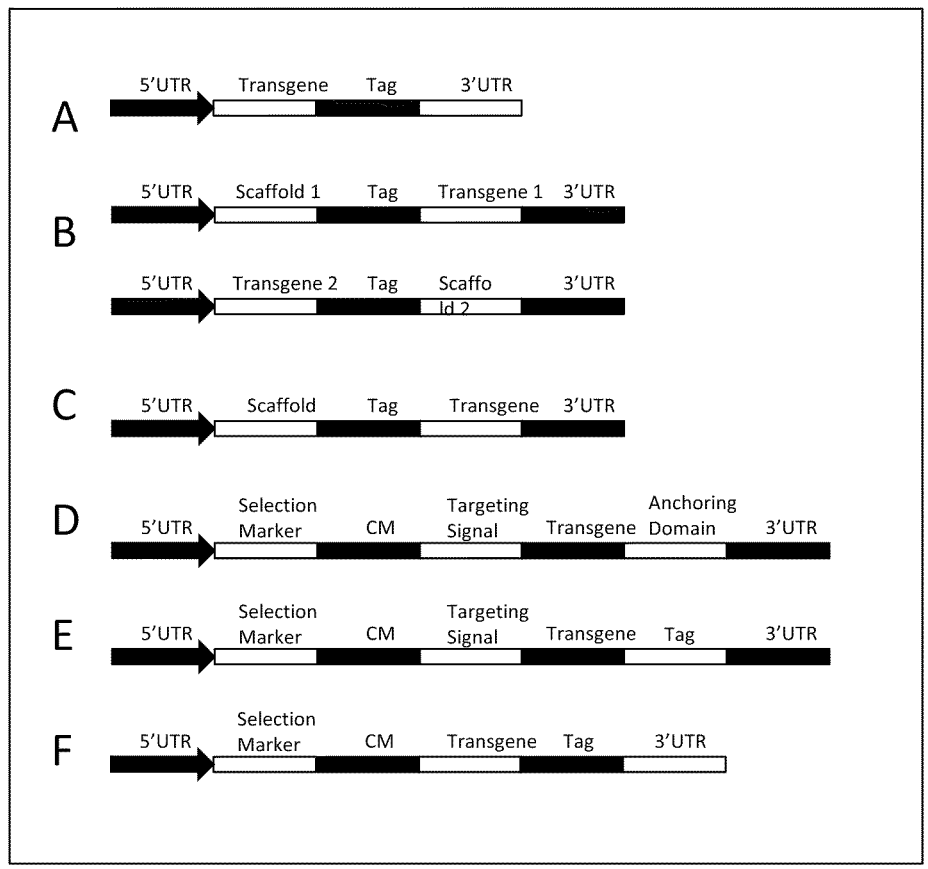
FIG. 1 illustrates various constructs used in the present disclosure

The disclosure herein provides novel approaches to initiating flocculation in photosynthetic organisms, and particularly in non-vascular photosynthetic organisms (NVPO). Growth of photosynthetic organisms, particularly single-celled organisms such as microalgae or cyanobacteria, for industrial or agricultural purposes often involves harvesting the cells of the organisms from liquid environments. Currently, much of this harvesting is performed by centrifugation, belt-press processing, adding chemical flocculants to the liquid environment or some combination of methods. Traditional methods of flocculation may lead to additional costs (e.g., cost of the flocculant, cost for removal of the flocculant from the liquid and/or organisms, etc.) and other problems (e.g., pollution, product purification, etc.). The present disclosure provides novel compositions, host cells and methods for flocculating photosynthetic organisms which can overcome the detriments of traditional flocculation methodologies.

The present disclosure takes advantage of strong molecular interactions between different molecules, for example, antibodies and antigens, proteins and carbohydrates, protein-protein binding pairs, etc. Flocculation pairs (two component complexes) or flocculation complexes (more than two component complexes) may be utilized. In some instances, one member of a flocculation pair or complex will be naturally expressed on an organism which will be flocculated, but the level of production may be genetically enhanced. In other instances, one member of a flocculation pair or complex will be recombinantly expressed on an organism to be flocculated. The organism is then contacted with the second (and/or subsequent) flocculation moiety to induce flocculation. The second or subsequent flocculation moieties may be added extrinsically (e.g., on a solid phase such as a bead or sieve), expressed on a separate organism (which may be the same or different species as the first organism) which is then contacted with the first organism, or expressed on the same organism (e.g., under control of an inducible regulatory element).

One approach utilized involves genetic manipulation of a photosynthetic organism (e.g., an NVPO) to express one or more flocculation moieties. Genetic manipulation may involve transient or integrative transformation of a photosynthetic organism (e.g., Chlamydomonas reinhardtii, Dunaliella salina, Dunaliella tertiolecta, Scenedesmus dimorphus, Hematococcus pluvalis) or a non-photosynthetic organism (e.g. E. coli) with a nucleic acid encoding a flocculation moiety. In some instances, the flocculation moiety is a protein capable of binding to another protein, a carbohydrate or another molecule of interest. For example, C. reinhardtii may be transformed with a gene encoding a C. reinhardtii-cell surface protein fused to an antibody, such that expression of the antibody on the surface of the cell will cause flocculation of the transformed cells or any other target organisms. Antibodies have been produced in C. reinhardtii chloroplasts, but such expression does not yield antibody on the surface of the cell. See, e.g., Mayfield et al., PNAS 100(2):438-42 (2003). Alternatively the antibody can be expressed on the surface of a non-photosynthetic organism. In one embodiment, the non-photosynthetic organism is a prokaryote such as a bacterium. In another embodiment, the non-photosynthetic organism is a eukaryote, for example a fungi, and more particularly a yeast. The cell surface antibodies on the surface of the non-photosynthetic organism then bind to multiple photosynthetic organisms resulting in flocculation.

Host Cells

The present disclosure also contemplates a host cell transformed with one or more of the nucleic acids described herein. In certain embodiments, the host cell is photosynthetic. In some cases, the host cell is photosynthetic and non-vascular. In other cases, the host cell is photosynthetic and vascular. In still other cases the host cell is non-photosynthetic. The host cell can be eukaryotic or prokaryotic. Some host cells may be transformed with multiple genes encoding one or more flocculation moieties. For example, a single transformed cell may contain exogenous nucleic acids encoding one, two, three or more proteins or subunits thereof. For example, an alga such as C. reinhardtii, a bacterium such as E. coli or a cyanobacterium, or a yeast such as Pichia pastoris, may be transformed with a gene encoding an antibody which recognizes a cell-surface protein of the organism to be flocculated, where the antibody is produced as a fusion protein or in two or more subunits which are assembled internally. The organism to be flocculated may be the same or different as the organism expressing the surface protein. Constructs may contain multiple copies of the same gene, and/or multiple genes encoding the same protein, and/or multiple genes with mutations in one or more parts of the coding sequences.

The host cell is transfected with a vector described herein (e.g., a vector comprising one or more flocculation moiety encoding genes). The vector may contain a plastid promoter or a nuclear promoter for transforming the nucleus or a chloroplast or other plastid of the host cell. The vector may also encode a fusion protein or agent that selectively targets the vector product to nucleus or the chloroplast or other plastid. Transfection of a host cell can occur using any method known in the art.

A host organism is an organism comprising a host cell. In certain embodiments, the host organism is photosynthetic. A photosynthetic organism is one that naturally photosynthesizes (has a plastid) or that is genetically engineered or otherwise modified to be photosynthetic. In some instances, a photosynthetic organism may be transformed with a construct which renders all or part of the photosynthetic apparatus inoperable. In some instances it is non-vascular and photosynthetic. The host cell can be prokaryotic. Examples of some photosynthetic prokaryotic organisms of the present invention include, but are not limited to cyanobacteria (e.g., Synechococcus, Synechocystis, Athrospira). The host organism can be unicellular or multicellular. In several embodiments, the host organism is eukaryotic (e.g. green algae). Examples of organisms contemplated herein include, but are not limited to, rhodophyta, chlorophyta, heterokontophyta, tribophyta, glaucophyta, chlorarachniophytes, euglenoids, haptophyta, cryptomonads, dinoflagellata, and phytoplankton. In other embodiments the host organism is non-photosynthetic. Non-photosynthetic host organisms include bacteria and yeast. Examples of suitable bacterial host organisms can be found in the phylum proteobacteria and include, but are not limited to *Escherichia coli*. Examples of suitable yeast organism can be found in the phylum Ascomycota and include, but are not limited to *Pichia pastoris* and *Saccharomyces cerevisiae*.

A host organism may be grown under conditions which permit photosynthesis, however, this is not a requirement (e.g., a host organism may be grown in the absence of light). In some instances, the host organism may be genetically modified in such a way that photosynthetic capability is diminished and/or destroyed. In growth conditions where a host organism is not capable of photosynthesis (e.g., because of the absence of light and/or genetic modification), typically, the organism will be provided with the necessary nutrients to support growth in the absence of photosynthesis. For example, a culture medium in (or on) which an organism is grown, may be supplemented with any required nutrient, including an organic carbon source, nitrogen source, phosphorous source, vitamins, metals, lipids, nucleic acids, micronutrients, or an organism-specific requirement. Organic carbon sources include any source of carbon which the host organism is able to metabolize including, but not limited to, acetate, simple carbohydrates (e.g., glucose, sucrose, lactose), complex carbohydrates (e.g., starch, glycogen), proteins, and lipids. One of skill in the art will recognize that not all organisms will be able to sufficiently metabolize a particular nutrient and that nutrient mixtures may need to be modified from one organism to another in order to provide the appropriate nutrient mix.

A host organism can be grown on land, e.g., in ponds, aqueducts, landfills, or in closed or partially closed bioreactor systems. The host organisms can also be grown directly in water, e.g., oceans, seas, lakes, rivers, reservoirs, etc. In embodiments where algae are mass-cultured, the algae can be grown in high density photobioreactors. Methods of mass-culturing algae are known in the art. For example, algae can be grown in high density photobioreactors (see, e.g., Lee et al, *Biotech. Bioengineering* 44:1161-1167, 1994) and other bioreactors (such as those for sewage and waste water treatments) (e.g., Sawayama et al, *Appl. Micro. Biotech.*, 41:729-731, 1994). Additionally, algae may be mass-cultured to remove heavy metals (e.g., Wilkinson, *Biotech. Letters*, 11:861-864, 1989), hydrogen (e.g., U.S. Patent Application Publication No. 20030162273), and pharmaceutical compounds.

An exemplary group of organisms are the green algae. One example, *Chlamydomonas*, is a genus of unicellular green algae (Chlorophyta). These algae are found in soil, fresh water, oceans, and even in snow on mountaintops. Algae in this genus have a cell wall, a chloroplast, and two anterior flagella allowing mobility in liquid environments. More than 500 different species of *Chlamydomonas* have been described.

The most widely used laboratory species is *C. reinhardtii*. Cells of this species are haploid, and can grow on a simple medium of inorganic salts, using photosynthesis to provide energy. They can also grow in total darkness if acetate is provided as a carbon source. When deprived of nitrogen, *C. reinhardtii* cells can differentiate into isogametes. Two distinct mating types, designated mt+ and mt−, exist. These fuse sexually, thereby generating a thick-walled zygote which forms a hard outer wall that protects it from various environmental conditions. The controlled expression of mating type agglutinins can be used to aid in flocculation. When restored to nitrogen culture medium in the presence of light and water, the diploid zygospore undergoes meiosis and releases four haploid cells that resume the vegetative life cycle. In mitotic growth the cells double as fast as every eight hours. *C. reinhardtii* cells can grow under a wide array of conditions. While a dedicated, temperature-controlled space can result in optimal growth, *C. reinhardtii* can be readily grown at room temperature under standard fluorescent lights. The cells can be synchronized by placing them on a light-dark cycle and depriving them of acetate.

The nuclear genetics of *C. reinhardtii* is well established. There are a large number of mutants that have been characterized and the *C. reinhardtii* center (www.chlamy.org) maintains an extensive collection of mutants, as well as annotated genomic sequences of *Chlamydomonas* species. A large number of chloroplast mutants as well as several mitochondrial mutants have been, developed in. *C. reinhardtii*.

The term "plant" is used broadly herein to refer to a eukaryotic organism containing plastids, particularly chloroplasts, and includes any such organism at any stage of development, or to past of a plant, including a plant cutting, a plant cell, a plant cell culture, a plant organ, a plant seed, and a plantlet. A plant cell is the structural and physiological unit of the plant, comprising a protoplast and a cell wall. A plant cell can be in the form of an isolated single cell or a cultured cell, or can be part of higher organized unit, for example, a plant tissue, plant organ, or plant. Thus, a plant cell can be a protoplast, a gamete producing cell, or a cell or collection of cells that can regenerate into a whole plant. As such, a seed, which comprises multiple plant cells and is capable of regenerating into a whole plant, is considered plant cell for purposes of this disclosure. A plant tissue or plant organ can be a seed, protoplast, callus, or any other groups of plant cells that is organized into a structural or functional unit. Particularly useful parts of a plant include harvestable parts and parts useful for propagation of progeny plants. A harvestable part of a plant can be any useful part of a plant, for example, flowers, pollen, seedlings, tubers, leaves, stems, fruit, seeds, roots, and the like. A part of a plant useful for propagation includes, for example, seeds, fruits, cuttings, seedlings, tubers, rootstocks, and the like.

Vectors

The vectors described herein may be capable of stable transformation of multiple photosynthetic organisms, including, but not limited to, photosynthetic bacteria (including cyanobacteria), cyanophyta, prochlorophyta, rhodophyta, chlorophyta, heterokontophyta, tribophyta, glaucophyta, chlorarachniophytes, euglenophyta, euglenoids, haptophyta, chrysophyta, cryptophyta, cryptomonads, dinophyta, dinoflagellata, pyrmnesiophyta, bacillariophyta, xanthophyta, eustigmatophyta, raphidopbyta, phaeophyta, and phytoplankton. Other vectors are capable of stable transformation of *C. reinhardtii, D. salina, D. tertiolecta, S. dimorphus* or *H. pluvalis*. Still other vectors are capable of stable transformation of non-photosynthetic organisms such as yeast and bacteria. Vectors for stable transformation of bacteria and yeast are well known in the art and can be obtained from commercial vendors. Expression vectors can be engineered to produce heterologous and/or homologous protein(s) of interest (e.g., antibodies, mating type agglutinins, etc.). Such vectors are useful for recombinantly producing the protein of interest. Such vectors are also useful to modify the natural phenotype of host cells (e.g., expressing a flocculation moiety).

An expression cassette can be constructed in an appropriate vector. In some instances, the cassette is designed to express one or more protein-coding sequences in a host cell.

Such vectors can be constructed using standard techniques known in the art. In a typical expression cassette, the promoter or regulatory element is positioned on the 5' or upstream side of a coding sequence whose expression is desired. In other cassettes, a coding sequence may be flanked by sequences which allow for expression upon insertion into a target genome (e.g., nuclear or plastid). For example, a nucleic acid encoding a flocculation moiety may be inserted into a nuclear genome of a host cell, such that the flocculation moiety expression is controlled by a naturally occurring regulatory element. In the present disclosure, any regulatory element which provides expression under appropriate conditions such that the mRNA or protein product is expressed to a level sufficient to produce flocculation of the transformed NVPO can be used.

One or more additional protein, coding sequences can be operatively fused downstream or 3' of a promoter. Coding sequences for single proteins can be used, as well as coding sequences for fusions of two or more proteins. Coding sequences may also contain, additional elements that would allow the expressed proteins to be targeted to the cell surface and either be anchored on the cell surface or be secreted to the environment. A selectable marker is also employed in the design of the vector for efficient selection for green algae transformed by the vector. Both a selectable marker and another sequence which one desires to introduce may be introduced fused to and downstream of a single promoter. Alternatively, two protein coding sequences can be introduced, each under the control of a promoter.

A regulatory element, as the term is used herein, broadly refers to a nucleotide sequence that regulates the transcription or translation of a polynucleotide or the localization of a polypeptide to which it is operatively linked. A regulatory element may be native or foreign to the nucleotide sequence encoding the polypeptide. Such elements include, but are not limited to, a ribosome binding site (RBS), a leader, a polyadenylation sequence, a pro-peptide sequence, a promotes, a signal peptide sequence, and a transcription terminator, an enhancer, an initiation (start) codon, a splicing signal for intron excision and maintenance of a correct reading frame, a STOP codon, an amber or ochre codon, and/or an internal ribosome entry site (IRES). Typically, a regulatory element includes a promoter and transcriptional and translational stop signals. Elements may be provided with linkers for the purpose of introducing specific restriction sites facilitating ligation of the control sequences with the coding region of the nucleotide sequence encoding a polypeptide. In some instances, such vectors include promoters. Additionally, a cell compartmentalization signal (i.e., a sequence that targets a polypeptide to the cytosol, nucleus, chloroplast membrane or cell membrane). Such signals are well known in the art and have been widely reported (see, e.g., U.S. Pat. No. 5,776, 689). Promoters useful for the present invention may come from any source (e.g., viral, bacterial, fungal, protist, animal). The promoters contemplated herein can be specific to photosynthetic organisms, non-vascular photosynthetic organisms, vascular photosynthetic organisms (e.g., algae, flowering plants), yeast and bacteria. As used herein, the term "non-vascular photosynthetic organism," refers to any macroscopic or microscopic organism, including, but not limited to, algae, cyanobacteria and photosynthetic bacteria, which do not have a vascular system such as that found in higher plants. In some instances, the nucleic acids above are inserted into a vector that comprises a promoter of a photosynthetic organism, e.g., algae. The promoter can be a promoter for expression in the nucleus or in a chloroplast and/or other plastid. Examples of promoters contemplated for insertion with any of the nucleic acids herein into the chloroplast include those disclosed in US Application No. 2004/0014174. Promoters suitable for use in bacteria, include but are not limited to, promoters from Simian Virus 40 (SV40), Mouse Mammary Tumor Virus (MMTV) promoter, the HIV Long Terminal Repeat (LTR) promoter, Moloney virus, ALV, Cytomegalovirus (CMV) such as the CMV immediate early promoter, Epstein Barr Virus (EBV), and Rous Sarcoma Virus (RSV). The promoter can be a constitutive promoter or an inducible promoter. A promoter typically includes necessary nucleic acid sequences near the start site of transcription, (e.g., a TATA element).

To construct the vector, the upstream DNA sequences of a gene expressed under control of a suitable promoter may be restriction mapped and areas important for the expression of the protein characterized. The exact location of the start codon of the gene is determined and, making use of this information and the restriction map, a vector may be designed for expression of a heterologous protein by removing the region responsible for encoding the gene's protein but leaving the upstream region found to contain, the genetic material responsible for control of the gene's expression. A synthetic oligonucleotide is preferably inserted in the location where the protein sequence once was, such that any additional gene could be cloned in using restriction endonuclease sites in the synthetic oligonucleotide (i.e., a multicloning site). An unrelated gene (or coding sequence) inserted at this site would then be under the control of an extant start codon and upstream regulatory region that will drive expression of the foreign (i.e., not normally present) protein encoded by this gene. Once the gene for the foreign protein is put into a cloning vector, it can be introduced into the host organism using any of several methods, some of which, might be particular to the host organism. Variations on these methods are described in the general literature. Manipulation of conditions to optimize transformation for a particular host is within the skill of the art.

Regarding the type of plasmid used for the insertion of the various DNA expression cassette, any convenient plasmid may be employed. The plasmids, or vectors, may include such vectors as pUC or its derivatives, pBR322, pBluescript, or pGEM. Other vectors included pPIC3.5K, pPIC9K and pAO815 available from Invitrogen (Carlsbad, Calif. USA). A particular plasmid is chosen based on the nature of the markers, availability of convenient restriction sites, copy number and the like. The DNA sequence encoding the polypeptide of interest may be synthetic, naturally derived, or any combination thereof. Depending upon the nature of the DNA sequence of interest, it may be desirable to synthesize the sequence with codons preferred in NVPO. The DNA sequence encoding the polypeptide of interest may be a structural gene or a portion thereof which provides for a desired expression product. The gene may be any gene, whether native, mutant of the native, or foreign to the host. The term foreign is intended to denote a gene not endogenous to the host cell, but may include indigenous sequences, such as viral sequences and bacterial sequences which are naturally associated with the NVPO.

A vector utilized can also contain one or more additional nucleotide sequences that confer desirable characteristics on the vector, including, for example, sequences such as cloning sites that facilitate manipulation of the vector, regulatory elements that direct replication of the vector or transcription of nucleotide sequences contain therein, sequences that encode a selectable marker, and the like. As such, the vector can contain, for example, one or more cloning sites such as a multiple cloning sites, which can, but need not, be positioned such that a heterologous polynucleotide can be inserted into the vector and operatively linked to a desired element. The vector also can contain a prokaryote origin of replication (ori), for example, an *E. coli* ori or a cosmid ori, thus allowing passage of the vector in a prokaryote host cell, as well as in a plant chloroplast, as desired. Such features, combined with appropriate selectable markers, allows for the vector to be "shuttled" between the target host cell and the bacterial and/or yeast cell. The ability to passage a shuttle vector in a secondary host may allow for more convenient manipulation of the features of the vector. For example, a reaction mixture containing the vector and putative inserted polynucleotides of interest can be transformed into prokaryote host cells such as *E. coli*, amplified and collected using routine methods, and examined to identify vectors containing an insert or construct of interest. If desired, the vector can be further manipulated, for example, by performing site directed mutagenesis of the inserted polynucleotide, then again amplifying and selecting vectors having a imitated polynucleotide of interest. A shuttle vector then can be introduced into plant cell chloroplasts, wherein a polypeptide of interest can be expressed and, if desired, isolated.

A vector or other recombinant nucleic acid molecule may include a nucleotide sequence encoding a reporter polypeptide or other selectable marker. The term "selectable marker" refers to a polynucleotide (or encoded polypeptide) that confers a detectable phenotype. A reporter generally encodes a detectable polypeptide, for example, a green fluorescent protein or an enzyme such as luciferase, which, when contacted with an appropriate agent (a particular wavelength of light or luciferin, respectively) generates a signal that can be detected by eye or using appropriate instrumentation (Giacomin, *Plant Sci.* 116:59-72, 1996; Scikantha, *J. Bacterial.* 178:121, 1996; Gerdes, *FEBS Lett.* 389:44-47, 1996; see, also, Jefferson, *EMBO J.* 6:3901-3907, 1997, fl-glucuronidase). A selectable marker generally is a molecule that, when present or expressed in a cell, provides a selective advantage (or disadvantage) to the cell containing the marker, for example, the ability to grow in the presence of an agent that otherwise would kill the cell.

A selectable marker can provide a means to obtain prokaryotic cells or plant cells or both that express the marker and, therefore, can be useful as a component of a vector (see, for example, Bock, supra, 2001). Examples of selectable markers include, but are not limited to, those that confer antimetabolite resistance, for example, dihydrofolate reductase, which confers resistance to methotrexate (Reiss, *Plant Physiol. (Life Sci. Adv.)* 13:143-149, 1994); neomycin phosphotransferase, which confers resistance to the aminoglycosides neomycin, kanamycin and paromycin (Herrera-Estrella, *EMBO J.* 2:987-995, 1983), hygro, which confers resistance to hygromycin (Marsh, *Gene* 32:481-485, 1984), trpB, which allows cells to utilize indole in place of tryptophan; hisD, which allows cells to utilize histinol in place of histidine (Hartman, *Proc. Natl. Acad. Sci., USA* 85:8047, 1988); mannose-6-phosphate isomerase which allows cells to utilize mannose (WO 94/20627); ornithine decarboxylase, which confers resistance to the ornithine decarboxylase inhibitor, 2-(difluoromethyl)-DL-ornithine (DFMO; McConlogue, 1987, In: Current Communications in Molecular Biology, Cold Spring Harbor Laboratory ed.); and deaminase from *Aspergillus terreus*, which confers resistance to Blasticidin S (Tamura, *Biosci. Biotechnol. Biochem.* 59:2336-2338, 1995). Additional selectable markers include those that confer herbicide resistance, for example, phosphinothricin acetyltransferase gene, which confers resistance to phosphinothricin (White et al., *Nucl. Acids Res.* 18:1062, 1990; Spencer et al., *Theor. Appl. Genet.* 79:625-633, 1990), a mutant EPSPV-synthase, which confers glyphosate resistance (Hinchee et al., *BioTechnology* 91:915-922, 1998), a mutant acetolactate synthase, which confers imidazolione or sulfonylurea resistance (Lee et al., *EMBO J.* 7:1241-1248, 1988), a mutant psbA, which confers resistance to atrazine (Smeda et al., *Plant Physiol.* 103:911-917, 1993), or a mutant protoporphyrinogen oxidase (see U.S. Pat. No. 5,767,373), or other markers conferring resistance to an herbicide such as glufosinate. Selectable markers include polynucleotides that confer dihydrofolate reductase (DHFR) or neomycin resistance for eukaryotic cells and tetracycline; ampicillin resistance for prokaryotes such as *E. coli*; and bleomycin, gentamycin, glyphosate, hygromycin, kanamycin, methotrexate, phleomycin, phosphinotricin, spectinomycin, streptomycin, sulfonamide and sulfonylurea resistance in plants (see, for example, Maliga et al., Methods in Plant Molecular Biology, Cold Spring Harbor Laboratory Press, 1995, page 39).

One or more codons of an encoding polynucleotide can be biased to reflect the preferred codon usage of the host cell, or an organelle thereof (e.g. chloroplasts). Most amino acids are encoded by two or more different (degenerate) codons, and it is well recognized that various organisms utilize certain codons in preference to others. The codon bias of *C. reinhardtii* has been reported (See U.S. Application 2004/0014174) as has codon bias in bacteria and yeast (See e.g. *Gene* 18:199-209 (1982); *FEBS Lett.*, 285:165-169 (1991); *J. Biol. Chem.*, 257:3026-3031 (1982)).

The term "biased," when used in reference to a codon, means that the sequence of a codon in a polynucleotide has been changed such that the codon is one that is used preferentially in the target which the bias is for, e.g., alga cells, chloroplasts, bacteria or yeast. A polynucleotide that is biased for a particular codon usage can be synthesized de novo, or can be genetically modified using routine recombinant DNA techniques, for example, by a site directed mutagenesis method, to change one or more codons such that they are biased for chloroplast codon usage. Codon bias can be variously skewed in different plants, including, for example, in alga as compared to tobacco. Generally, the codon bias selected reflects codon usage of the plant (or organelle therein) which is being transformed with the nucleic acids of the present invention. For example, where *C. reinhardtii* is the host, the chloroplast codon usage may be biased to reflect nuclear or chloroplast codon usage (e.g., about 74.6% AT bias in the third codon position for sequences targeting the chloroplast). Alternatively, when bacteria or yeast are used as the host organism, codon usage may be biased for those organisms.

Disclosed herein are vectors employed in various flocculation methods. These vectors or plasmids may comprise regulatory elements recognized by the gene-transcription machinery of the host organism used, including for nuclear or plastid genes, coding sequences operably linked to the regulatory elements, selection markers allowing the selection for host cells transformed by the vector, and other elements allowing the vector to be stably integrated into the nuclear or plastid genome of a host organism. Examples of regulatory elements include, but are not limited to, constitutive promoters, light-inducible promoters, quorum-sensing promoters, temperature-sensitive promoters, or nitrogen-starvation responsive promoters. An example of light-inducible promoter is described in U.S. Pat. No. 6,858,429. Examples of flocculation moieties which may be encoded by polynucleotides used in the present disclosure include, but are not limited to, FhuA, pb5, *Chlamydomonas* male gamete agglutinin (mt+), *Chlamydomonas* female gamete agglutinin (mt−), lectin, carbohydrate binding proteins, antibodies (e.g., anti-carbohydrate antibody, anti-flagella antibody, anti-Fus1 antibody, anti-cell surface protein antibodies). Examples of selection markers may include, but are not limited to, kanamycin, phleomycin, bleomycin, hygromycin, or zeocin.

Transformation of Host Cells

Transformed cells are produced by introducing homologous and/or heterologous DNA into a population of target cells and selecting the cells which have taken up the DNA. For example, transformants containing exogenous DNA with a selectable marker which confers resistance to kanamycin may be grown in an environment containing kanamycin.

The basic techniques used for transformation and expression in photosynthetic organisms are similar to those commonly used for *E. coli, Saccharomyces cerevisiae* and other species and include calcium phosphate transfection, DEAE-dextran mediated transfection, Polybrene, protoplast fusion, liposomes, direct microinjection into the nuclei, scrape loading, and electroporation. Transformation methods customized for an NVPO, e.g., the chloroplast of a strain of algae, are known in the art. These methods have been described in a number of texts for standard molecular biological manipulation (see Packer & Glaser, 3988, "Cyanobacteria", Meth. Enzymol., Vol. 167; Weissbach & Weissbach, 1988, "Methods for plant molecular biology," Academic Press, New York, Sambrook, Fritsch & Maniatis, 1989, "Molecular Cloning: A laboratory manual," 2nd edition Cold Spring Harbor Laboratory Press, Cold Spring Harbor, N.Y.; and Clark M S, 1997, Plant Molecular Biology, Springer, N.Y.). These methods include, for example, biolistic devices (See, for example, Sanford, Trends In Biotech. (1988) 6: 299-302, U.S. Pat. No. 4,945,050; electroporation (Fromm et al., Proc. Nat'l. Acad. Sci. (USA) (1985) 82: 5824-5828); use of a laser beam, electroporation, microinjection or any other method capable of introducing DNA into a host cell (e.g., an NVPO).

Plastid transformation is a routine and well known method for introducing a polynucleotide into a plant cell chloroplast (see U.S. Pat. Nos. 5,451,513, 5,545,817, and 5,545,818; WO 95/16783; McBride et al., *Proc. Natl. Acad. Sci.*, USA 91:7301-7305, 1994). In some embodiments, chloroplast transformation involves introducing regions of chloroplast DNA flanking a desired nucleotide sequence, allowing for homologous recombination, of the exogenous DNA into the target chloroplast genome. In some instances one to 1.5 kb flanking nucleotide sequences of chloroplast genomic DNA may be used. Using this method, point mutations in the chloroplast 16S rRNA and rps12 genes, which confer resistance to spectinomycin and streptomycin, can be utilized as selectable markers for transformation. (Svab et al., *Proc. Natl. Acad. Sci., USA* 87:8526-8530, 1990), and can result in stable homoplasmic transformants, at a frequency of approximately one per 100 bombardments of target leaves.

Microprojectile mediated transformation also can be used to introduce a polynucleotide into a plant cell (Klein et al., *Nature* 327:70-73, 1987). This method utilizes microprojectiles such as gold or tungsten, which are coated with the desired polynucleotide by precipitation with calcium chloride, spermidine or polyethylene glycol. The microprojectile particles are accelerated at high speed into a plant tissue using a device such as the BIOLISTIC PD-1000 particle gun (Bio-Rad; Hercules Calif. USA). Methods for the transformation using biolistic methods are well known in the art (see, e.g.; Christou, *Trends in Plant Science* 1:423-431, 1996). Microprojectile mediated transformation has been used, for example, to generate a variety of transgenic plant species, including cotton, tobacco, corn, hybrid poplar and papaya. Important cereal crops such as wheat, oat, barley, sorghum and rice also have been transformed using microprojectile mediated delivery (Duan et al., *Nature Biotech.* 14:494-498, 1996; Shimamoto, *Curr. Opin. Biotech.* 5:158-362, 1994). The transformation of most dicotyledonous plants is possible with the methods described above. Transformation of monocotyledonous plants also can be transformed using, for example, biolistic methods as described above, protoplast transformation, electroporation of partially permeabilized cells, introduction of DNA using glass fibers, the glass bead agitation method, and the like. Transformation frequency may be increased by replacement of recessive rRNA or r-protein antibiotic resistance genes with a dominant selectable marker, including, but not limited to the bacterial aadA gene (Svab and Maiiga, *Proc. Natl. Acad. Sci., USA* 90:913-917, 1993).

Flocculation Moieties

To harvest a product of interest from a host cell of the present invention (e.g., an NVPO), efficient separation of the host cell from the liquid in which it is grown is often useful. Various methods of separating the organism from the liquid have been used in the past. Centrifugation, for example, has been successfully used in separating cells in small scale culture from liquid media. For large scale applications, however, which usually involve growing an organism in large quantities of water (e.g., a pond, a lake, a bioreactor, etc.), centrifugation can be time-consuming and or cost-prohibitive. Flocculation is an alternative approach to the separation of cells for large and small scale applications. Certain chemical flocculants, such as heavy metals, pose a challenge as it the metal may need to be removed from the flocculated organism for downstream processes (e.g., enzyme purification, nutriceutical production, transesterification of triglycerides, etc.). Strains of organisms (e.g., NVPOs) engineered to express flocculation moieties, on the other hand, do not present the problem of removing a dangerous, costly, or polluting flocculant from the organisms and/or the liquid environment. Thus, one novel aspect of the present disclosure is the production of an organism engineered to produce one or more flocculation moieties.

The flocculation moiety can be incorporated into an organism, either photosynthetic or non-photosynthetic, by transformation with vectors, such as those described herein. Techniques involved in such processes include, but are not limited to, the development of suitable expression cassette, insertion (i.e. transformation) of the expression cassette into a host cell, and screening the host cell expressing the desired flocculation moiety. Depending on the design of the vector, the flocculation moiety can be of constitutively expressed (e.g., at all times) or can inducibly expressed (e.g., temperature-induced, quorum-induced, etc.). Engineered photosynthetic organisms capable of expressing one or more flocculation moieties can be used for flocculation with or without the addition of other compounds. For example, a non-photosynthetic organisms such as *E. coli* can be transformed so as to produce a carbohydrate-binding protein, for example a lectin, or an antibody fused to a cell surface protein (for example LppOmpA, beta-autotransporter, etc.) such that when expressed, the fusion protein is present on the cell surface and binds to multiple organisms of interest, such as a green algae, to cause flocculation. Alternatively, a green algae such as *C. reinhardtii*, may be transformed to produce a carbohydrate-binding protein, for example a lectin, or an antibody fused to a cell surface protein, for example GP1, such that the fission protein is expressed at the cell surface and binds to multiple organisms of interest, such as green algae, to cause flocculation.

Alternately, one host organism (e.g., *C. reinhardtii*) may be transformed so as to produce the FhuA protein from *E. coli* and a second host organism—the same or different species than the first organism—may be transformed so as to produce the T5 phage tail protein, pb5. FhuA and pb5 form a very stable 1:1 stoichiometric complex, thus, by combining the two transformed host cells at a desired time, or by controlling expression of the two flocculation moieties in the different strains to only express the flocculation moieties at a desired time, binding between the two moieties will cause flocculate via the interaction of the two moieties.

A flocculating moiety will typically be expressed such that it is present on the outer surface of the host cell (e.g., cell wall and/or cell membrane), in some instances, a flocculation moiety is secreted by the host cell into the surrounding environment. Standard molecular biology techniques allow the targeting of a recombinantly expressed protein to various subcellular compartments of a host cell. Examples of such subcellular compartments include Golgi, lysosome, secretion system, cell wall or plasma membrane. Thus, in some instances, the vectors useful in the present disclosure will contain DNA sequences encoding one or more specialized polypeptides (e.g., signal peptides) that are capable of directing recombinant proteins to subcellular compartments if the signal peptide is operably linked to the recombinant protein.

Candidates for genes expressing flocculation moieties can be obtained from a variety of organisms including eukaryotes, prokaryotes, or viruses. In some instances, a flocculation moiety is one member of a protein binding pair. Protein pairs forming strong protein-protein complexes are useful as flocculation moieties. Self-aggregating proteins, proteins capable of forming multimeric complexes are also useful as flocculants. Carbohydrate moieties of glycoproteins (e.g., arabinosyl, galactosyl, mannosyl, and rhamnosyl residues), membrane and/or cell wall carbohydrates (e.g., alginic acid, xylanes, mannanes, agarose, carrageenan, porphyran, furcelleran, etc.), proteins increasing the production of certain carbohydrates or glycolipids may also be used to induce flocculation as certain classes of carbohydrates are known components of protein complex formation.

Flocculation moieties can also be recombinantly expressed in host cells and purified to a useful level (e.g., homogeneity). The purified flocculants can be added to a target cell culture to cause flocculation. Such flocculants typically will not pose the same challenges as the use of heavy metal flocculants. For example, a recombinant lectin can be produced by a host cell (e.g. secreted or produced on the surface), collected, and introduced into a culture of an organism to be flocculated.

One of skill in the art will recognize that multiple types of molecules can be utilized in the practice of the present methods. Disclosed herein are various exemplary proteins, carbohydrates, antibodies, and other moieties which may be utilized as a flocculation moiety, either when expressed by a microorganism or by incorporation in the liquid culture media. These examples are meant to provide illustration of the types of molecules which can be utilized and are not intended to be limiting.

Proteins, as a category, are known to bind and/or complex with other macromolecules and compounds. As such, proteins may be utilized as flocculation moieties. Carbohydrate binding proteins (e.g., lectins), for example, are one category of protein which is useful for a flocculation moiety. Carbohydrate binding proteins recognize and bind to a variety of cell surface carbohydrates, carbohydrate moieties, polysaccharide side chains of glycoproteins, glycosylated proteins, glycopeptides, and/or cell surface proteins. Thus, in one embodiment, c-type lectin is expressed on the cell wall of C. reinhardtii, which induces flocculation by binding to a glycoprotein on the surface of C. reinhardtii cells. Examples of these flocculation moieties include, but are not limited to, lysophosphatidic acid, c-type lectin, Gal/GalNAc, O-linked sugars, O-linked polysaccharides, GlcNAc, phospholipase A2, GalNAc—SO$_4$, sialic acid, glycosphingolipids, glucose monomycolate, lipoarabinomannan, phosphatidyl inositols, hexosyl-1-phosphoisoprenoids, mannosyl-phosphodolicols, α-galactosylceramide, or terminal galactoside. Examples of carbohydrate binding proteins include, but are not limited to, DC-SIGN, dectin-1, dectin-2, HECL, langerin, layilin, mice, MMGL, E-selectin, P-selectin, L-selectin, DEC-205, Endo 180, mannose receptor, phospholipase A2 receptor, sialoadhesin (siglec-1), siglec-2, siglec-3, siglec-4, siglec-5, siglec-6, siglec-7, siglec-8, siglec-9, siglec-10, siglec-11, or galectins.

Another category of proteins that may be utilized as flocculation moieties is antibodies. For example, antibodies against known cell surface antigens expressed on an organism can be used. Expression of such antibodies may lead antigen-antibody complex formation which can subsequently lead to flocculation of an organism expressing the antibody where the antibody specifically binds to a cell-surface antigen on the transformed strain, or a different strain or organism. For example, C. reinhardtii may be transformed to inducibly express a single chain variable fragment (scFv) of an antibody, which detects an antigen on the external surface of an organism. The surface antigen may be naturally occurring on the surface of C. reinhardtii or another organism or may be the result transformation of the organism to produce the cell surface antigen. The antibodies used may be univalent, multivalent, or polyvalent. Other antibodies against various glycoproteins are known in the art (See, e.g., Matsuda et. al, J. Plant. Res., 100:373-384, 1987; Musgrave et al., Planta, 170: 328-335, 1987). The antibodies can be anchored on the cell surface by creating a fusion protein comprising a protein expressed at the cell surface, for example the cell membrane or cell wall. Alternately, the antibody can be engineered to be secreted by the host cell into the surrounding environment to cause flocculation. Antibodies recognizing cell wall components or engineered antibodies of the host cell can be added to the media or other growth environment to induce flocculation. Antibodies known for forming stable complexes with specific epitopes can be utilized as flocculation moieties. In some instances, antibodies may be utilized which target a naturally occurring epitope.

A first organism expressing such antibodies can be paired with another organism expressing the corresponding epitope so as to induce flocculation upon combination. The corresponding epitope may be naturally occurring or may be genetically engineered. Alternately, the corresponding epitope may be added to the media or other growth environment when flocculation is desired. Epitopes may be coupled to solid state supports such as beads, meshes, sieves, etc. to facilitate flocculation. Examples of antibodies useful for the present invention include, but are not limited to, anti-HA tag antibody, anti-His tag antibody, anti-Myc tag antibody, anti-AU1 tag antibody, anti-GST tag antibody, anti-KT3 tag antibody, anti-MAT tag antibody, anti-MBP tag antibody, anti-S tag antibody, anti-S1 tag antibody, anti-SNAP tag antibody, anti-SRT tag antibody, anti-V5 tag antibody, anti-VSV-G tag antibody, anti-TAP tag antibody, and anti-Trx antibody. One of skill in the art will recognize that a single host cell may express more than one flocculation moiety from one or more categories. For example an organism may be transformed to express two different antibodies or an antibody and a carbohydrate-binding protein.

In some embodiments, a flocculation moiety is an antibody to a cell surface epitope of a cell of interest. The particular cell surface epitope may be present on a cell surface protein. Examples of such proteins include, but are not limited to HRP-2, PHC21, TSG-C1, LMR3, VSP (1, 2, 3, 4), HRP3, GP1, FAS1, FAS2, FAS3, E_GWH.1280.7.1, GAS30, MMP14, ZAP2-2, MIN1, or GOX1 from *C. reinhardtii* and p150 from *D. salina*. Methods of producing antibodies to a given protein are well known in the art and may comprise culturing a photosynthetic organism; fractionating the membrane and/or cell wall portion of the microorganism; injecting the fraction to an appropriate host animal for immunization; withdrawing sera from the immunized animal; and screening, selecting and purifying one or more antibodies reacting to the fraction. Also, for example where the immunized animal is a mouse, immune cells producing the antibody of interest can be subjected to routine hybridoma formation and culture techniques to produce monoclonal antibodies of interest. In another embodiment, proteins are further purified from the membrane fraction and are utilized in high-throughput screening system as a target of phage display technique whereby DNA sequences expressing a portion of the antibody polypeptide interacting with the target are identified. Phage display techniques are known in the art. See, e.g., U.S. Pat. No. 5,855,885; McCafferty et al. *Nature,* 348:552-54, 1990.

Another category of proteins which may be utilized as flocculation moieties include proteins which form a binding pair. This category includes, among others, proteins forming multimeric complexes and proteins forming a complex with another class of protein. For example, the *E. coli* protein FhuA is a monomeric iron transporter channel with a single membrane spanning domain that can be overexpressed; pb5 is a T5 phage tail protein that uses FhuA as the phage receptor. The interaction between the two proteins is very stable. Such protein pairs can be utilized as flocculation moieties. For example, in one embodiment, FhuA is expressed in one strain of *D. salina* and pb5 is expressed in a second strain of *D. salina*. Upon combination of the two strains, flocculation occurs due to interaction of the two proteins. One of skill in the art will recognize that many other protein binding pairs exist and can be utilized. To allow for interaction between some proteins, it may be necessary to engineer the proteins such that they are inserted into the cell membrane and/or cell wall.

Controlling the Timing of Flocculation

Having control over the timing of flocculation may be advantageous in some instance to control flocculation. For example, by controlling the time of flocculation, an operator of a target culture system may ensure efficient use of nutrients, time of harvesting, quantity of harvested organism, and/or maximal product production. One of skill in the art will recognize that optimal conditions may vary according to multiple factors, but such determinations of culture medium preparation are routine. For flocculation moieties expressed by a given host organism, the timing of flocculation can be controlled by incorporating one or more regulatory elements (e.g., promoters) into the design of an expression cassette. Such an approach may allow for expression of a flocculation moiety only at a desired time. As is apparent from the present disclosure, multiple routes are available to control timing of flocculation. Although exemplary approaches to controlling the timing of flocculation, this discussion is not meant to limit these approaches to the particular approaches mentioned herein.

For expression of some flocculation moieties, regulatory elements resulting in constitutive expression can be used. Thus, the flocculation moiety under the control of such regulatory elements is expected to be produced throughout the life of the host cell. Examples of regulatory elements are 35S or 19S region of cauliflower mosaic virus (CaMV), the coat promoter of TMV, promoters of nopaline synthase, man- nopine synthase, or octopine synthase of *Agrobacterium*, cell promoter, chalcone synthase promoter, actin promoter, adhI promoter, ubiquitin promoter, or patatin promoter. To induce flocculation, two separate strains constitutively expressing one part of a flocculation pair (e.g., antibody-antigen, protein binding pair, etc.) may be combined when flocculation is desired. In such instances, the flocculation moiety on one strain may be naturally occurring (e.g., the first strain produces a recombinant lectin which recognizes a glycoprotein on the second strain). Alternately, flocculation of a single strain may be induced by adding the second part of a flocculation pair to the culture or environment of the strain when flocculation is desired. In still another approach, host cells containing one part of a flocculation pair which is constitutively expressed may be grown in combination with another strain which expresses the second part of the flocculation pair under inducible conditions. In such instances, inducing expression of the second part of the flocculation pair in the second strain would lead to flocculation.

Inducible regulatory elements may be used to control expression of a flocculation moiety. In such embodiments, the organism, for example a non-vascular photosynthetic organism, may be kept in culture without the expression of the flocculation moiety until flocculation is desired. Induction of expression may be performed by introducing an extrinsic factor (e.g., exposed to light, where a light-inducible promoter controls expression of the flocculation moiety) or by the occurrence of a factor necessary for expression (e.g., reaching a particular cell density where a quorum-sensing promoter controls expression of a flocculation moiety). Extrinsic factors which may be used to induce expression of a flocculation moiety include, but are not limited to, chemicals, light, culture density, temperature, hormones, or nutrients. Non-limiting examples of inducible promoters responding to cell extrinsic factors which may be utilized for the present invention include: the soybean Gmhsp17.3-B heat shock promoter (Prandl et al., *Plant Mol. Physiol.* 31:157-62, 2004); chemically inducible promoters (e.g., IPTG/lac promoter); phosphate/phosphate starvation inducible promoter (e.g., U.S. Pat. No. 6,175,060); L-arabinose/ara B promoter; 3-β-indoylacrylic acid/Tip promoter, salicylic acid/PR-1 promoter (e.g., U.S. Pat. No. 5,689,044); galactose inducible promoters such as GAL1, GAL7, GAL10 (U.S. Pat. No. 5,972,664); metal/metallothionine promoter; FUS1 promoter which is inducible by a pheromone (e.g., U.S. Pat. No. 5,063, 154); light inducible promoters (e.g., subunit of ribulose bisphosphate carboxylase promoter, see also U.S. Pat. No. 6,858,429); quorum sensing promoters, which sense cell density in a liquid environment and can be utilized to automatically induce flocculation as the culture reaches a certain density (e.g., Whiteley et al., *Journal of Bacteriology,* 183:529-5534, 2001); a temperature sensing promoter system utilizing $P_L$ promoter has also been described (see e.g., U.S. Pat. No. 4,711,845.). One of skill in the art will recognize that one or more endogenous regulatory elements may be utilized to control expression of a flocculation moiety by, for example, including an endogenous promoter in an expression cassette or inserting a nucleic acid encoding a flocculation moiety into a target genome such that it will be controlled by a native regulatory element (e.g., homologous recombination).

Another type of promoter includes nitrogen starvation induced promoters. Nitrogen starvation results in the formation of gametes in certain NVPOs, such as *C. reinhardtii*. By withdrawing nitrogen or by limiting the amount of available nitrogen, flocculation can be induced by rising nitrogen starvation responsive promoters to control expression of a flocculation moiety. Mating type agglutinins, which are naturally expressed by some NVPOs under nitrogen starvation conditions may be utilized, although not normally at levels which would yield flocculation in large culture. Thus, in one embodiment, increased production (e.g., through transformation of a host strain) of one or more agglutinins may yield flocculation.

Culture Conditions; Open Ponds and Closed Bioreactors

For many organisms, including non-vascular photosynthetic organisms (NVPOs), routine growth can occur at room temperature on 1.5% agar, either on plates or in tribes, while active growth is typically performed in liquid culture. Optimal growth is usually between 20-25° C., though the cells can survive exposure to 35° C. and may be grown at lower temperatures. Cell densities of $1-5\times10^6$ cells/ml are normal in liquid, with shaking or mixing, and a typical growth, rate may yield a tenfold increase in cells per day, depending on growth conditions. Long term storage of cells can be achieved by streaking them onto plates, sealing the plates with PARAFILM™ and placing them in dim light at 10-15° C. Alternatively, cells may be streaked or stabbed into agar tubes, capped and grown as above. Both methods allow storage for several months. For longer storage, the cells can be grown in liquid culture to late log phase and then made to 7% with sterile DMSO and stored at −80° C. Freezing the container in liquid nitrogen in the presence of methanol is also recommended for long term storage.

NVPOs can typically be grown on a simple defined medium with light as the sole energy source. In most cases fluorescent light bulbs at a distance of 1-2 feet are adequate to supply energy for growth. Bubbling with air or 5% $CO_2$ may improve the growth rate. If the lights are turned on and off at regular intervals (either 12:12 or 14:10 hours of light:dark) the cells of some NVPOs can be synchronized.

Because photosynthetic organisms such as algae require sunlight, $CO_2$ and water for growth, they can be cultivated in open ponds and lakes. Due to the fact that these are open system, they are much more vulnerable to being contaminated. One challenge with using open systems is that the NVPO of interest may not necessarily be the quickest to reproduce. This creates a problem where other species colonize the liquid environment. In addition, in open systems there is relatively less control over water temperature, $CO_2$ concentration and lighting conditions. These imply that the growing season is largely dependent on location and, aside from tropical areas, is limited to the warmer months. While the above are the disadvantages with "open systems", some of the benefits of this type of system are that it typically has lower production costs.

Another approach is to use a semi-closed system, such as covering the pond or pool with a greenhouse. While this usually results in a smaller system, it addresses many of the problems associated with an open system. It allows more species to be grown, it allows the species that are being grown to stay dominant, it extends the growing season, and if the greenhouse is heated, production can continue year round. It is also possible to increase the amount of $CO_2$ in these semi-closed systems, thus again increasing the rate of growth of algae.

A variation of the pond system is an artificial pond e.g., a raceway pond. In these ponds, the algae, water and nutrients circulate around a "racetrack." By providing water movement, for example by the use of paddlewheels, algae are kept suspended in the water, and are circulated back to the surface on a regular frequency. Raceway ponds are usually kept shallow because the algae need to be exposed to sunlight, and sunlight can only penetrate the pond water to a limited depth. However, depth can be varied according to the wavelength(s) utilized by an organism. The ponds can be operated in a continuous manner, with $CO_2$ and nutrients being constantly fed to the ponds, while algae-containing water is removed at the other end.

Alternatively, algae could be grown in closed structures such as photobioreactors, where the environment is under stricter control than in open ponds. While the costs of setting up and operating a photobioreactor would be higher than for those for open ponds, the efficiency and higher yields from these photobioreactors could be significantly higher as well, thus offsetting the initial cost disadvantage in the medium and long run.

A photobioreactor is a bioreactor that incorporates some type of light source. A pond covered with a greenhouse could also be considered a photobioreactor. Because these systems are closed everything that the algae need to grow, (carbon dioxide, water and light) need to be introduced into the system.

Photobioreactors can be set up to be continually harvested (the majority of the larger cultivation systems), or by harvesting a batch at a time (like polyethlyene bag cultivation). A batch photobioreactor is set up with nutrients and algal seed, and allowed to grow until the batch is harvested. A continuous photobioreactor is harvested either continually, as daily, or more frequently. Some types of photobioreactors include glass, plastic tubes, tanks, plastic sleeves or bags. Some sources that can be used to provide the light energy required to sustain photosynthesis include fluorescent bulbs LEDs, or natural sunlight.

Some of the organisms which may be used to practice the present invention are halophilic. For example, D. salina can grow in ocean water and salt lakes (salinity from 30-300 parts per thousand) and high salinity media (e.g., artificial seawater medium, seawater nutrient agar, brackish water medium, seawater medium, etc.). In some embodiments a host cell comprising a vector described herein can be grown in a liquid environment which is 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.3, 4.2, 4.3 molar or higher concentrations of sodium chloride. One of skill in the art will recognize that other salts (sodium salts, calcium salts, potassium salts, etc.) may also be present in the liquid environments.

Where a halophilic organism is utilized, it may be transformed with any of the vectors described herein. For example, D. salina may be transformed with a vector which is capable of insertion into the nuclear genome and which contains nucleic acids which encode a flocculation moiety (e.g., an anti-cell-surface-protein antibody, a carbohydrate binding protein, etc.). Transformed halophilic organisms may then be grown in high-saline environments (e.g., salt lakes, salt ponds, high-saline media, etc.) to produce the products (e.g., isoprenoids, fatty acids, biomass degrading enzymes, etc.) of interest. In some instances, the flocculation moiety may be non-functional under high salinity conditions. In such embodiments, flocculation may be induced by any of the methods described herein and/or by lowering the salinity (e.g, by diluting the liquid environment). Alternately, the flocculation moiety may be functional under high salinity conditions and flocculation may be controlled by any of the methods described herein. Flocculation of the organisms may take place under high salinity conditions, or the liquid environment may be diluted to a lower salinity to allow binding. Isolation of any products of interest produced by the organism may involve removing a transformed organism from a high-saline environment prior to extracting the product from the organism. In instances where the product is secreted into the surrounding environment, it may be necessary to desalinate the liquid environment prior to any further processing of the product Methods of Flocculation Provided herein are methods for flocculating a host organism. As discussed herein, flocculation moieties can be either extrinsic or intrinsic to a host organism. Extrinsic flocculation moieties may include recombinantly expressed and purified proteins, carbohydrates, or other biological molecules capable to binding the cell surface of an NVPO. Intrinsic flocculation moieties may include naturally occurring or recombinant proteins engineered to be expressed in the transformed NVPO, other biological material, such, as naturally occurring carbohydrates, lipids, or glycolipids produced at natural levels or that are produced in increased quantity due to genetic modification of the transformed. Thus, any method which allows for interaction, of at least two members of a flocculation pair may be utilized.

Figure 2:
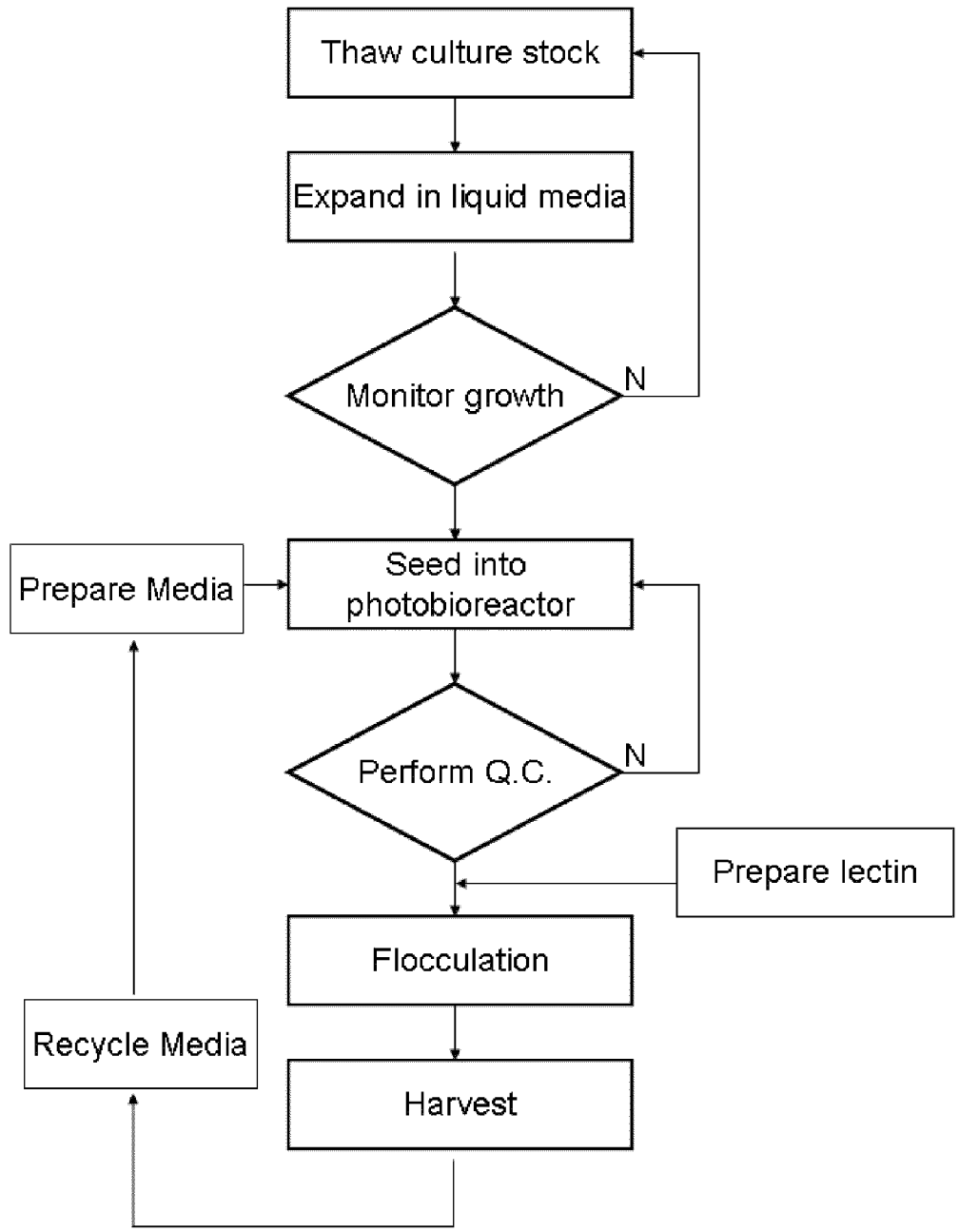
FIG. 2 is a flow chart of flocculation by lectin. Perform Q.C.; performing quality control of the large scale growth including growth rate, pH of the media, and screening for strain contamination. N; alternative work flow for conditions unsatisfactory to move forward to the next step.

For example, flocculation may be induced by adding one part of a flocculation pair which binds to an intrinsic flocculation moiety (e.g, a lectin binding to a cell wall glycoprotein). FIG. 2 provides an illustration of such an approach using a lectin. Certain, steps are not shown on the illustration for simplification. To start the culture, a strain of NVPO, such as C. reinhardtii, D. salina, D. tertiolecta, or H. pluvialis is obtained from culture stock. A culture stock can be an active liquid culture, or from a frozen stockpile. Once the culture stock is introduced into culture media, the culture is expanded in small scale laboratory equipment. At this time, the culture can be monitored for its growth characteristics, health, contamination, or other measurements typically performed for ensuring correct maintenance of NVPOs. Strain phenotyping and/or genotyping can also be done at this time to confirm the identity of the strain. Small scale cultures are used as a seed culture to large scale culture. Large scale culture can be conducted in a photobioreactor, semi-closed ponds, open ponds, or lakes (not shown in FIG. 2). Multiple batches of small scale culture can be seeded into one large-scale culture vessel. The ratio of seeding volume to receiving volume can be determined at the time of seeding according to parameters such as optical density and growth rate of the small scale culture(s). In preparation of media for the large scale culture, autoclaving, adding nutrients to recycled media, evaluating the condition of recycled media, and measuring the pH, salt, and conductivity of the media can be performed. During the large scale culture, quality control is performed. Quality control criteria may include sampling and screening for contamination, strain divergence, growth kinetics, oxygen level, nitrogen level, salinity of the liquid, pH of the liquid media, sampling of growing cells for oil content measurement, dry weight/wet weight ratio, and optical density of the culture. In one exemplary embodiment, when flocculation is deemed appropriate, lectin is added. Lectin can be purchased, or prepared in-house. Producing recombinant lectin is known in the art. For example, methods and compositions to produce lectin in microorganisms have been described in U.S. Pat. No. 4,870,015. Recombinantly expressed lectin can be purified to homogeneity and then be added to NVPO culture to promote flocculation. In some instances, the NVPO in culture may express a naturally occurring flocculation moiety to which the lectin binds, or may be genetically modified to produce increased levels of a naturally occurring flocculation moiety or may be genetically modified to produce an exogenous flocculation moiety. Flocculants other than lectin (not shown in FIG. 2) can also be employed as a lone flocculant or in conjunction with lectin. After flocculation, the flocculated cellular mass of the NVPO is harvested. Any of a variety of harvesting methods known in the art can be employed, ranging from sieving with a filter to a sophisticated robotic system to collect, squeeze, and compact the flocculated NVPO mass.

Figure 3:
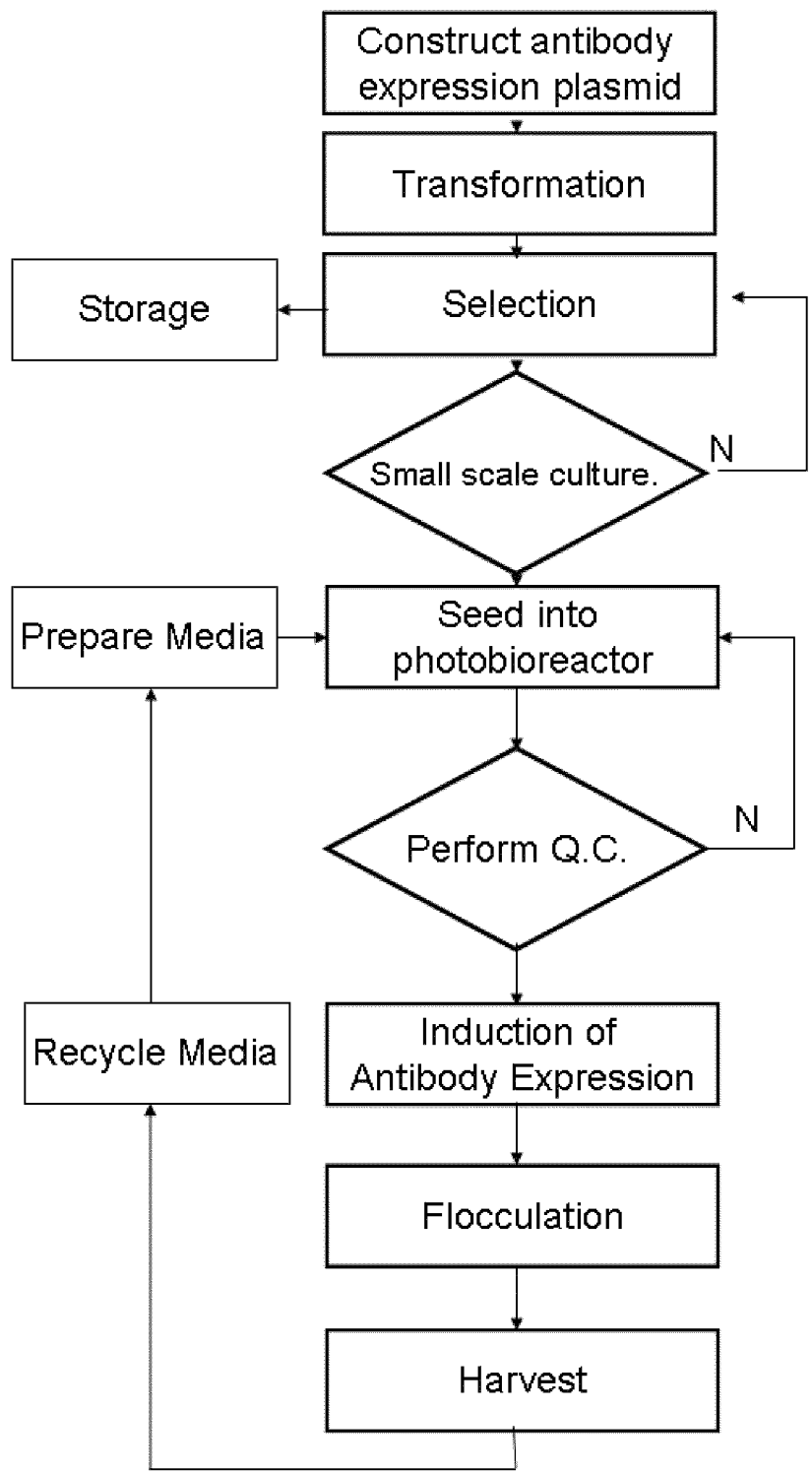
FIG. 3 is a flow chart of flocculation induced by an anti-Fus1 antibody.

An alternate approach is shown in FIG. 3. Certain steps are not shown on the illustration for simplification. The process presented involves use of a genetically modified organism (e.g, an NVPO) expressing one or more flocculation moieties. In FIG. 3, the flocculation moiety is an antibody, for example a single chain variable fragment (scFv) antibody. Antibodies other than an scFv antibody can be applied to the method of flocculation illustrated in FIG. 3. Also not shown but applicable to the illustrated steps of FIG. 3 are flocculation moieties that can be polymerized. For example, an actin monomer can form an actin polymer. An expression cassette encoding an antibody is constructed and incorporated into a targeting vector appropriate for nuclear genome targeting. The expression cassette contains a regulatory element which allows the expression of the antibody. The regulatory element can be a constitutively active element which allows the antibody transcripts are made constantly in the cell. The regulatory element can be an inducible element which requires an extrinsic signal to start the transcription of the antibody. The organism is transformed using appropriate procedures. Correctly targeted cells are selected by molecular biology techniques known in the art, such as polymerase chain reaction or screening on a selectable antibiotic medium. A portion of selected cells are cryopreserved while the rest are used for starting small scale liquid culture for example as described in FIG. 2. When flocculation is deemed appropriate, expression of flocculation moiety is induced by providing the extrinsic induction signal. Flocculation can be incremental depending on the amount or intensity of the extrinsic induction signal. Degree of flocculation can be tied to cell density if constitutively active element is employed to express the flocculation moiety. After flocculation, the flocculated mass of NVPO is harvested. Any of a variety of harvesting methods known in the art can be employed, ranging from simple sieving technology with a filter to a sophisticated robotic system to collect, squeeze, and compact the flocculated NVPO mass.

In other instances, one part of the flocculation pair may be secreted by a genetically modified host cell and induce flocculation upon binding to the second part of the flocculation pair present on that cell or another cell. In still other instances, one member of a flocculation pair may be attached to a solid phase (e.g., a bead, a mesh, a sieve), to induce flocculation of a host strain expressing the other member of the flocculation pair.

Figure 4:
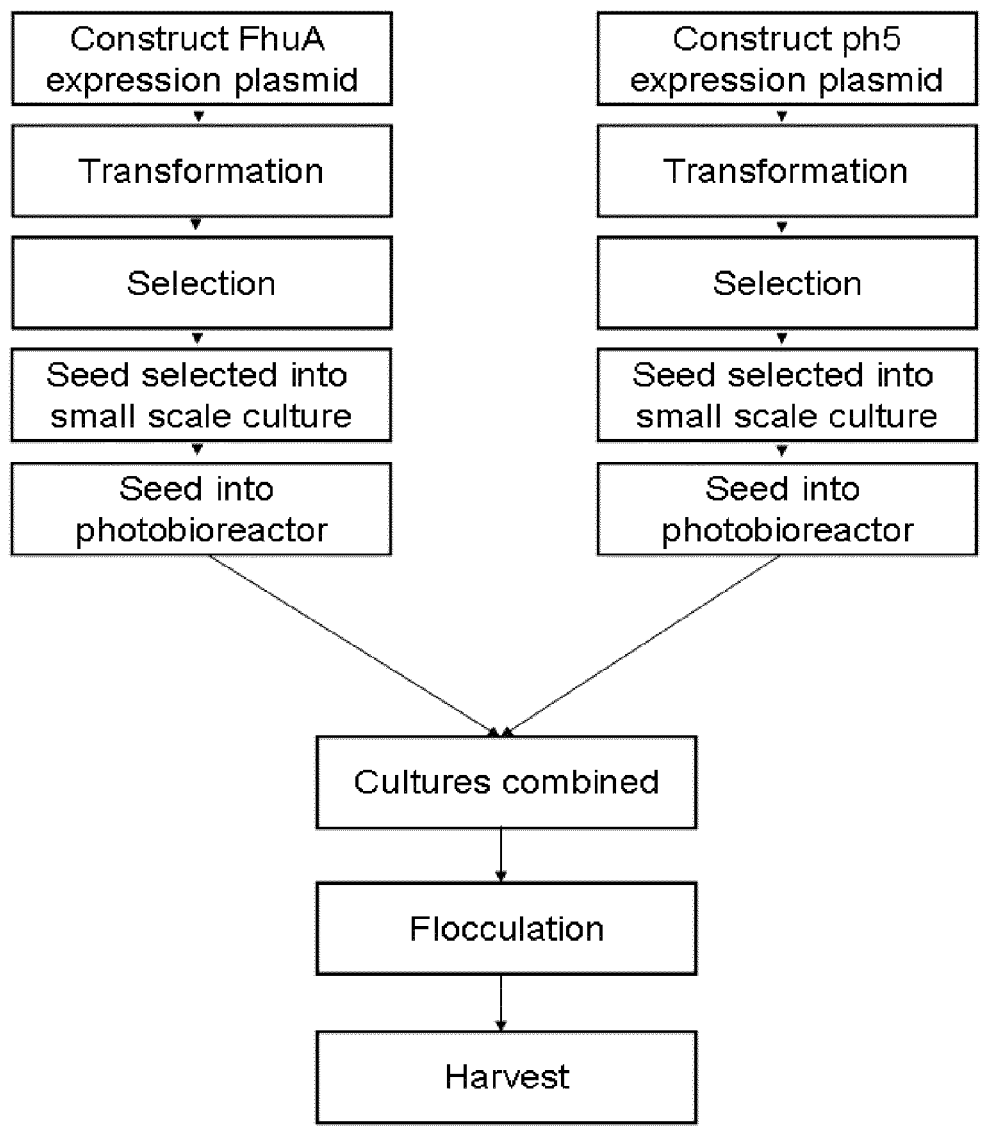
FIG. 4 is a flow chart of flocculation induced by the expression of FhuA and pb5.

Flocculation may be induced by combining, separately grown cultures in any ratio ranging from 1:1 to 1:10 where the different cultures each express one part of a flocculation pair (two-part binding complex) or flocculation complex (three-or-more-part binding complex). A generalized approach is shown in FIG. 4. Certain steps are not shown for simplification. In FIG. 4, the flocculation pair is FhuA and pb5, expressed on separately grown strains and flocculation is induced by combining the strains. In this scheme, the flocculation moieties are not capable of self-recognition or self-polymerization. To flocculate, as illustrated, these flocculation moieties require the presence of each other. Other flocculation moieties that form a pair or a complex can also be applied to the scheme illustrated in FIG. 4. The construction of expression cassette, introduction of regulatory element, incorporation into a suitable vector, transformation, selection, small to large-scale culture steps or other inventive steps are described, supra.

Flocculation may be induced by inducibly regulating expression of one member of a flocculation pair, for example by: 1) exposing a culture from dark to light where a flocculation moiety is controlled by an inducible regulatory element; 2) increasing the culture temperature to about 26° C., 27° C., 28° C., 29° C., 30° C., 31° C., 32° C., 34° C., 35° C., 36° C., 37° C., 39° C., 40° C., 41° C., 42° C., or 43° C. for a brief period of time ranging from several seconds to several minutes to a few hours; 3) increasing the culture density to about $5 \times 10^6$, $6 \times 10^6$, $7 \times 10^6$, $8 \times 10^6$, $9 \times 10^6$, $1 \times 10^7$, $2 \times 10^7$, $3 \times 10^7$, $4 \times 10^7$, $5 \times 10^7$, $6 \times 10^7$, $7 \times 10^7$, $8 \times 10^7$, $9 \times 10^7$, $1 \times 10^8$, $2 \times 10^8$, $3 \times 10^8$, $4 \times 10^8$, $5 \times 10^8$, $6 \times 10^8$, $7 \times 10^8$, $8 \times 10^8$, $9 \times 10^8$, $1 \times 10^9$, $2 \times 10^9$, $3 \times 10^9$, $4 \times 10^9$, $5 \times 10^9$, $6 \times 10^9$, $7 \times 10^9$, $8 \times 10^9$, $9 \times 10^9$, $1 \times 10^{10}$, $2 \times 10^{10}$, $3 \times 10^{10}$, $4 \times 10^{10}$, $5 \times 10^{10}$, $6 \times 10^{10}$, $7 \times 10^{10}$, $8 \times 10^{10}$, $9 \times 10^{10}$ or more cells/ml; 4) adding nitrogen, for example in the form of nitrate, to the culture for about 15 min, 30 min, 45 min, 60 min, 75 min, 90 min, 105 min, 120 min, 135 min, 150 min, 165 min, 180 min, 195 min, 210 min, 225 min, 240 min, 255 min, 270 min, 285 min, 300 min, 315 min, 330 min, 345 min, 360 min, 375 min, 390 min, 405 min, 420 min, 435 min, 450 min, 465 min, 480 min, 495 min, 510 min, 525 min, 540 min, 555 min, 570 min, 585 min, 600 min, 12 hours, 18 hours, 24 hours 36 hours, 24 hours or more; and/or 5) depriving nitrogen from the culture media for about 15 min, 30 min, 45 min, 60 min, 75 min, 90 min, 105 min, 120 min, 135 min, 150 min, 165 min, 180 min, 195 min, 210 min, 225 min, 240 min, 255 min, 270 min, 285 min, 300 min, 315 min, 330 min, 345 min, 360 min, 375 min, 390 min, 405 min, 420 min, 435 min, 450 min, 465 min, 480 min, 495 min, 510 min, 525 min, 540 min, 555 min, 570 min, 585 min, 600 min, 12 hours, 18 hours, 24 hours 36 hours, 24 hours or more.

Figure 5:
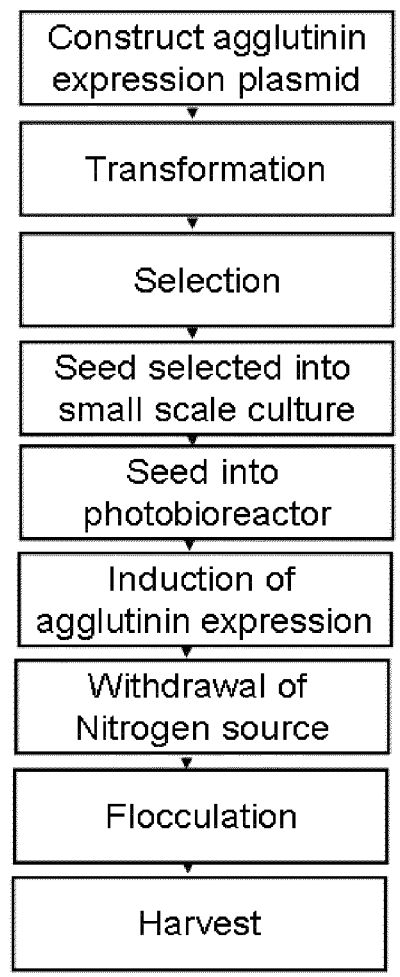
FIG. 5 is a flow chart of flocculation induced by genes regulated by nitrogen starvation in genetically modified *Chlamydomonas reinhardtii*.

An example of growing two strains in the same culture where both parts of a flocculation pair are inducibly controlled is shown in FIG. 5. Certain steps are not shown on the illustration for simplification. In FIG. 5, the flocculation pair comprises both, mating type agglutinins. In this figure, two strains of *C. reinhardtii* are genetically modified to express increased levels of mating type agglutinin (e.g., each, strain produces one member of the flocculation pair), but under the control of the naturally occurring nitrogen-starvation responsive elements. In transformed NVPO, expressed agglutinin is targeted to broader area of cell body than to flagella to promote efficient flocculation. Targeting of agglutinin is achieved by inserting DNA sequences encoding cell wall-targeting signal peptide in the expression cassette. Induction of agglutinin is promoted by depletion of nitrogen in the culture media as the cultures grow. Optimal timing for flocculation can be altered by increasing or decreasing the amount of nitrogen. Upon reaching nitrogen starvation, the two strains will begin to increase production of their individual flocculation moiety and flocculation will occur.

Recycling of Media

One advantage of the use of engineered and/or naturally expressed flocculation moieties, as disclosed herein, is the recycling of the liquid environment. The recycling of media (e.g., laboratory media, pond water, lake water, bioreactor contents, etc.) is economically advantageous, especially in large scale operations. For example, in a controlled circulating pond system, the liquid environment can be recycled by allowing continuous flow of the liquid while nutrients are continuously added. In another embodiment, in a closed photobioreactor system, media recycling may comprise scooping out flocculated NVPO mass; measuring the pH of the media; measuring the level of each nutrient in the liquid; adjusting nutrients to optimal level; sterilizing the liquid by autoclaving; and/or returning the media for new culture.

It is to be understood that the terminology used herein is for the purpose of describing particular embodiments only and is not intended to be limiting. Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, specific examples of appropriate materials and methods are described herein.

As used in this specification and the appended claims, the singular forms "a", "an" and "the" are to be construed to cover both singular and plural referents unless the content or context clearly dictates otherwise. Thus, for example, reference to "polypeptide" includes two or more such polypeptides. The terms "comprising," "having," "including," and "containing" are to be construed as open-ended terms (i.e., meaning "including, but not limited to,") unless otherwise noted.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention. The headings provided in the description of the invention are included merely for convenience and are not intended to be limiting in the scope of the disclosure.

Generally, the nomenclature used herein and the laboratory procedures in cell culture, molecular genetics, molecular biology, nucleic acid chemistry, and protein chemistry described below are those well known and commonly employed by those of ordinary skill in the art. In accordance with the present invention, common recombinant DNA techniques, molecular biology techniques, molecular genetics, and microbiology techniques may be used by one of skill in the art. For example, techniques such as those described in Sambrook, Goeddel, supra, and CURRENT PROTOCOLS IN MOLECULAR BIOLOGY, F. M. Ausubel et al., eds., Current Protocols, a joint venture between Greene Publishing Associates, Inc. and John Wiley & Sons, Inc. (1994, supplemented through 1999) (hereinafter "Ausubel"), DNA CLONING: A PRACTICAL APPROACH, Vols. I-II (Glover ed. 1985); Animal Cell Culture (Freshney ed. 1986) may be used for recombinant nucleic acid methods, nucleic acid synthesis, cloning methods, cell culture methods, transfection and transformation, and transgene incorporation, e.g., electroporation, injection, gene gun, impressing through the skin, and lipofection. Generally, oligonucleotide synthesis and purification steps are performed according to specifications. The techniques and procedures are generally performed according to conventional methods in the art and various general references that are provided throughout this document. The procedures therein are believed to be well known to those of ordinary skill in the art and are provided for the convenience of the reader.

While certain embodiments have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments described herein may be employed in practicing the invention. It is intended that the following claims define the scope of the invention and that methods and structures within the scope of these claims and their equivalents be covered thereby.

EXAMPLES

Example 1

Production of Recombinant Lectins in *E. coli*

Nucleic acids encoding lectins were introduced into *E. coli*. Transforming DNA is shown graphically in FIG. 1A. In this instance, the segment labeled "Transgene 1" is the gene encoding the lectins from *H. pomatia*, (SEQ ID NO: 1) *L. culinaris, T. vulgaris*, (SEQ ID NO: 2) or *C. ensiformis*. The segment labeled "5'UTR" is the T7 promoter and the segment labeled "3'UTR" is the T7 terminator. A metal affinity tag (MAT), Tobacco etch virus (TEV) protease cleavage site, and a Flag epitope are engineered on the 3' end of the gene to facilitate characterization and visualization studies. All DNA manipulations carried out in the construction of this transforming DNA were essentially as described by Sambrook et al. Molecular Cloning: A Laboratory Manual (Cold Spring Harbor Laboratory Press 1989) and Cohen et al., *Meth. Enzymol.* 297, 192-208, 1998.

The transforming DNA was introduced into BL21(DE3) pLysS competent cells (Invitrogen) according to the manufacturer's instructions. Briefly, colonies were lysed by Bug-Buster Protein Extraction Reagent (Novagen) and MAT-tagged proteins were separated using MagneHis Ni-particles (Promega), according to the manufacturer's instructions. Colonies were cultured in 5 mL of Luria Broth (LB) in the presence of 50 μg/mL kanamycin. 100 μL of the culture at $O.D._{600}$=1 was centrifuged and the supernatant was removed. The pellets were lysed by resuspending the cells in 50 μl of 1×SDS sample buffer with reducing agent (BioRad). Samples were then boiled and run on a 10% Bis-tris polyacrylamide gel (BioRad) and transferred to PVDF membranes using a Trans-blot semi-dry blotter (BioRad) according to the manufacturer's instructions. Membranes were blocked by Starting Block (TBS) blocking buffer (Thermo Scientific) and probed for one hour with mouse anti-FLAG antibody-horseradish peroxidase conjugate (Sigma) diluted 1:3000 in Starting Block buffer. After probing, membranes were washed four times with TBST, then developed with Supersignal West Dura chemiluminescent substrate (Thermo Scientific) and imaged using a CCD camera (Alpha Innotech).

Figure 6:
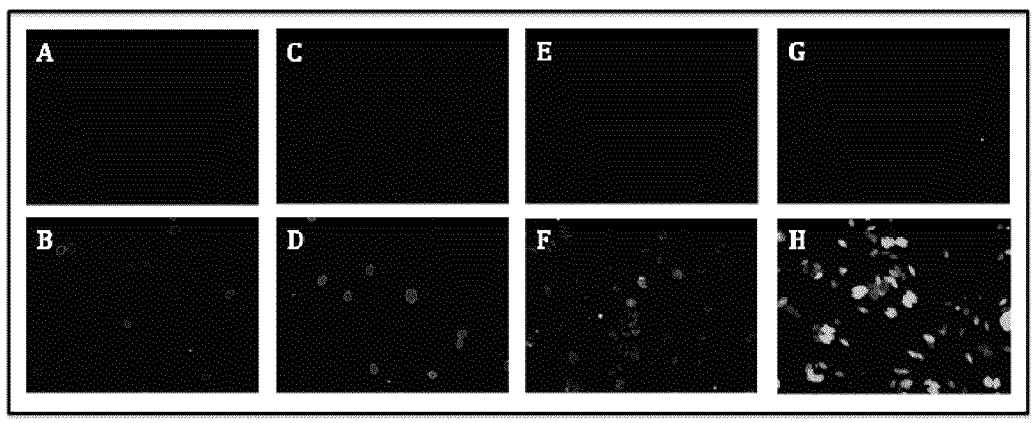
FIG. 6 shows the activity of recombinant lectins produced in *E. coli*. A-D are *Chlamydomonas reinhardtii* where A and C are negative controls and B and D are in the presence of FITC-conjugated lectins from *H. pomatia* and *T. vulgaris*, respectively, E-H is *Scenedesmus dimorphus* where E and G are negative controls and F and H are in the presence of FITC-conjugated lectins from *H. pomatia* and *T. vulgaris*, respectively.
Figure 7:
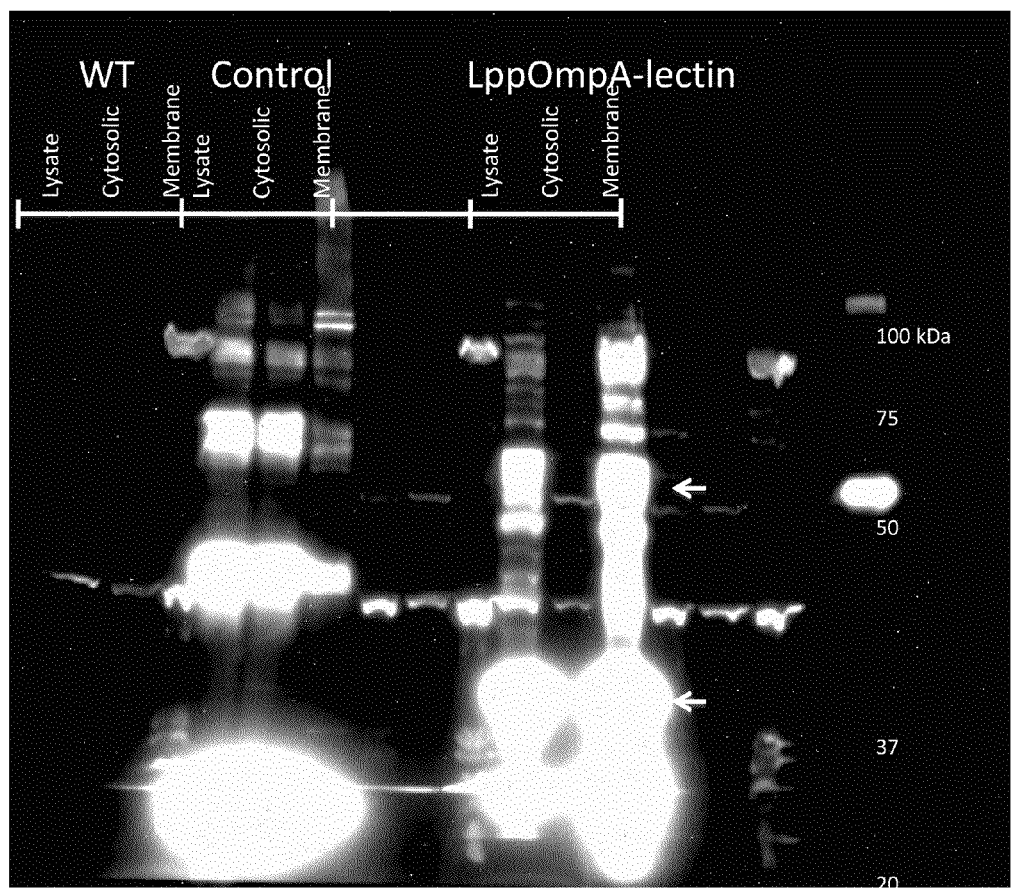
FIG. 7 shows the insertion of a LppOmpA-lectin fusion protein in the cell membrane of *E. coli*.

To determine the activity of the recombinant lectins, 4 L of each strain were grown and harvested by centrifugation at 5000×g for 15 minutes. All subsequent manipulations are performed at 4° C. and in the presence of protease inhibitors. The pellet was resuspended in 35 mL 1×Tris Buffered Saline (TBS) and sonicated at 30% power using a macrotip for 3 cycles of 30 seconds. The solution was then centrifuged at 30,000×g for 30 minutes to remove the unlysed cells. The supernatant was transferred and 1 mL Ni-NTA resin (Qiagen) applied for 1 hour. The resin was collected, washed with 30 column volumes of 1×Tris Buffered Saline (TBS) and eluted with 5 mL TBS and 400 mM imidazole pH 7.5. The eluate was then concentrated to a final concentration of 5 mg/mL using Amicon Ultra-15 Centrifugal Filter Units (Millipore). Purified protein was then conjugated to FITC (fluorescein isothiocyanate) using a FITC labeling kit (Thermo Scientific) according to She manufacturer's instructions. *Chlamydomonas reinhardtii* and *Scenedesmus dimorphus* cells were then mixed with the FITC labeled protein to show activity. Results from several representative lectins are shown in FIG. 6.

Example 2

Production of Scaffold-Lectin Fusions in *E. coli*

Nucleic acids encoding lectins from *H. pomatia* and *L. culinaris* were fused to scaffold proteins lipoprotein-outer membrane protein A hybrid (Lpp-OmpA) or the β-autotransporter from *Neisseria gonorrhoea* (SEQ ID NO: 3; SEQ ID NO: 4; SEQ ID NO: 5) and introduced into *E. coli*. Transforming DNA is shown graphically in FIG. 1B. In this instance the segment labeled "Transgene 1" is the gene encoding the lectin from *H. pomatia*. The segment labeled "Transgene 2" is the gene encoding the lectin from *L. culinaris*. The segment, labeled "5'UTR" is the T7 promoter, the segment labeled "3'UTR" is the T7 terminator, the segment labeled "Scaffold 1" is Lpp-OmpA, and the segment labeled "Scaffold 2" is the β-autotransporter. A metal affinity tag (MAT) Tobacco etch virus (TEV) protease cleavage site, and a Flag epitope were engineered between the transgene and the scaffold. All DNA manipulations carried out in the construction of this transforming DNA were essentially as described by Sambrook et al., Molecular Cloning: A Laboratory Manual (Cold Spring Harbor Laboratory Press 1989) and Cohen et al., *Meth. Enzymol.* 297, 192-208, 1998.

The transforming DNA was introduced into BL21(DE3) pLysS competent cells (Invitrogen) according to the manufacturer's instructions. Briefly, colonies were lysed by Bug-Buster Protein Extraction Reagent (Novagen) and MAT-tagged proteins were separated using MagneHis Ni-particles (Promega), according to manufacturer's instructions. Colonies were cultured in 5 mL of Luria Broth (LB) in the presence of 50 μg/mL kanamycin, 100 μL of the culture at $O.D._{600}$=1 was centrifuged and the supernatant was removed. The pellets were lysed by resuspending cells in 50 μl of 1×SDS sample buffer with reducing agent (BioRad). Samples were then boiled and run on a 10% Bis-tris polyacrylamide gel (BioRad) and transferred to PVDF membranes using a Trans-blot semi-dry blotter (BioRad) according to the manufacturer's instructions. Membranes were blocked by Starting Block (TBS) blocking buffer (Thermo Scientific) and probed for one hour with mouse anti-FLAG antibody-horseradish peroxidase conjugate (Sigma) diluted 1:3000 in Starting Block buffer. After probing, membranes were washed four times with TBST, then developed with Supersignal West Dura chemiluminescent substrate (Thermo Scientific) and imaged using a CCD camera (Alpha Innotech).

Figure 8:
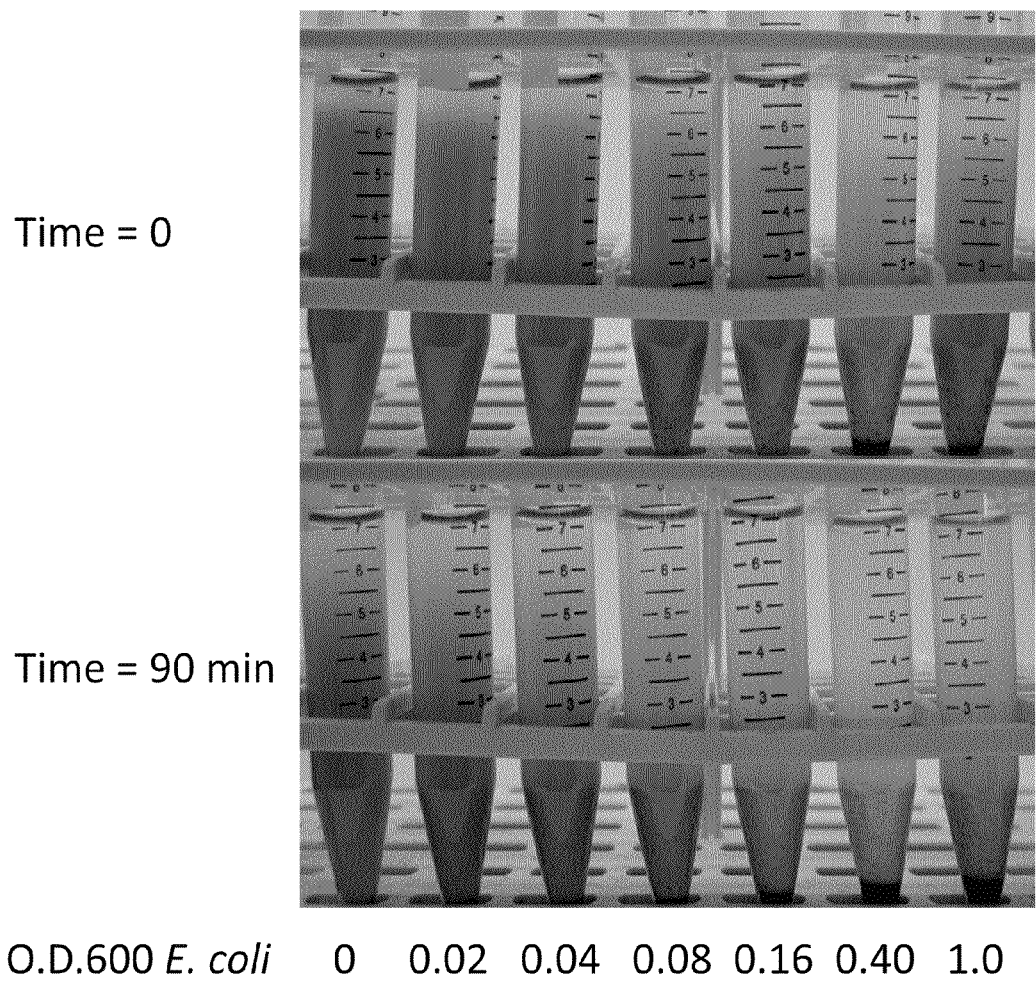
FIG. 8 shows the effect of β-autotransporter *L. culinaris* lectin fusion protein on sedimentation of *S. dimorphus*.

To determine whether the lectin-scaffold fusion is properly inserted in the plasma membrane, membrane isolations were performed. 25 mLs of a culture of at $O.D._{600}$=1 were centrifuged at 5000×g for 10 minutes. All subsequent manipulations were performed at 4° C. and in the presence of protease inhibitors. The pellet was resuspended in 3 mL 1×Tris Buffered Saline (TBS) and sonicated at 30% power using a macrotip for 3 cycles of 10 seconds. The solution was then centrifuged at 30,000×g for 30 minutes to removed the unlysed cells. 1 mL of the supernatant (mixture of membranes and cytosolic proteins) was carefully removed and centrifuged at 540,000×g in a TLA100.3 rotor (Beckman) for 20 minutes to separate the insoluble (membranes) from the soluble (cytosolic proteins). Samples were then boiled and run on a 10% Bis-tris polyacrylamide gel (BioRad) and transferred to PVDF membranes using a Trans-blot semi-dry blotter (BioRad) according to the manufacturer's instructions. Membranes were blocked by Starting Block (TBS) blocking buffer (Thermo Scientific) and probed for one hour with mouse anti-FLAG antibody-horseradish peroxidase conjugate (Sigma) diluted 1:3000 in Starting Block buffer. After probing, membranes were washed four times with TBST, then developed with Supersignal West Dura chemiluminescent substrate (Thermo Scientific) and imaged using a CCD camera (Alpha Innotech). Results are shown in FIG. 8.

In order to characterize the activity of the cell surface displayed sugar-binding protein, sedimentation experiments were employed. The E. coli transformed to produce a fusion protein composed of the lectin from L. culinaris and the scaffold protein β-autotransporter was grown to an $O.D._{600}=1.6$. The culture was centrifuged and the pellet was resuspended to an $O.D._{600}=30$ using TAP media. Varying amounts of culture (0 uL, 5 uL, 10 uL, 20 uL, 40 uL, 100 uL, 250 uL, and 500 uL corresponding to a final $O.D._{600}=0, 0.02, 0.04, 0.08, 0.160, 0.400, 1.00, 2.00$) were added to 7 mL of S. dimorphus grown in TAP media. 500 uL of BL21(DE3) was added to 7 mL of S. dimorphus as a negative control. The mixtures were shaken gently for 30 minutes before settling. Photos (FIG. 8) were taken at time points 0 and 90 minutes to visualize the activity.

Example 3

Production of Scaffold-scFv Fusions in E. coli

A single chain variable fragment (scFv) antibody to algal surface antigens were fused to scaffold proteins lipoprotein-outer membrane protein A hybrid (Lpp-OmpA) introduced into E. coli (SEQ ID NO. 16). Transforming DNA is shown graphically in FIG. 1C. In this instance the segment labeled "Transgene 1" is the gene encoding scFv5. The segment labeled "5'UTR" is the T7 promoter, the segment labeled "3'UTR" is the T7 terminator, the segment labeled "Scaffold 1." is Lpp-OmpA. A metal affinity tag (MAT), Tobacco etch virus (TEV) protease cleavage site, and a Flag epitope were engineered between the scaffold and the transgene. All DNA manipulations carried out in the construction of this transforming DNA were essentially as described by Sambrook et al., Molecular Cloning: A Laboratory Manual (Cold Spring Harbor Laboratory Press 1989) and Cohen et al., *Meth. Enzymol.* 297, 192-208, 1998.

The transforming DNA was introduced into BL21(DE3) pLysS competent cells (Invitrogen) according to the manufacturer's instructions. Briefly, colonies were lysed by Bug-Buster Protein Extraction Reagent (Novagen) and MAT-tagged proteins were separated using MagneHis Ni-particles (Promega), according to manufacturer's instructions. Colonies were cultured in 5 mL of Luria Broth (LB) in the presence of 50 μg/mL Kanamycin. 100 μL of the culture at $O.D._{600}=1$ was centrifuged and the supernatant was removed. The pellets were lysed by resuspending cells in 50 μl of 1×SDS sample buffer with reducing agent (BioRad). Samples were then boiled and ran on a 10% Bis-tris polyacrylamide gel (BioRad) and transferred to PVDF membranes using a Trans-blot semi-dry blotter (BioRad) according to the manufacturer's instructions. Membranes were blocked by Starting Block (TBS) blocking buffer (Thermo Scientific) and probed for one hour with mouse anti-FLAG antibody-horseradish peroxidase conjugate (Sigma) diluted 1:3000 in Starting Block buffer. After probing, membranes were washed four times with TBST, then developed with Supersignal West Dura chemiluminescent substrate (Thermo Scientific) and imaged using a CCD camera (Alpha Innotech).

Figure 9:
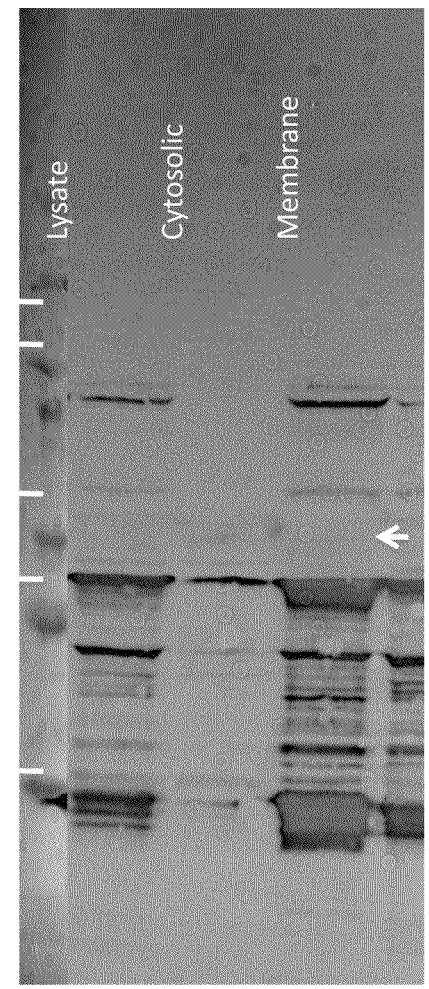
FIG. 9 shows a western blot showing proper insertion of a LppOmpA-scFv5 fusion in the plasma membrane of *E. coli*.

To determine whether the LppOmpA-scFv fusion is properly inserted in the plasma membrane, membrane isolations were performed. 25 mLs of a culture of at $O.D._{600}=1$ were centrifuged at 5000×g for 10 minutes. All subsequent manipulations were performed at 4° C. and in the presence of protease inhibitors. The pellet was resuspended in 3 mL 1×Tris Buffered Saline (TBS) and sonicated at 30% power using a macrotip for 3 cycles of 10 seconds. The solution was then centrifuged at 30,000×g for 30 minutes to remove the unlysed cells. 1 mL of the supernatant (mixture of membranes and cytosolic proteins) was carefully removed and centrifuged at 540,000×g in a TLA100.3 rotor (Beckman) for 20 minutes to separate the insoluble (membranes) from the soluble (cytosolic proteins). Samples were then boiled and run on a 10% Bis-tris polyacrylamide gel (BioRad) and transferred to PVDF membranes using a Trans-blot semi-dry blotter (BioRad) according to the manufacturer's instructions. Membranes were blocked by Starting Block (TBS) blocking buffer (Thermo Scientific) and probed for one hour with mouse anti-FLAG antibody-horseradish peroxidase conjugate (Sigma) diluted 1:3000 in Starting Block buffer. After probing, membranes were washed four times with TBST, then developed with Supersignal West Dura chemiluminescent substrate (Thermo Scientific) and imaged using a CCD camera (Alpha Innotech), Results from a representative fusion, construct LppOmpA-scFv5 are shown in FIG. 9.

Example 4

Production of Secreted, Recombinant Lectins in P. pastoris

Nucleic acids encoding lectins such as those from H. pomatia, L. culinaris, T. vulgaris and C. ensiformis can be introduced into P. pastoris. Transforming DNA is shown graphically in FIG. 1A. In this instance the segment labeled "Transgene 3" is the gene encoding the lectins from H. pomatia, (SEQ ID NO: 1) L. or vulgaris, (SEQ ID NO: 2). The segment labeled "5'UTR" is the AOX1 promoter and the segment labeled "3'UTR" is the AOX1 terminator. A metal affinity tag (MAT), Tobacco etch virus (TEV) protease cleavage site, and a Flag epitope are engineered on the 3' end of the gene to facilitate characterization and visualization studies. All DNA manipulations were carried out in the construction of this transforming DNA were essentially as described by Sambrook et al., Molecular Cloning: A Laboratory Manual (Cold Spring Harbor Laboratory Press 1989) and Cohen et al., *Meth. Enzymol.* 297, 192-208, 1998.

Figure 10:
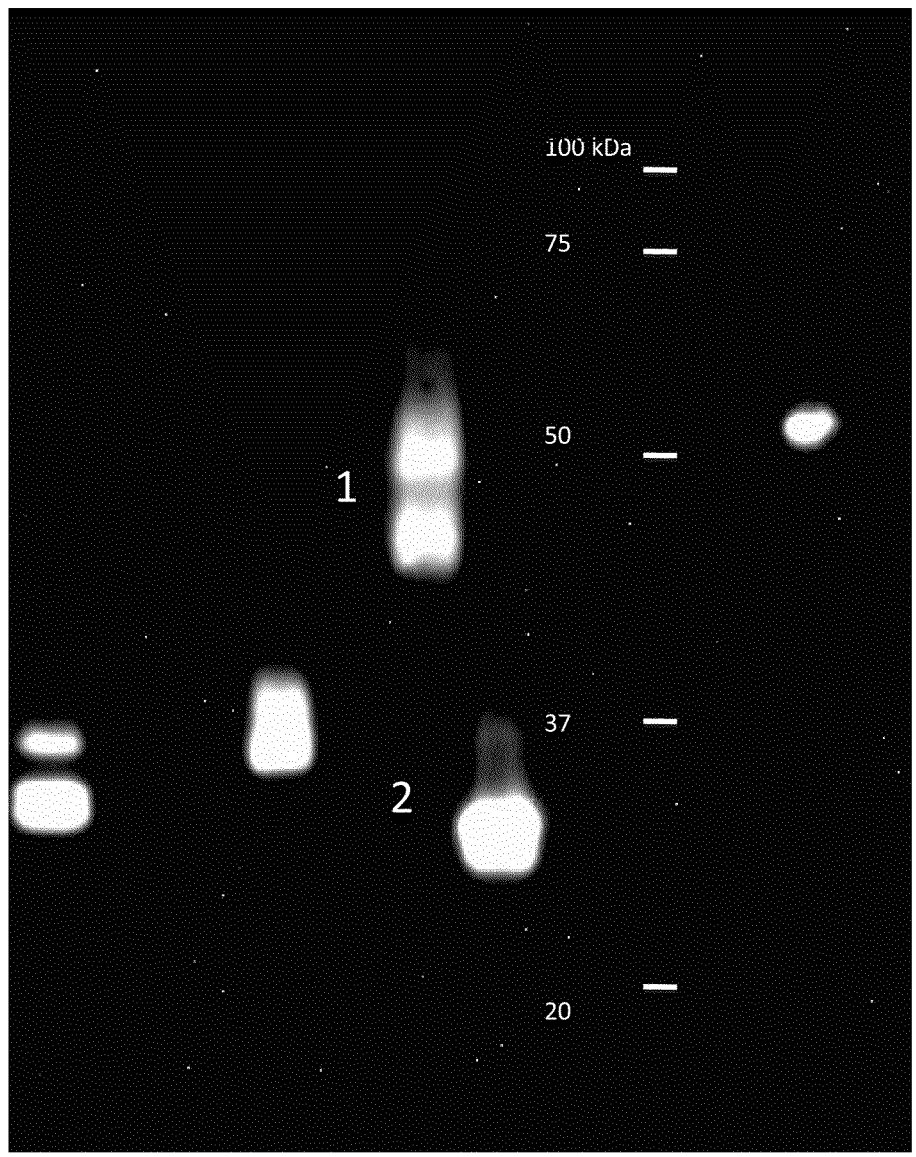
FIG. 10 shows a western blot of secreted lectins in *Pichia pastoris*. Representative examples labeled 1 (*H. pomatia* lectin) and 2 (*L. culinaris* lectin) show protein secretion into the growth medium

The transforming DNA was cloned into the pPIC9K vector (Invitrogen), thereby introducing the alpha-factor signal peptide at the 5' end to facilitate secretion, and was introduced into GS115 competent cells (Invitrogen) according to the manufacturer's instructions. To determine whether the recombinant lectins are expressed, 1 L of each strain was grown centrifuged at 5000×g for 15 minutes. All subsequent manipulations were performed at 4° C. and in the presence of protease inhibitors. 1 mL Ni-NTA resin (Qiagen) was applied to the spent media for 1 hour. The resin was collected, washed with 30 column volumes of 1×Tris Buffered Saline (TBS) and eluted with 5 mL TBS and 400 mM imidazole pH 7.5. The eluate was then concentrated to a final concentration of 5 mg/mL using Amicon Ultra-15 Centrifugal Filter Units (Millipore). Representative lectins secreted by P. pastoris are labeled and shown in FIG. 10.

Example 5

Production of Scaffold-Lectin Fusions in P. pastoris

Nucleic acids encoding lectins from H. pomatia, L. culinaris, and T. vulgaris were fused to scaffold proteins such as the *S. cerevisiae* Pir1a, (SEQ ID NO: 6; SEQ ID NO: 7) Pir1b (SEQ ID NO: 8), the floccolin Flo1p, and the agglutinin protein Aga1p. All fusions, except those with Flo1p, are an N-terminal fusion placing the lectin 5' of the scaffold. A metal affinity Sag (MAT), Tobacco etch virus (TEV) protease cleavage site, and a Flag epitope were engineered in the linker between She two genes to facilitate characterization and visualization studies. Transforming DNA is shown graphically in FIG. 1B. In this example, the segment labeled "Transgene 1" is the gene encoding the lectin from *H. pomatia*. The segment labeled "Transgene 2" is the gene encoding the lectin from *L. culinaris*. The segment labeled "5'UTR" is the AOX1 promoter, the segment labeled "3'UTR" is the AOX1 terminator, the segment labeled "Scaffold 1" is Pir1a, Pir1b, or Aga1p, and the segment labeled "Scaffold 2" is the Flo1p. All DNA manipulations carried out in the construction of this transforming DNA were essentially as described by Sambrook et al., Molecular Cloning: A Laboratory Manual (Cold Spring Harbor Laboratory Press 1989) and Cohen et al., *Meth. Enzymol.* 297, 192-208, 1998.

Figure 11:
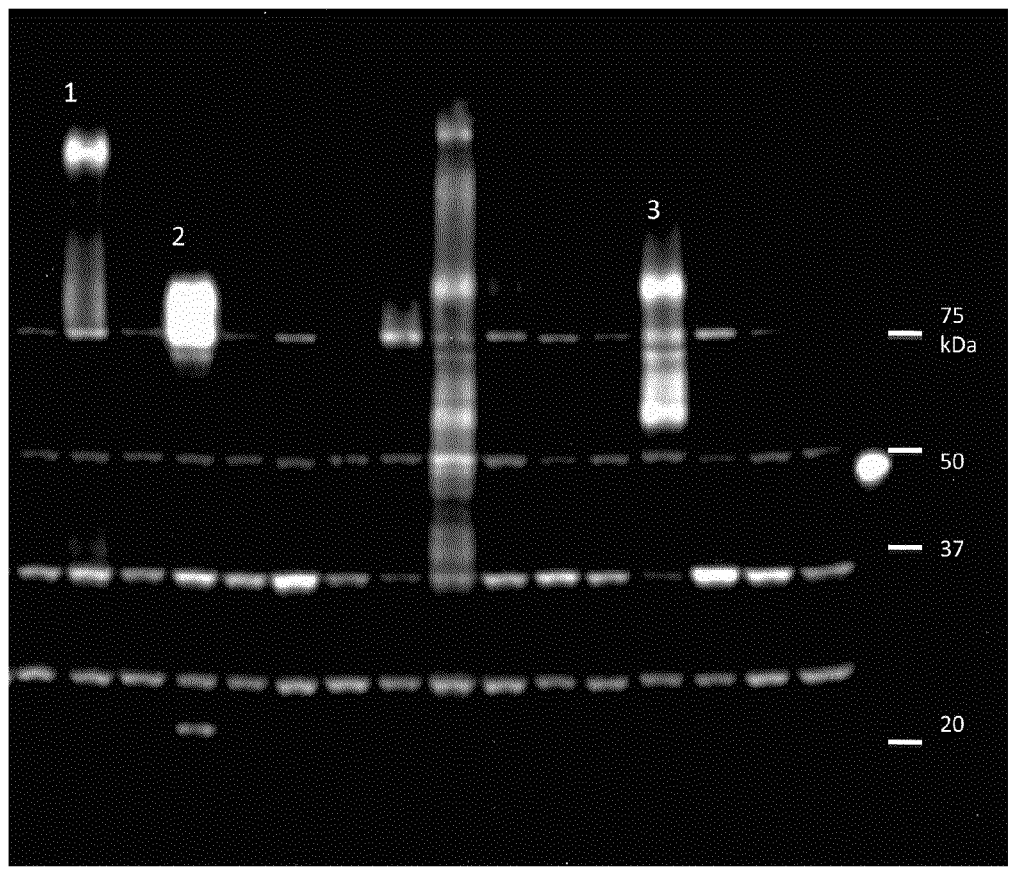
FIG. 11 shows the expression of scaffold lectin fusion proteins in *P. pastoris*: (1) Pir1b-*H. pomatia* lectin, (2) Pir1b-*L. culinaris* lectin, and (3) Pir1a-*T. vulgaris* lectin.

The transforming DNA was cloned into the pPIC9K vector (Invitrogen), thereby introducing the alpha-factor signal peptide at the 5' end to facilitate secretion, and was introduced into GS115 competent cells (Invitrogen) according to the manufacturer's instructions. Colonies were screened for expression according to the manufacturer's instructions. Samples were then boiled and run on a 10% Bis-tris polyacrylamide gel (BioRad) and transferred to PVDF membranes using a Trans-blot semi-dry blotter (BioRad) according to the manufacturer's instructions. Membranes were blocked by Starting Block (TBS) blocking buffer (Thermo Scientific) and probed for one hour with mouse anti-FLAG antibody-horseradish peroxidase conjugate (Sigma) diluted 1:3000 in Starting Block buffer. After probing, membranes were washed four times with TBST, then developed with Supersignal West Dura chemiluminescent subrate (Thermo Scientific) and imaged using a CCD camera (Alpha Innotech). Representative data showing Pir1b-*H. pomatia* lectin (1), Pir1b-*L. culinaris* lectin (2), and Pir1a-*T. vulgaris* lectin (3) from expression studies is shown in FIG. 11.

Figure 12:
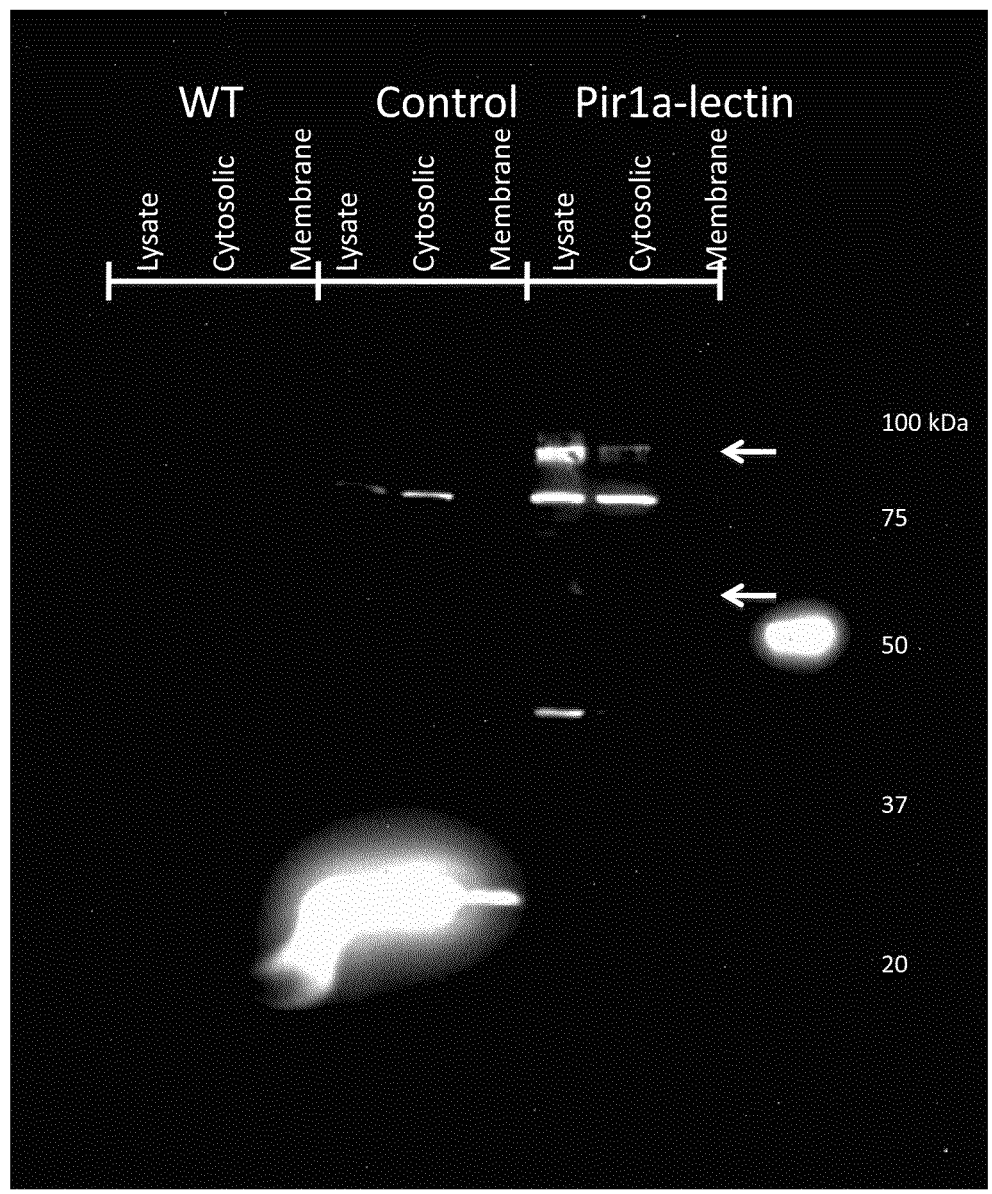
FIG. 12 shows insertion of a Pir1a-lectin fusion protein into the membrane of *P. pastoris*.

To determine whether the lectin-scaffold fusion is properly inserted in the plasma membrane, membrane isolations were performed, 25 mLs of a culture of at O.D.$_{600}$=1 were centrifuged at 5000×g for 10 minutes. All subsequent manipulations were performed at 4° C. and in the presence of protease inhibitors. The pellet was resuspended in 3 mL 1×Tris Buffered Saline (TBS) and sonicated at 30% power using a macrotip for 3 cycles of 10 seconds. The solution was then centrifuged at 30,000×g for 30 minutes to remove the unlysed cells. 1 mL of the supernatant (mixture of membranes and cytosolic proteins) was carefully removed and centrifuged at 540,000×g in a TLA100.3 rotor (Beckman) for 20 minutes to separate the insoluble (membranes) from the soluble (cytosolic proteins). Samples were then boiled and run on a 10% Bis-tris polyacrylamide gel (BioRad) and transferred to PVDF membranes using a Trans-blot semi-dry blotter (BioRad) according to the manufacturer's instructions. Membranes were blocked by Starting Block (TBS) blocking buffer (Thermo Scientific) and probed for one hour with mouse anti-FLAG antibody-horseradish peroxidase conjugate (Sigma) diluted 1:3000 in Starting Block buffer. After probing, membranes were washed four times with TBST, then developed with Supersignal West Dura chemiluminescent substrate (Thermo Scientific) and imaged using a CCD camera (Alpha Innotech). Results from a representative fusion construct, Pir1a-*T. vulgaris* lectin fusion, is shown in FIG. 12.

Example 6

Nuclear Transformation of *C. reinhardtii* with a Nucleic Acid Encoding a Fused Resistance Marker and Gene Encoding a Lectin-Fas1 Fusion Protein A nucleic acid encoding a lectin from *L. culinaris*, truncated *L. culinaris*, and *E. cristagalli* fused to Fas1 from *C. reinhardtii* was introduced into *C. reinhardtii* (SEQ ID NO. 9; SEQ ID NO. 10; SEQ ID NO. 11). Transforming DNA is shown graphically in FIG. 1D. The segment labeled "Transgene" is lectin-Fas1 encoding gene, the segment labeled "5'UTR" is the *C. reinhardtii* HSP70/rbcS2 5'UTR with introns, the segment labeled "Selection Marker" is a bleomycin resistance gene, the segment labeled CM (cleavage moiety) is the 2A viral protease of foot and mouth disease virus (FMDV), the segment labeled "Targeting Signal" is a signal peptide targeting the protein for cell surface display, the segment, labeled "Anchoring Domain" is a glycosylphosphatidylinositol (GPI)-anchoring domain to covalently link the lectin-Fas1 protein to the cell surface, and the segment labeled 3' UTR is the 3'UTR from *C. reinhardtii* rbcS2. The bleomycin resistance gene, 2A and lectin-Fas1 coding regions are physically linked in-frame, resulting in a chimeric single ORF. A Metal Affinity Tag (MAT), Tobacco etch virus (TEV) protease cleavage site, and FLAG epitope were engineered in the junction between the lectin and Fas1 using standard techniques. All DNA manipulations carried out in the construction of this transforming DNA were essentially as described by Sambrook et al., Molecular Cloning: A Laboratory Manual (Cold Spring Harbor Laboratory Press 1989) and Cohen et al., *Meth. Enzymol.* 297, 192-208, 1998.

For these experiments, all transformations were carried out on *C. reinhardtii* strain 21gr. Cells were grown and transformed via electroporation. Cells were grown to mid-log phase (approximately 2-6×10$^6$ cells/ml). Tween-20 was added into cell cultures to a concentration of 0.05% before harvest to prevent cells from sticking to centrifugation tubes. Cells were spun down gently (between 2000 and 5000×g) for 5 min. The supernatant was removed and cells resuspended in TAP+40 mM sucrose media. 1 to 2 ug of transforming DNA was mixed with ~1×10$^8$ cells on ice and transferred to electroporation cuvettes. Electroporation was performed with the capacitance set at 25 uF, the voltage at 800 V to deliver V/cm of 2000 and a time constant for 10-14 ms. Following electroporation, the cuvette was returned to room temperature for 5-20 min. Cells were transferred to 10 ml of TAP+40 mM sucrose and allowed to recover at room temperature for 12-16 hours with continuous shaking. Cells were then harvested by centrifugation at between 2000×g and 5000×g and resuspended in 0.5 ml TAP+40 mM sucrose medium. 0.25 ml of cells was plated on TAP+20 ug/ml bleomycin. All transformations were carried out under bleomycin selection (20 µg/ml) in which resistance was conferred by the gene encoded by the segment in FIG. 1D labeled "Selection Marker." Transformed strains are maintained in the presence of bleomycin to prevent loss of the exogenous DMA.

Colonies growing in the presence of bleomycin were screened by dot blot. Briefly, colonies were lysed by Bug-Buster Protein Extraction Reagent (Novagen) and MAT-tagged proteins were separated using MagneHis Ni-particles (Promega), according to the manufacturer's instructions. After exposure to the proteins, the beads were washed three times by 150 µl of 1×Tris Buffered Saline with 0.05% Tween- 20 (TBST) at room temperature. Proteins were released from beads by 150 µl 20 µM EDTA, 25 mM Tris-HCl pH 7.0, 400 mM NaCl, and the 150 µl eluates were dot blotted onto nitrocellulose membranes. Membranes were blocked by Starting Block (TBS) blocking buffer (Thermo Scientific) and probed for one hour with mouse anti-FLAG antibody-horseradish peroxidase conjugate (Sigma) diluted 1:3000 in Starting Block buffer. After probing, membranes were washed four times with TBST, then developed with Super-signal West Dura chemiluminescent substrate (Thermo Scientific) and imaged using a CCD camera (Alpha Innotech). Colonies showing positive results in the dot blot analysis were then screened by western blotting.

Figure 13:
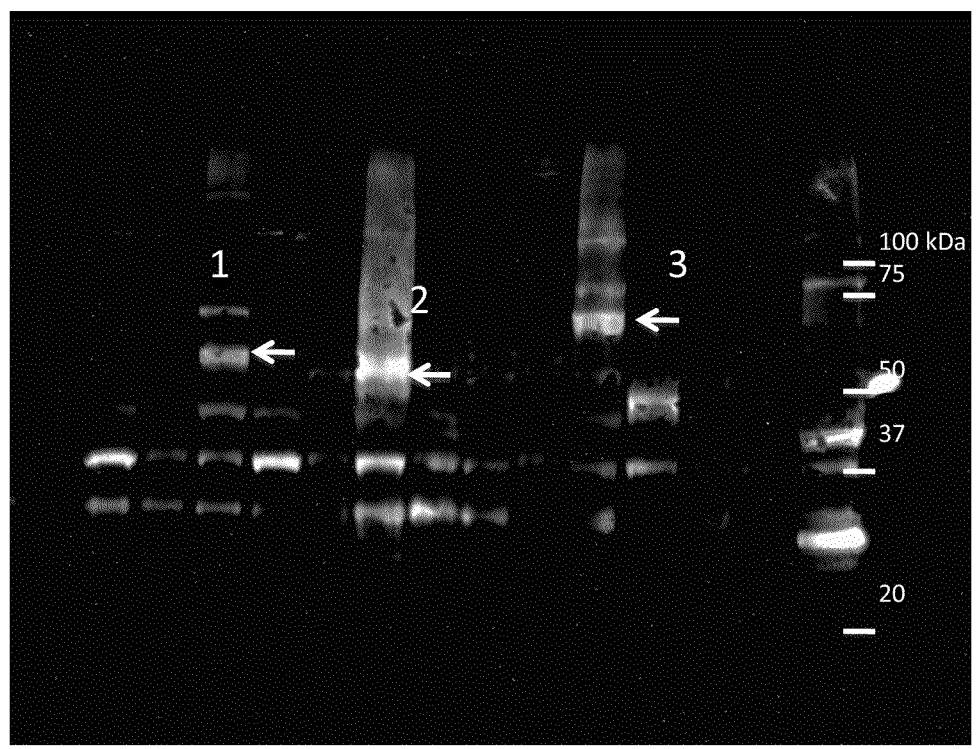
FIG. 13 shows expression of Fas1-lectin fusions. Band 1: Fas1-*L. culinaris* lectin; Band 2: Fas1-truncated *L. culinaris* lectin; Band 3: Fas1-*E. cristagalli* lectin.

Patches of algae cells growing on TAP agar plates were lysed by resuspending cells in 50 µl of 1×SDS sample buffer with reducing agent (BioRad). Samples were then boiled and ran on a 10% Bis-tris polyacrylamide gel (BioRad) and transferred to PVDF membranes using a Trans-blot semi-dry blotter (BioRad) according to the manufacturer's instructions. Membranes were blocked by Starting Block (TBS) blocking buffer (Thermo Scientific) and probed for one hour with mouse anti-FLAG antibody-horseradish peroxidase conjugate (Sigma) diluted 1:3000 in Starting Block buffer. After probing, membranes were washed four times with TBST, then developed with Supersignal West Dura chemiluminescent subrate (Thermo Scientific) and imaged using a CCD camera (Alpha Innotech), Results from three strains are shown in FIG. 13.

Figure 14:
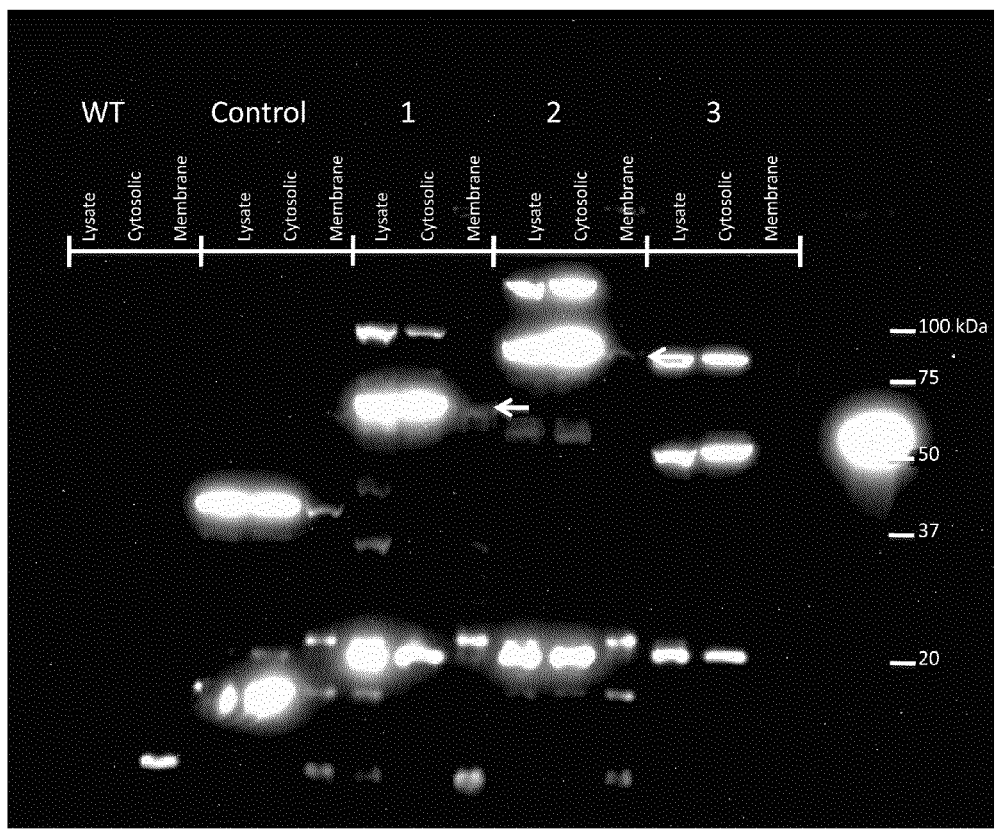
FIG. 14 shows a western blot describing the subcellular localization of Fas1-lectin fusion proteins. WT: 21gr; Control: Cytosolic enzyme; 1: Fas1-*L. culinaris* lectin fusion; 2: Fas1-*L. culinaris* truncated lectin fusion; 3: Fas1-T. *E. cristagalli* lectin fusion
Figure 15:
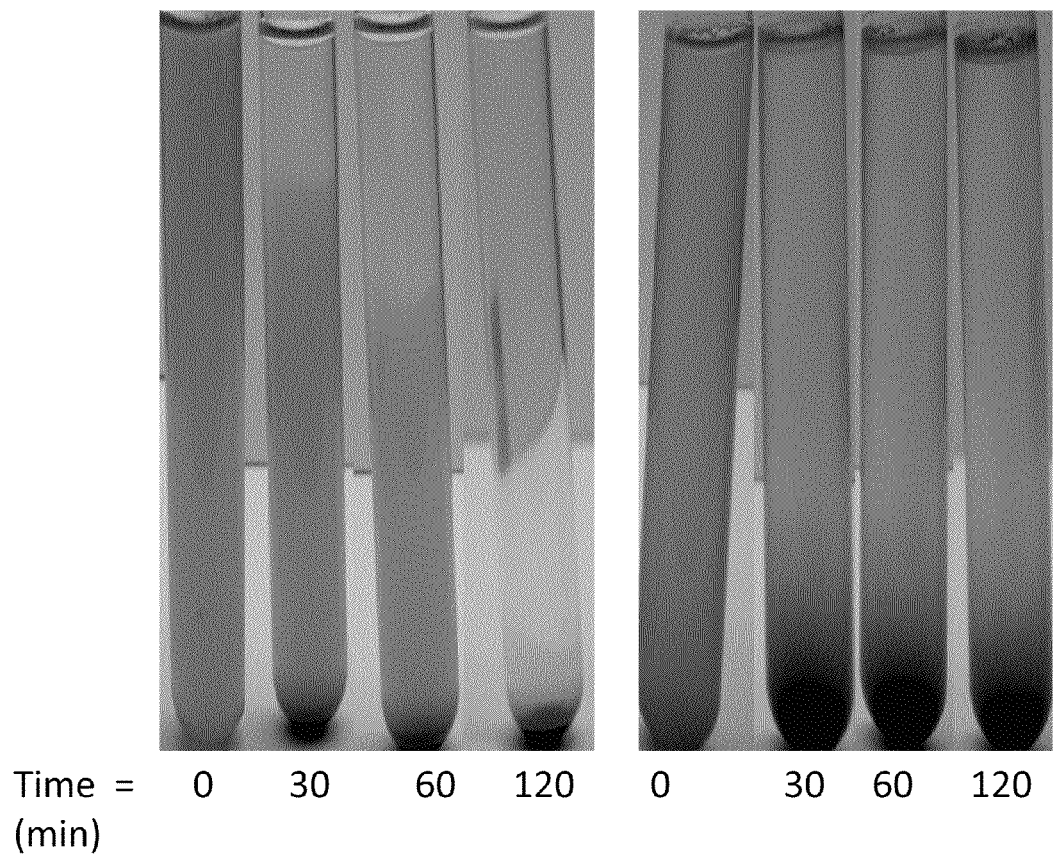
FIG. 15 shows the effect of the presence of the Fas1-*T. vulgaris* lectin fusion protein construct on settling.

To determine whether the lectin-Fas1 fusion was properly inserted in the plasma membrane in an orientation where the lectin is externally presented, membrane isolations were performed, 100 mL of a culture of a minimum $1\times10^7$ cells/mL were centrifuged at 5000×g for 10 minutes. All subsequent manipulations were performed at 4° C. and in the presence of protease inhibitors. The pellet was resuspended in 3 mL 1×Tris Buffered Saline (TBS) and sonicated at 30% power using a macrotip for 3 cycles of 10 seconds. The solution was then centrifuged at 30,000×g for 30 minutes to remove the unlysed cells. 1 mL of the supernatant (mixture of membranes and cytosolic proteins) was carefully removed and centrifuged at 540,000×g in a TLA100.3 rotor (Beckman) for 20 minutes to separate the insoluble (membranes) from the soluble (cytosolic proteins). Samples were then boiled and run on a 10% Bis-tris polyacrylamide gel (BioRad) and transferred to PVDF membranes using a Trans-blot semi-dry blotter (BioRad) according to the manufacturer's instructions. Membranes were blocked by Starting Block (TBS) blocking buffer (Thermo Scientific) and probed for one hour with mouse anti-FLAG antibody-horseradish peroxidase conjugate (Sigma) diluted 1:3000 in Starting Block buffer. After probing, membranes were washed four times with TBST, then developed with Supersignal West Dura chemiluminescent substrate (Thermo Scientific) and imaged using a CCD camera (Alpha Innotech). Results from several fusion constructs are shown in FIG. 14. As expected from the mode of membrane anchoring, there still exists a significant amount of protein, in the cytosolic/soluble fraction. However, there is also protein in the membrane fraction. The effect of the presence of the Fas1-*E. cristagalli* lectin, fusion protein construct on settling can be seen in FIG. 15.

Example 7

Nuclear Transformation of *C. reinhardtii* with a Nucleic Acid Encoding a Fused Resistance Marker and Gene Encoding a GP3-Lectin Fusion Protein A nucleic acid encoding a lectin from *H. pomatia* and *L. culinaris* fused to GP1 from *C. reinhardtii* was introduced into *C. reinhardtii* (SEQ ID NO. 12; SEQ ID NO. 13). Transforming DNA is shown graphically in FIG. 1E. The segment labeled "Transgene" is lectin-GP1 encoding gene, the segment labeled "Promoter/5'UTR" is the *C. reinhardtii* HSP70/rbcS2 5' UTR with introns, the segment labeled "Selectable Marker" is a bleomycin resistance gene, the segment labeled CM (cleavage moiety) is the 2A viral protease of foot and mouth disease virus (FMDV), the segment labeled "Targeting Signal" is a signal peptide targeting the protein for cell surface display, and the segment labeled 3' UTR is the 3'UTR from *C. reinhardtii* rbcS2. The bleomycin resistance gene, 2A and GP1-lectin coding regions are physically linked in-frame, resulting in a chimeric single ORF. A Metal Affinity Tag (MAT), Tabbacco etch virus (TEV) protease cleavage site, and FLAG epitope are engineered in the junction between the lectin and GP1 using standard techniques. Another Flag epitope is encoded at the 3' end of the transgene. All DNA manipulations carried out in the construction of this transforming DNA were essentially as described by Sambrook et al., Molecular Cloning: A Laboratory Manual (Cold Spring Harbor Laboratory Press 1989) and Cohen et al., *Meth. Enzymol.* 297, 192-208, 1998.

For these experiments, all transformations were carried out on *C. reinhardtii* strain 21gr. Cells were grown and transformed via electroporation. Cells were grown to mid-log phase (approximately $2\text{-}6\times10^6$ cells/ml). Tween-20 was added into cell cultures to a concentration of 0.05% before harvest to prevent cells from sticking to centrifugation tubes. Cells were spun down gently (between 2000 and 5000×g) for 5 min. The supernatant was removed and the cells resuspended in TAP+40 mM sucrose media, 1 to 2 ug of transforming DNA was mixed with ~$1\times10^8$ cells on ice and transferred to electroporation cuvettes. Electroporation was performed with the capacitance set at 25 uF, the voltage at 800 V to deliver V/cm of 2000 and a time constant for 10-34 ms. Following electroporation, the cuvette was returned to room temperature for 5-20 min. Cells were transferred to 10 ml of TAP+40 mM sucrose and allowed to recover at room temperature for 12-16 hours with continuous shaking. Cells were then harvested by centrifugation at between 2000 g and 5000 g and resuspended in 0.5 ml TAP+40 mM sucrose medium. 0.25 ml of cells were plated on TAP+20 ug/ml bleomycin. All transformations were carried out under bleomycin selection (20 µg/ml) in which resistance was conferred by the gene encoded by the segment in FIG. 1E labeled "Selection Marker." Transformed strains are maintained in the presence of bleomycin to prevent loss of the exogenous DNA.

Colonies growing in the presence of bleomycin were screened by dot blot. Briefly, colonies were lysed by Bug-Buster Protein Extraction Reagent (Novagen) and MAT-tagged proteins were separated using MagneHis Ni-particles (Promega), according to manufacturer's instructions. After exposure to the proteins, the beads were washed three times by 150 µl of 1×Tris Buffered Saline with 0.05% Tween-20 (TBST) at room temperature. Proteins were released from beads by 150 µl 10 µM EDTA, 25 mM Tris-HCl pH 7.0, 400 mM NaCl, and the 150 µl eluates were dot blotted onto nitrocellulose membranes. Membranes were blocked by Starting Block (TBS) blocking buffer (Thermo Scientific) and probed for one hour with mouse anti-FLAG antibody-horseradish peroxidase conjugate (Sigma) diluted 1:3000 in Starting Block buffer. After probing, membranes were washed four times with TBST, then developed with Supersignal West Dura chemiluminescent substrate (Thermo Scientific) and imaged using a CCD camera (Alpha Innotech). Colonies showing positive results in the dot blot analysis are then screened by western blotting.

Figure 16:
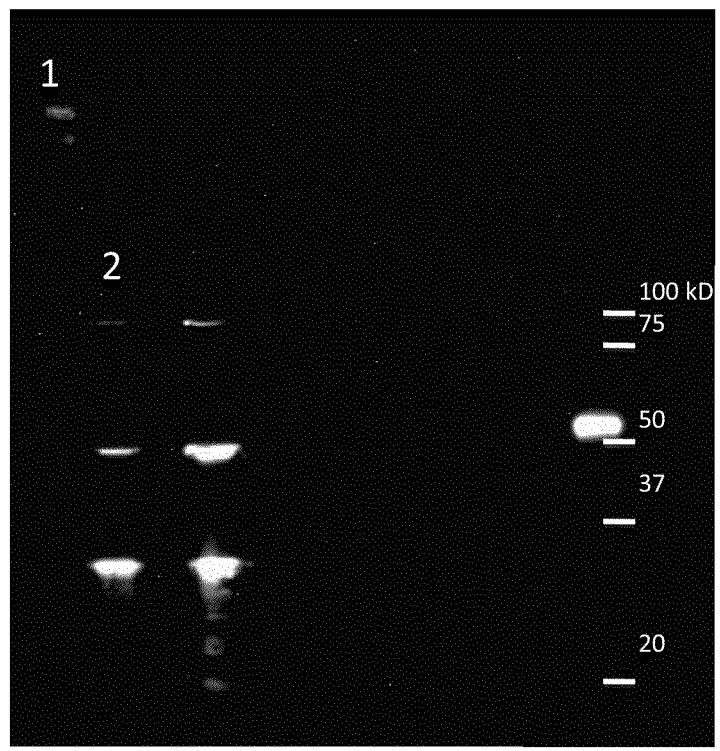
FIG. 16 shows whole cell expression of GP1-lectin proteins in *C. reinhardtii*. 1: GP1-*H. pomatia* lectin fusion; 2: GP1-*L. culinaris* truncated lectin fusion.
Figure 17:
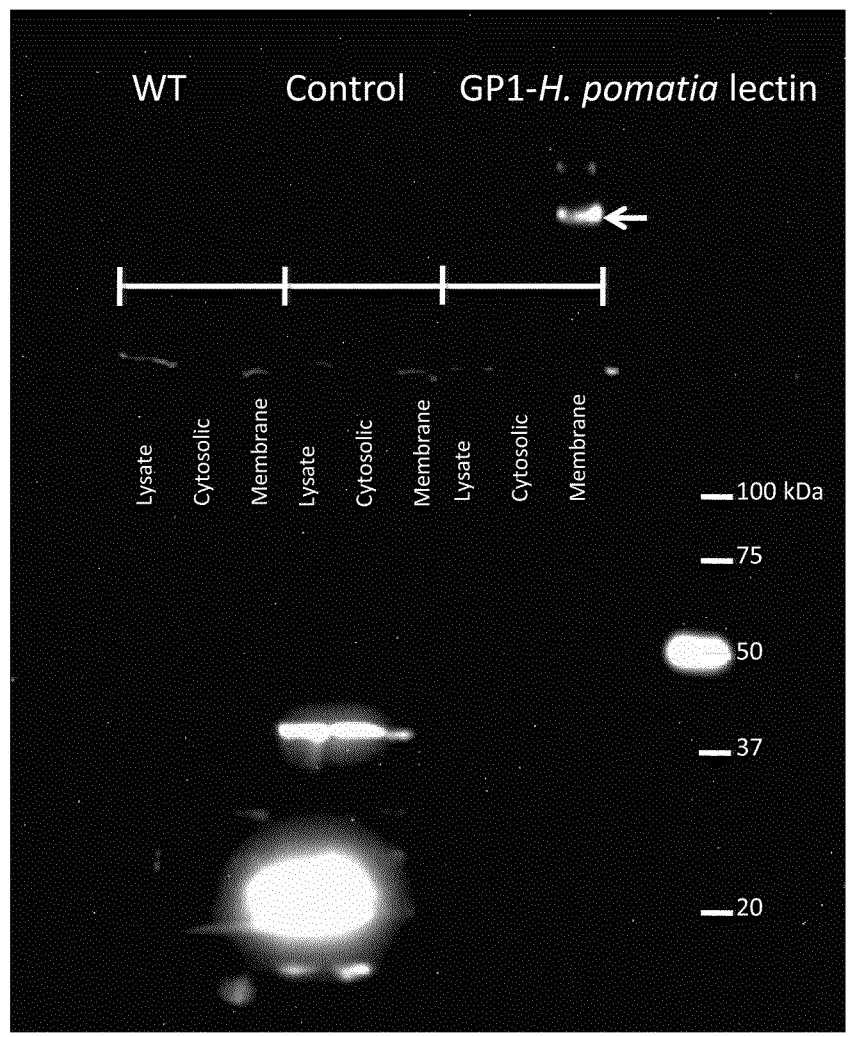
FIG. 17 shows a western blot describing the subcellular localization of GP1-lectin fusion proteins. WT: 21gr; Control: Cytosolic enzyme; GP1-*H. pomatia* lectin.
Figure 18:
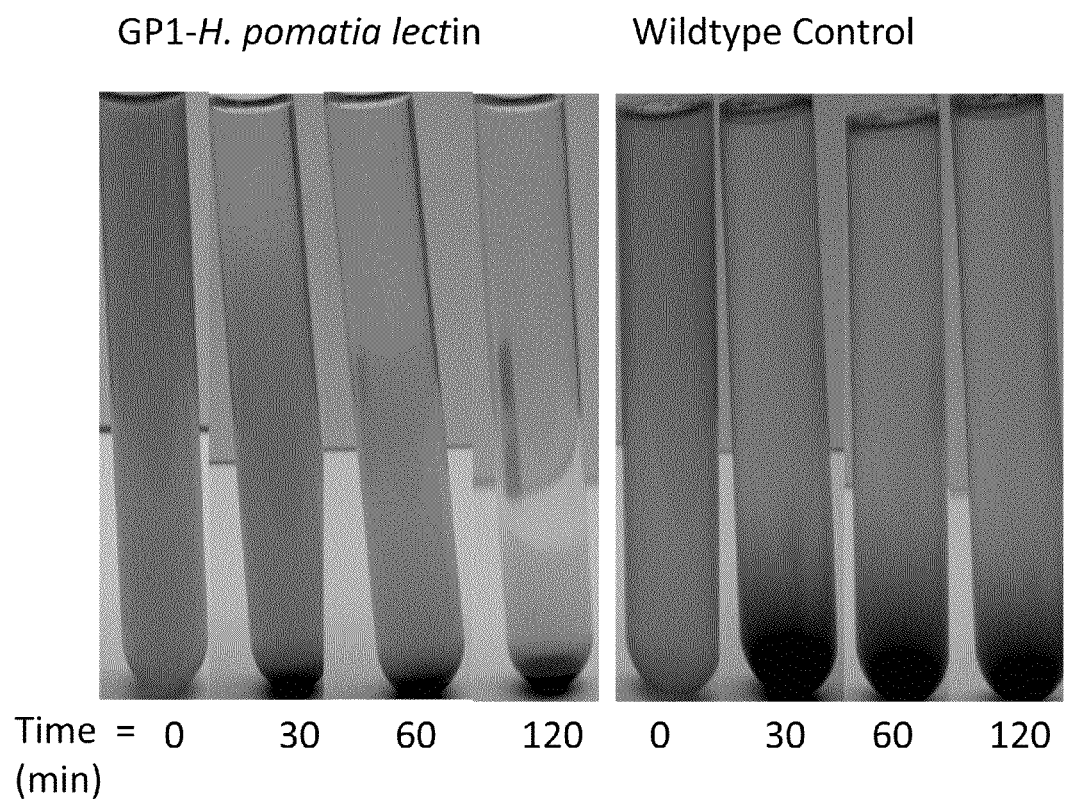
FIG. 18 shows the effect of the presence of the GP1-*H. pomatia* lectin construct on settling.
Figure 19:
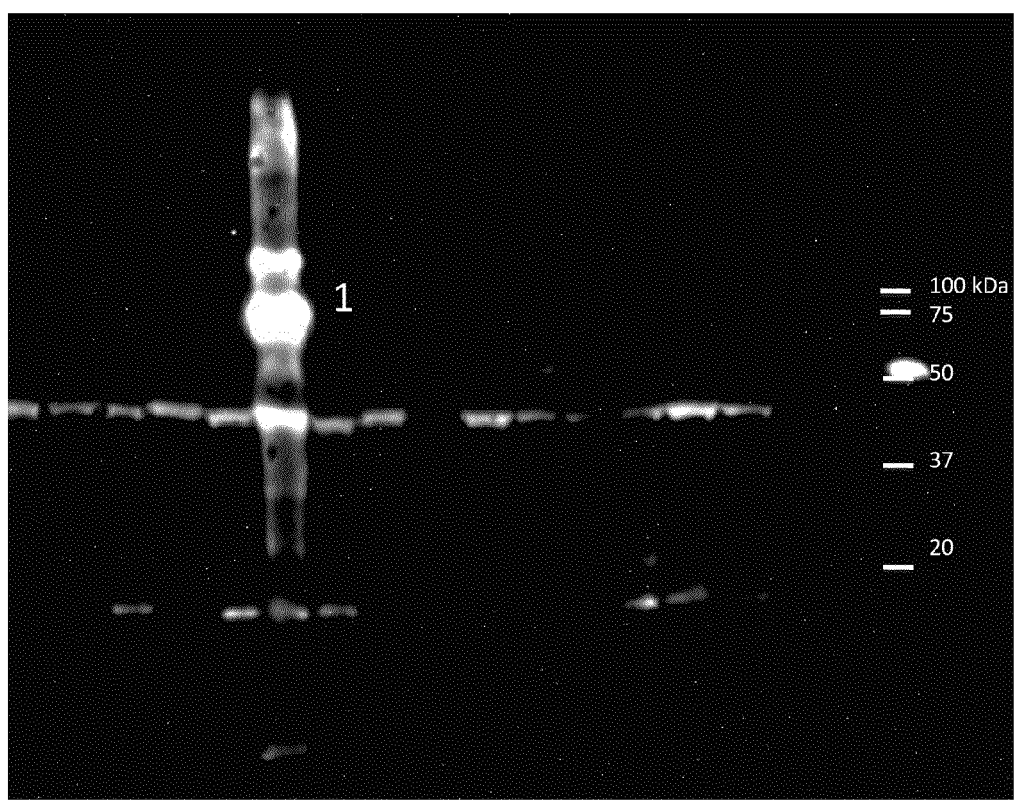
FIG. 19 shows a western blot showing expression of a scFv5-Fas1 fusion protein in C. reinhardtii. 1: The fusion protein is shown here. The higher band is the residual intact fusion with the bleomycin protein.

Patches of algae cells growing on TAP agar plates were lysed by resuspending cells in 50 µl of 1×SDS sample buffer with reducing agent (BioRad). Samples were then boiled and run on a 10% Bis-tris polyacrylamide gel (BioRad) and transferred to PVDF membranes using a Trans-blot semi-dry blotter (BioRad) according to the manufacturer's instructions. Membranes were blocked by Starting Block (TBS) blocking buffer (Thermo Scientific) and probed for one hour with mouse anti-FLAG antibody-horseradish peroxidase conjugate (Sigma) diluted 1:3000 in Starting Block buffer. After probing, membranes were washed four times with TBST, then developed with Supersignal West Dura chemiluminescent subrate (Thermo Scientific) and imaged using a CCD camera (Alpha Innotech), A small amount of intact fusion (Bleomycin resistance marker fused to GP1-lectin) is translated by the cells; as the resistance marker forms a dimer, these products migrate at a higher molecular weight. FIG. 16. indicates that GP1-lectin fusions involving lectins from *H. pomatia* and *L. culinaris* were produced in *C. reinhardtii*.

To determine whether the lectin-GP1 fusion is properly inserted in the plasma membrane in an orientation where the lectin is externally presented, membrane isolations were performed. 100 mL of a culture of at minimum $1\times10^7$ cells/mL were centrifuged at 5000×g for 10 minutes. All subsequent manipulations were performed at 4° C. and in the presence of protease inhibitors. The pellet was resuspended in 3 mL 1×Tris Buffered Saline (TBS) 2M urea and sonicated at 30% power using a macrotip for 3 cycles of 10 seconds. The solution was then centrifuged at 30,000×g for 30 minutes to remove the unlysed cells. 1 mL of the supernatant (mixture of membranes and cytosolic proteins) was carefully removed and centrifuged at 540,000×g in a TLA100.3 rotor (Beckman) for 20 minutes to separate the insoluble (membranes) from the soluble (cytosolic proteins). Samples were then boiled and run on a 10% Bis-tris polyacrylamide gel (BioRad) in the presence of 2M urea and transferred to PVDF membranes using a Trans-blot semi-dry blotter (BioRad) according to the manufacturer's instructions. Membranes were blocked by Starring Block (TBS) blocking buffer (Thermo Scientific) and probed for one hour with mouse anti-FLAG antibody-horseradish peroxidase conjugate (Sigma) diluted 1:3000 in Starting Block buffer. After probing, membranes were washed four times with TBST, then developed with Supersignal West Dura chemiluminescent subrate (Thermo Scientific) and imaged using a CCD camera (Alpha Innotech). The results shown in FIG. 17. demonstrate the presence of GP1-*H. pomatia* lectin in the membrane fraction. The effect of the presence of the GP1-*H. pomatia* lectin construct on settling can be seen in FIG. 18.

Example 8

Nuclear Transformation of *C. reinhardtii* with a Nucleic Acid Encoding a Fused Resistance Marker and Gene Encoding a Fas1-scFv Fusion Protein A nucleic acid encoding an antibody/single chain variable fragment (scFv5) fused to Fas1 was introduced into *C. reinhardtii* (SEQ ID NO, 14). Transforming DNA is shown graphically in FIG. 1D. The segment labeled "Transgene" is scFv5-Fas1 encoding gene, the segment labeled "Promoter/5'UTR" is the *C. reinhardtii* HSP70/rbcS2 5' UTR with introns, the segment labeled "Selectable Marker" is a bleomycin resistance gene, the segment labeled CM (cleavage moiety) is the 2A viral protease of foot and mouth disease virus (FMDV), the segment labeled "Targeting Signal" is a signal peptide targeting the protein for cell surface display, the segment labeled "Anchoring Domain" is a glycosylphosphatidylinositol (GPI)-anchoring domain to covalently link the scFv-Fas1 protein to the cell surface, and the segment labeled 3' UTR is the 3'UTR from *C. reinhardtii* rbcS2. The bleomycin resistance gene, 2A and lectin-Fas1 coding regions are physically linked in-frame, resulting in a chimeric single ORF. A Metal Affinity Tag (MAT), Tobacco Etch Virus (TEV) protease cleavage site, and a FLAG epitope tag are engineered in the junction between the scFv5 and Fas1 using standard techniques. All DNA manipulations carried out in the construction of this transforming DNA were essentially as described by Sambrook et al., Molecular Cloning: A Laboratory Manual (Cold Spring Harbor Laboratory Press 1989) and Cohen et al., *Meth. Enzymol.* 297, 192-208, 1998.

For these experiments, all transformations were carried out on *C. reinhardtii* strain 21gr. Cells were grown and transformed via electroporation. Cells were grown to mid-log phase (approximately $2\text{-}6\times10^6$ cells/ml). Tween-20 was added into cell cultures to a concentration of 0.05% before harvest to prevent cells from sticking to centrifugation tubes. Cells were down gently (between 2000 and 5000×g) for 5 min. The supernatant was removed and cells resuspended in TAP+40 mM sucrose media. 1 to 2 ug of transforming DNA was mixed with $\sim1\times10^8$ cells on ice and transferred to electroporation cuvettes. Electroporation was performed with the capacitance set at 25 uF, the voltage at 800 V to deliver V/cm of 2000 and a time constant for 10-14 ms. Following electroporation, the cuvette was returned to room temperature for 5-20 min. Cells were transferred to 10 ml of TAP+40 mM sucrose and allowed to recover at room temperature for 12-16 hours with continuous shaking. Cells were then harvested by centrifugation at between 2000 g and 5000 g and resuspended in 0.5 ml TAP+40 mM sucrose medium. 0.25 ml of cells were plated on TAP+20 ug/ml bleomycin. All transformations were carried out under bleomycin selection (20 μg/ml) in which resistance was conferred by the gene encoded by the segment in FIG. 1D labeled "Selection Marker." Transformed strains are maintained in the presence of bleomycin to prevent loss of the exogenous DNA.

Colonies growing in the presence of bleomycin were screened by dot blot. Briefly, colonies were lysed by BugBuster Protein Extraction Reagent (Novagen) and MAT-tagged proteins were separated using MagneHis Ni-particles (Promega), according to manufacturer's instructions. After exposure to the proteins, the beads were washed three times by 150 μl of 1×Tris Buffered Saline with 0.05% Tween-20 (TBST) at room temperature. Proteins were released from beads by 150 μl 10 μM EDTA, 25 mM Tris-HCl pH 7.0, 400 mM NaCl, and the 150 μl eluates were dot blotted onto nitrocellulose membranes. Membranes were blocked by Starting Block (TBS) blocking buffer (Thermo Scientific) and probed for one hour with mouse anti-FLAG antibody-horseradish peroxidase conjugate (Sigma) diluted 1:3000 in Starting Block buffer. After probing, membranes were washed four times with TBST, then developed with Supersignal West Dura chemiluminescent subrate (Thermo Scientific) and imaged using a CCD camera (Alpha Innotech). Colonies showing positive results in the dot blot analysis were then screened by western blotting.

Patches of algae cells growing on TAP agar plates were lysed by resuspending cells in 50 μl of 1×SDS sample buffer with reducing agent (BioRad). Samples were then boiled and run on a 10% Bis-tris polyacrylamide gel (BioRad) and transferred to PVDF membranes using a Trans-blot semi-dry blotter (BioRad) according to manufacturers instructions. Membranes were blocked by Starting Block (TBS) blocking buffer (Thermo Scientific) and probed for one hour with mouse anti-FLAG antibody-horseradish peroxidase conjugate (Sigma) diluted 1:3000 in Starting Block buffer. After probing, membranes were washed four times with TBST, then developed with Supersignal West Dura chemiluminescent subrate (Thermo Scientific) and imaged using a CCD camera (Alpha Innotech), Results from 1 colony (and wild-type control) are shown in FIG. 19. A small amount of intact fusion (Bleomycin resistance marker fused to scFv5-Fas1) is translated by the cells; as the resistance marker forms a dimer, these products migrate at a higher molecular weight. The results indicate that scFv-Fas1 fusion protein is being produced from the strains.

Figure 20:
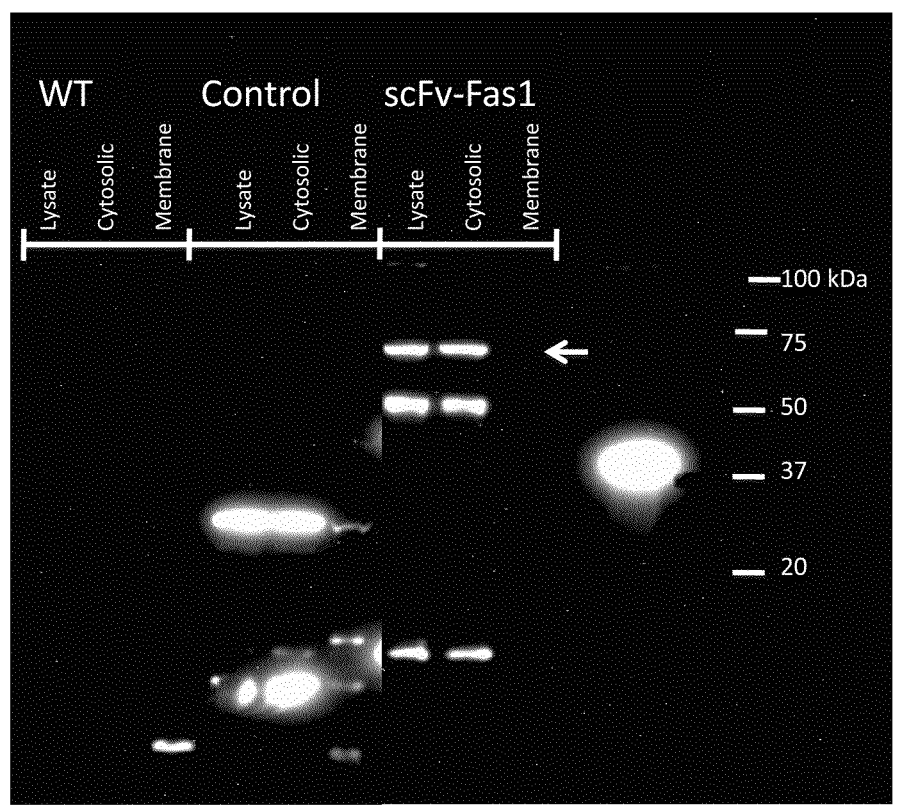
FIG. 20 shows a western blot describing the subcellular localization of Fas1 fusion proteins. WT: 21gr; Control: Cytosolic enzyme; scFv5-Fas1 fusion. There is scFv5-Fas1 protein localizing to the membrane fraction (arrow).

To determine whether the scFv5-Fas1 fusion is properly inserted in the plasma membrane in an orientation where it is externally presented, membrane isolations were performed. 100 mL of a culture of at minimum $1 \times 10^7$ cells/mL were centrifuged at 5000×g for 10 minutes. All subsequent manipulations were performed at 4° C. and in the presence of protease inhibitors. The pellet was resuspended in 3 mL 1×Tris Buffered Saline (TBS) and sonicated at 30% power using a macrotip for 3 cycles of 10 seconds. The solution was then centrifuged at 30,000×g for 30 minutes to remove the unlysed cells. 1 mL of the supernatant (mixture of membranes and cytosolic proteins) was carefully removed and centrifuged at 540,000×g in a TLA100.3 for 20 minutes to separate the insoluble (membranes) from the soluble (cytosolic proteins). Samples were then boiled and run on a 10% Bis-tris polyacrylamide gel (BioRad) and transferred to PVDF membranes using a Trans-blot semi-dry blotter (BioRad) according to the manufacturer's instructions. Membranes were blocked by Starting Block (TBS) blocking buffer (Thermo Scientific) and probed for one hour with mouse anti-FLAG antibody-horseradish peroxidase conjugate (Sigma) diluted 1:3000 in Starting Block buffer. After probing, membranes were washed four times with TBST, then developed with Supersignal West Dura chemiluminescent subrate (Thermo Scientific) and imaged using a CCD camera (Alpha Innotech). Results from a scFv-Fas1 membrane isolation are shown in FIG. 20.

Example 9

Nitrate-Inducible Expression of a Flocculation Moiety in C. reinhardtii

In this example, a nucleic acid encoding a lectin from *H. pomatia* was introduced into *C. reinhardtii* (SEQ ID NO. 15). Transforming DNA is shown graphically in FIG. 1F. The segment labeled "Transgene" is lectin-encoding gene, the segment labeled "5'UTR" is the *C. reinhardtii* nitrate reductase 5' UTR, the segment labeled "Selectable Marker" is the nitrate reductase gene, the segment labeled CM (cleavage moiety) is the 2A viral protease of foot and mouth disease virus (FMDV), and the segment labeled 3' UTR is the 3'UTR from *C. reinhardtii* nitrate reductase. Nitrate reductase, 2A and *H. pomatia* lectin coding regions are physically linked in-frame, resulting in a chimeric single ORF. A Metal Affinity Tag (MAT), Tobacco Etch Virus (TEV) protease cleavage site, and FLAG epitope are engineered at the 3' end of the lectin, using standard techniques. All DNA manipulations carried out in the construction of this transforming DNA were essentially as described by Sambrook et al., Molecular Cloning: A Laboratory Manual (Cold Spring Harbor Laboratory Press 1989) and Cohen et al., *Meth. Enzymol*, 297, 192-208, 1998.

For these experiments, all transformations were carried out on *C. reinhardtii* strain Nit1-305, deficient in functional nitrate reductase, from the *Chlamydomonas* center. Cells were grown and transformed via electroporation. Cells were grown to mid-log phase (approximately $2-6 \times 10^6$ cells/ml). Tween-20 was added into cell cultures to a concentration of 0.05% before harvest to prevent cells from sticking to centrifugation tubes. Cells were spun down gently (between 2000 and 5000×g) for 5 min. The supernatant was removed and cells resuspended in TAP+40 mM sucrose media. 1 to 2 ug of transforming DNA was mixed with ~$1 \times 10^8$ cells on ice and transferred to electroporation cuvettes. Electroporation was performed with the capacitance set at 25 uF, the voltage at 800 V to deliver V/cm of 2000 and a time constant for 10-14 ms. Following electroporation, the cuvette was returned to room temperature for 5-20 min. Cells were transferred to 10 ml of TAP+40 mM sucrose and allowed to recover at room temperature for 12-16 hours with continuous shaking. Cells were then harvested by centrifugation at between 2000 g and 5000 g and resuspended in 0.5 ml TAP+40 mM sucrose medium. 0.25 ml of cells were plated on TAP-$NH_4Cl$, +7.4 mM $KNO_3$. All transformations were carried out in the presence of 7.4 mM $KNO_3$ in which the ability to utilize $NO_3$ as the sole nitrogen source is conferred by nitrate reductase. Transformed strains are maintained in the presence of $KNO_3$ to prevent loss of the exogenous DNA.

Colonies growing in TAP-$NH_4Cl$, +7.4 mM $KNO_3$ were screened by dot blot. Briefly, colonies were lysed by Bug-Buster Protein Extraction Reagent (Novagen) and MAT-tagged proteins were separated using MagneHis Ni-particles (Promega), according to manufacturer's instructions. After exposure to the proteins, the beads were washed three times by 150 µl of 1×Tris Buffered Saline with 0.05% Tween-20 (TBST) at room temperature. Proteins were released from beads by 150 µl 20 µM EDTA, 25 mM Tris-HCl pH 7.0, 400 mM NaCl, and the 150 µl eluates were dot blotted onto nitrocellulose membranes. Membranes were blocked by Starting Block (TBS) blocking buffer (Thermo Scientific) and probed for one hour with mouse anti-FLAG antibody-horseradish peroxidase conjugate (Sigma) diluted 1:3000 in Starting Block buffer. After probing, membranes were washed four times with TBST, then developed with Supersignal West Dura chemiluminescent substrate (Thermo Scientific) and imaged using a CCD camera (Alpha Innotech). Colonies showing positive results in the dot blot analysis were then screened by western blotting.

Patches of algae cells growing on TAP agar plates were lysed by resuspending cells in 50 µl of 1×SDS sample buffer with reducing agent (BioRad). Samples were then boiled and run on a 10% Bis-tris polyacrylamide gel (BioRad) and transferred to PVDF membranes using a Trans-blot semi-dry blotter (BioRad) according to manufacturers instructions. Membranes were blocked by Starting Block (TBS) blocking buffer (Thermo Scientific) and probed for one hour with mouse anti-FLAG antibody-horseradish peroxidase conjugate (Sigma) diluted 1:3000 in Starting Block buffer. After probing, membranes were washed four times with TBST, then developed with Supersignal West Dura chemiluminescent substrate (Thermo Scientific) and imaged using a CCD camera (Alpha Innotech).

Figure 21:
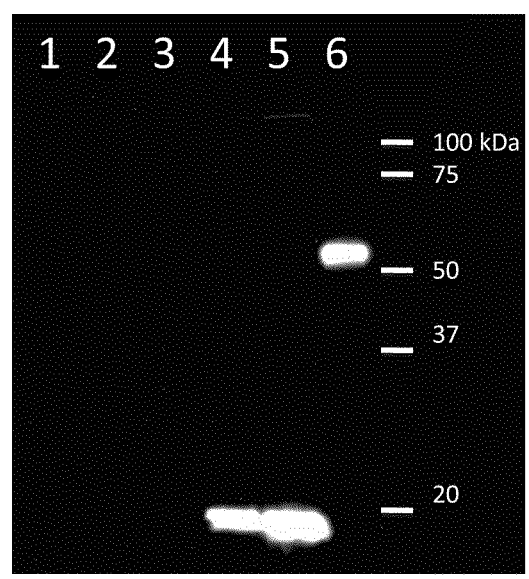
FIG. 21 shows $NO_3^-$ induced expression of H. pomatia lectin in C. reinhardtii. Lane 1: Time 0, TAP; Lane 2: Time 12 hours, TAP; Lane 3: Time 24 hours, TAP; Lane 4: Time 12 hours, TAP-$NH_4Cl$+7.4 mM $KNO_3$; Lane 5: Time 24 hours, TAP-$NH_4Cl$+7.4 mM $KNO_3$ Lane 6: Control.

In order to characterize the inducibility of expression, 50 mL of the Nit-2A-*H. pomatia* lectin strain was grown in TAP media under light. Once the density of the cell culture reached $1 \times 10^6$ cells/mL, the culture was divided into two 25 mL samples. Each was centrifuged at 5000×g for 10 minutes. The supernatant was removed and one sample was resuspended in 25 mL TAP. The other sample was resuspended in 25 mL TAP-NH4Cl+7.4 mM KNO3. $20 \times 10^6$ cells were centrifuged and frozen at time points 0, 12 hrs, and 24 hrs. These samples were processed and MAT-tagged proteins were separated using MagneHis Ni-particles (Promega), according to manufacturer's instructions. After exposure to the proteins, the beads were washed three times by 150 µl of 1×Tris Buffered Saline with 0.05% Tween-20 (TBST) at room temperature. Proteins were released from beads by 150 µl 20 µM EDTA, 25 mM Tris-HCl pH 7.0, 400 mM NaCl. 50 uL of 4×SDS sample buffer with reducing agent (BioRad) was added. Samples were then boiled and run on a 10% Bis-tris polyacrylamide gel (BioRad) and transferred to PVDF membranes using a Trans-blot semi-dry blotter (BioRad) according to the manufacturer's instructions. Membranes were blocked by Starting Block (TBS) blocking buffer (Thermo Scientific) and probed for one hour with mouse anti-FLAG antibody-horseradish peroxidase conjugate (Sigma) diluted 1:3000 in Starting Block buffer. After probing, membranes were washed four times with TBST, then developed with Supersignal West Dura chemiluminescent substrate (Thermo Scientific) and imaged using a CCD camera (Alpha Innotech). The induction of *H. pomatia* lectin expression is very dramatic as shown in FIG. 21.

Example 10

Nitrogen Deprivation-Induced Mating Phenotype Mediated Flocculation of *Chlamydomonas reinhardtii*

Figure 22:
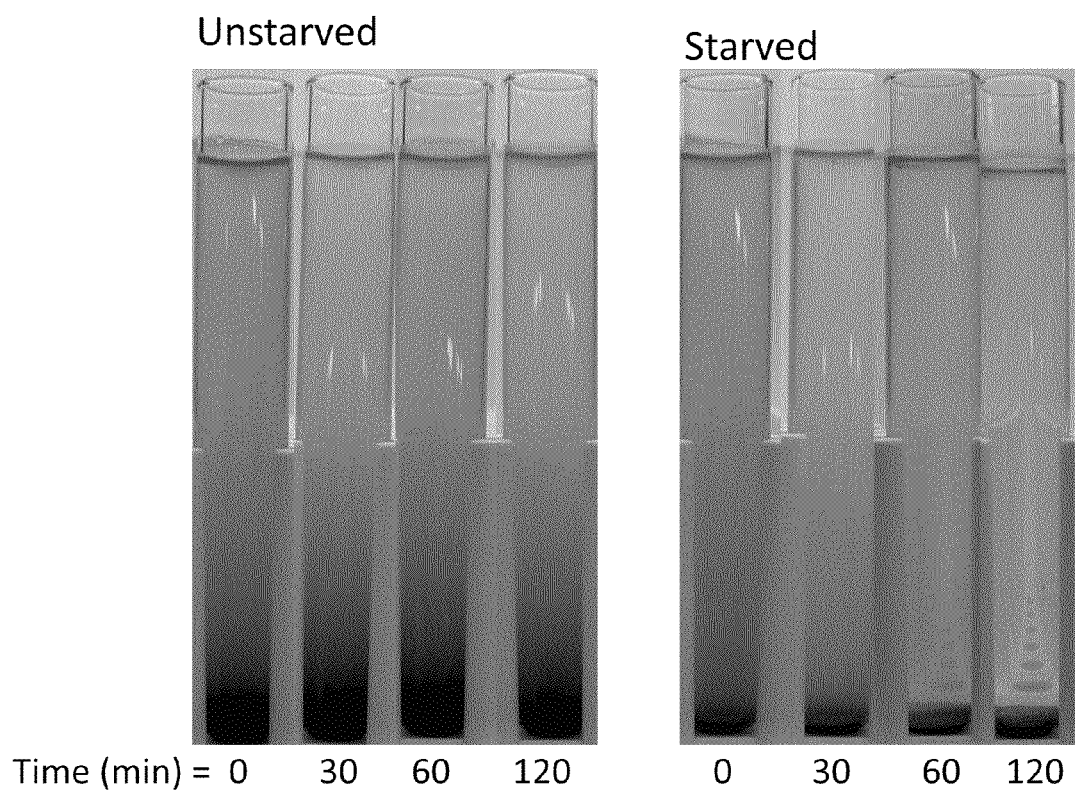
FIG. 22 shows flocculation of two C. reinhardtii strains following nitrogen deprivation.

In this example, the two *Chlamydomonas reinhardtii* strains 21gr and 6145c, representing the two mating types plus (MT+) and minus (MT−), respectively were grown in Tris-Acetate-Phosphate (TAP) media to $5 \times 10^6$ cells/mL. 1 L of each culture was centrifuged at 5000×g for 10 minutes. The supernatant was removed and the pellet was resuspended in 1 L TAP media without ammonium chloride (TAP-$NH_4Cl$). The culture was centrifuged again to wash away residual ammonium chloride at 5000×g for 10 minutes. The supernatant was removed and the pellet was resuspended in 1 L TAP-$NH_4Cl$. The culture was centrifuged again at 5000×g for 10 minutes. The pellet was resuspended in 1 L TAP-$NH_4Cl$ and allowed to shake for 12-16 hours under light. The cultures were combined in a 1:1 ratio and allowed to shake for 12 hours under light before observing the sedimentation. Sedimentation or settling of 7.5 mL of the culture was observed in 13×300 mm borosilicate disposable culture tubes over time. Results are shown in FIG. 22.

Figure 23:
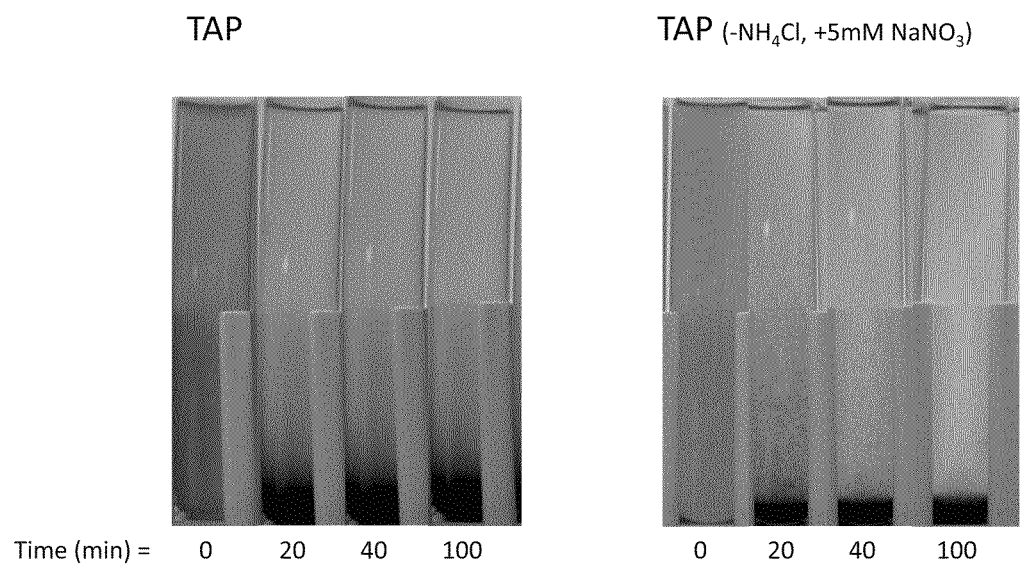
FIG. 23 shows flocculation of two C. reinhardtii strains following minimization of nitrogen.

A variation of the method involves minimizing the amount of nitrogen in the media so that the culture will naturally begin starvation as it approaches saturation. Strains 21gr and 6145c were grown in TAP until approximately $2\text{-}6 \times 10^6$ cells/mL. Approximately $1 \times 10^8$ cells were centrifuged and resuspend in 1 mL of TAP-$NH_4Cl$. These were diluted 10,000 fold in TAP-$NH_4Cl$+5 mM $NaNO_3$. Saturation was reached after three days of growth under light. Sedimentation of 7.5 mL of the culture was observed in a 13×100 mm borosilicate disposable culture tubes over time. Results are shown in FIG. 23.

TABLE 1

Sequence Data

| SEQ ID NO | Codon-biased, Synthesized Gene Sequence | Sequence Description |
|---|---|---|
| 1 | atgacatgtgaattccctaggctcgagcagtgcgcctgaagaccattgctttcagcgccgccatcgaccgcgagcaga cgtttgacgccaaccaggtggtcatctacgacatcgtgattacgaaccacggcaacgctacgataactccaccggcct gttcaccgcgccggtggacggcatgtacagctttcaactgaacctgctcacgattaaggagaaggagggctggctgga gctcgtgcacaacggtcagctcaaggtgagcgtctacgcgaagcaggacagcacgtacgattcgtcgagcaactcggt catcatcaagatgaaggagggtgatcgggtgaacgtgcgggcccacaagaagtcgggtctgttcggccgcgacgacg agctgtacaacacgttctccggccacttcctgtccggcctgggcaccggcaccggtgactacaaggacgacgacgaca agtccggcgagaacctgtacttccagggccacaaccaccgccacaagcacaccggtgtcgactag | H. pomatia lectin |
| 2 | atgacatgtgaattccctaggctcgagcaacggtgcggggagcaggggtccaacatggagtgccccaacaacctgtgc tgctcgcagtacgggtactgcggcatgggcggcgactactgcggcaagggctgccagaacggcgcctgctggacctc caagcgctgcggttcccaggccggtggcgccacctgacaccaacaaccagtgctgctcccagtatggctactgcggctt cggcgcggagtactgcggtgcgggctgccagggcggcccctgccgcgctgacatcaagtgcgggtcgcaggctggc ggcaagctgtgcccgaacaacctctgctgcagccagtggggcttctgcggtctgggcagcgagttttgcggtggtggtt gccagagcggcgcctgcagcacggacaagccgtgcggcaaggacgctggcggccgggtctgcactaacaactattg ctgctccaagtggggctcctgcggcatcggcccgggctattgcggtgcgggctgccagtcgggcggctgcgacggcg gcactggcaccggtgactacaaggacgacgacgacaagtcgggcgagaacctgtacttccagggtcacaaccaccgc cacaagcacaccggtgtcgactga | T. vulgaris lectin |
| 3 | ttggttctcgatcccgcgaaattaatacgactcactatagggaattgtgagcggataacaattcccctctagaaataatttt gtttaactttaagaaggagatatacatatgacatgtgaattcatgaaagctactaaactggtactgggcgcggtaatcctgg gttctactctgctggcaggttgctccagcaacgctaaaatcgatcagggaattccaggcaaccgtatgttggctttgaaat gggtacgactggttaggtcgtatgccgtacaaaggcagcgttgaaaacggtgcatacaaagctcagggcgttcaactg accgctaaactgggttacccaatcaactgacgacctagacatctacactcgtctgggtggtatggtatggcgtgcagacact aaatccaacgtttatggtaaaaaccacgacaccggcgtttctccggtcttcgctggcggtgttgagtacgcgatcactcct gaaatcgctaccgtctggaataccagtggaccaacaacatcggtgacgcacacaccatcggcactcgtccggacaac ggtattaactcgagcagcgtgcctggcgatccgcgcgtgcctcgcagctggacggagccctttccgttctgcggtacag gcgactacaaggatgatgacgacaagtcgggcgagaacctctattccagggtcacaaccaccgccacaagcacccta ggctcgagatgctgtttgtcactattattcccctgggtctgctggctattgtgcacggccagtgcgccctgaagaccattgct tcagcgccgccatcgaccgcgagcagacgtttgacgccaaaccaggtggtcatctacgacatcgtgattacgaaccacg gcaacgctacgataactccaccggcctgttcaccgcgccggtggacggcatgtacagctttcaactgaacctgctcac gattaaggagaaggagggctggctggagctcgtgcacaacggtcagctcaaggtgagcgtctacgcgaagcaggac agcacgtacgattcgtcgagcaactcggtcatcatcaagatgaaggagggtgatcgggtgaacgtgcgggcccacaag aagtcgggtctgttcggccgcgacgacgagctgtacaacacgttctccggccacttcctgtccggcctgggcaccggca ccggtgtcgactag | LppOmpA-H. pomatia lectin |

TABLE 1-continued

Sequence Data

| SEQ ID NO | Codon-biased, Synthesized Gene Sequence | Sequence Description |
|---|---|---|
| 4 | atgacatgtgaattcatgaaagctactaaactggtactgggcgcggtaatcctgggttctactctgctggcaggttgctcca gcaacgctaaaatcgatcagggaattccaggcaacccgtatgttggctttgaaatgggttacgactggttaggtcgtatgc cgtacaaaggcagcgttgaaaacggtgcatacaaagctcagggcgttcaactgaccgctaaactgggttacccaatcac tgacgacctagacatctacactcgtctgggtggtatggtatggcgtgcagacactaaatccaacgtttatggtaaaaacca cgacaccggcgtttctccggtcttcgctggcggtgttgagtacgcgatcactcctgaaatcgctaccgtctggaatacca gtggaccaacaacatcggtgacgcacacaccatcggcactcgtccggacaacggtattaactcgagcagcgtgcctgg cgatccgcgcgtgcctcgcagctggacggagccctttccgttctgcggtacaggcgactacaaggatgatgacgacaa gtcgggcgagaacctctatttccagggtcacaaccaccgccacaagcaccctaggctcgaggtgacttcctacacgctg aacgaggtggtgccgctgaaggacgtggtgcccgagtgggtgcggatcggcttcagcgccaccacgggcgctgagtt cgccgcccacgaggtgcactcctggtccttttcacagcgagctgggtggcaccagcagctccggcacgggcaccggtg tcgactga | LppOmpA-truncated L. culinaris lectin |
| 5 | atgacatgtgaattccctaggctcgagactgagactacgtcgtttagcattaccaagttttcccctgatcagcagaacctga tcttccagggcgacggctacaccacgaagggcaagctgaccctgacgaaggccgtcaagagcactgtgggccgggc gctgtatagcaccccccattcacatttgggaccgcgacaccgggaacgtggccaacttcgtgacctccttcaccttcgtgat cgacgccccagctcgtacaacgtggcggacggcttcaccttcttcatcgcgcctgtggacacgaagccgcagacgggg cggcgggtatctgggcgtcttcaactcgaaggagtacgacaagacttcgcagaccgtggccgtggagttcgatactttct acaacgcggcctgggaccccagcaacaaggagcgccacattggcatcgacgtgaactcgatcaagtcggtgtccacc aagagctggaacctgcagaacggcgagcgcgcgaacgtggtcatcgcgttcaacgccgccacgaacgtcctgaccgt caccctgacctaccctggtgtcgacgattacaaggatgatgacgacaagagcggcgagaacctgtactttcagggt gcacaaccatcgccacaagcacggcatcaacagctcgagcgtgcccgacccgtcgtgcctcggtcgtgggacc gagccgttccccttctgcgcgtacaggcgtattttcattggatgattatgatgcaaaagacaatagtgaatcatcaataggtaa tttagctcgtgtaatacctagaatgggaagggagttaattaatgattatgaagaaatcccttggaggagttggaagatgaa gcggaagaagaacgtcgccaagcaacgcaattccactccaaaagtcgtaaccgtagagctatatcatcggaaccatcat ctgatgaagatgcatctgaatcggtttccacatcagacaaacaccctcaagatataacggaacttcatgaaaaagttgaga cggcgggtttacaaccaagagcgcgcagccgcgaacccaagccgccgcgcaagccgatgcagtcagcaccaatgc taactcggctttatctgacgcaatggcaagcacgcaatctatcttgttggatacaggtgcttacttaacacggcacattgca caaaaatcacgcgctgatgccgaaaaaaacagtgtttggatgtcaaacactggttatggccgtgattatgcttccgcacaa tatcgccggtttagttcgaaacgcacgcaaacacaaatcggcattgaccgcagcttgtccgaaaatatgcagataggcg gagtattgacttactctgacagtcagcatacttttgatcaggcgggcggcaaaatacttttgtgcaagccaacctttatggt aagtattatttaaatgatgcttggtatgtggccggcgatattggtgcggcagcttgagaagccggttacaaacgcagcaa aaagcaaactttaaccgaacaagcatccaaaccggccttactttgggcaatacgctgaaaatcaatcaattcgagattgtc cctagtgcgggtatccgttacagccgcctgtcatctgcagattacaagttgggtgacgacagtgttaaagtaagttctatgg cagtgaaaacactaacgccggactggattttgcttatcggtttaaagtcggcaaccttaccgtaaaaccttgttatctgc agcttactttgccaattatggcaaaggcggcgtgaatgtgggcggtaaatcctcgcctataaagcagataatcaacagca atattcagcaggcgtcgcgttactgtaccgtaatgttacattaaacgtaaatggcagtattacaaaaggaaaacaattggaa aaacaaaaatccggacaaattaaaatacagattcgttttctaa | L. culinaris lectin-β-Auto-transporter |
| 6 | atgacatgtgaattccctaggctcgagcaacggtgcggggagcaggggtccaacatggagtgccccaacaacctgtgc tgctcgcagtacgggtactgcggcatgggcggcgactactgcggcaagggctgccagaacggcgcctgctggacctc caagcgctgcggttccaggccggtggcgccacctgcaccaacaacagtgctgctcccagtatggctactgcggctt cggcgcggagtactgcgtgcgggctgccaggcggccgtcgggcgcgctgacatcaagtgcgggtcgcaaggctggc ggcaagctgtgcccgaacaacctctgctgcagccagtgggcttctgcggtctgggcagcgagttttgcggtggtggtt gccagagcggcgcctgcagcacggacaagccgtgcggcaaggacgctggcggccgggtctgcactaacaactattg ctgctccaagtggggctcctgcggcatcggcccgggctatttgcggtgcgggctgccagtcgggcggctgcgacggcg gcactggcaccggtgtcgacgattataaggacgatgacgacaagagcggcgagaacctgtactttcagggtcacaacc atcggcacaagcacggtacaggcgccgctgctatctctcaaattggtgacggtcaaatccaagccactaccaaaaccac tgctgctgctgtttctcaaattggtgacggtcaaatccaagccactactaaaaccaaagctgctgctgtctctcaaattggtg acggccaaatccaagccaccaccaagactacctcagctaagactaccgctgcagccgtctcccaaattggtgacggtct aattcaagccaccactaaaaccaaagctgctgctgtctctcaaattggtgacggtcaaatccaagccactaccaaaacaac tgctgcagtctgtctctcaaattggtgacggtcaaatccaagccactactaaaaccactgctgctgctgtttctcaaattggtg acggtcaaatccaagccaccaccaatactactgttgctccagtctcccaaatcactgatggccaaatccaagccacaactt taacttcttga | Pir1b-H. pomatia lectin |
| 7 | atgacatgtgaattccctaggctcgagactgagactacgtcgtttagcattaccaagttttcccctgatcagcagaacctga tcttccagggcgacggctacaccacgaagggcaagctgaccctgacgaaggccgtcaagagcactgtgggccgggc gctgtatagcaccccccattcacatttgggaccgcgacaccgggaacgtggccaacttcgtgacctccttcaccttcgtgat cgacgccccagctcgtacaacgtggcggacggcttcaccttcttcatcgcgcctgtggacacgaagccgcagacgggg cggcgggtatctgggcgtcttcaactcgaaggagtacgacaagacttcgcagaccgtggccgtggagttcgatactttct acaacgcggcctgggaccccagcaacaaggagcgccacattggcatcgacgtgaactcgatcaagtcggtgtccacc aagagctggaacctgcagaacggcgagcgcgcgaacgtggtcatcgcgttcaacgccgccacgaacgtcctgaccgt caccctgacctaccctaactcctggagggagaagacgtgacttctacacgctgaacgaggtggtgccgctgaagga cgtggtgcccgagtgggtgcggatcggcttcagcgccaccacgggcgctgagttcgccgcccacgaggtgcactcct ggtccttttcacagcgagctgggtggcaccagcagctccggcacgggcaccggtgtcgacgattataaggacgatgac gacaagagcggcgagaacctgtactttcagggtcacaaccatcggcacaagcacggtacaggcgccgctgctatctct caaattggtgacggtcaaatccaagccactaccaaaaccactgctgctgctgtttctcaaattggtgacggtcaaatccaa gccactactaaaaccaaagctgctgctgtctctcaaattggtgacggccaaatccaagccaccaccaagactacctcagc taagactaccgctgcagccgtctcccaaattggtgacggtcaaattcaagccactaaaaccaaagctgctgctgtctc tcaaattggtgacggtcaaatccaagccactaccaaaacaactgctgcagtctgtctctcaaattggtgacggtcaaatcca agccactactaaaaccactgctgctgctgtttctcaaattggtgacggtcaaatccaagccaccaccaatactactgttgct ccagtctcccaaatcactgatggccaaatccaagccacaactttaacttcttga | Pir1b-L. culinaris lectin |

TABLE 1-continued

Sequence Data

| SEQ ID NO | Codon-biased, Synthesized Gene Sequence | Sequence Description |
|---|---|---|
| 8 | atgacatgtgaattccctaggctcgagcaacggtgcggggagcaggggtccaacatggagtgccccaacaacctgtgc tgctcgcagtacgggtactgcggcatgggcggcgactactgcggcaagggctgccagaacggcgcctgctggacctc caagcgctgcggttccaggccggtggcgccacctgcaccaacaaccagtgctgctcccagtatggctactgcggctt cggcgcggagtactgcggtgcgggctgccaggcggccccctgccgcgctgacatcaagtgcgggtcgcaggctggc ggcaagctgtgcccgaacaacctctgctgcagccagtgggggcttctgcggtctgggcagcgagttttgcggtggtggtt gccagagcggcgcctgcagcacggacaagccgtgcggcaaggacgctggcggccgggtctgcactaacaactattg ctgctccaagtggggctcctgcggcatcggcccgggctattgcggtgcgggctgccagtcgggcggctgcgacggcg gcactggcaccggtgtcgacgattacaaggatgatgatgacaagagcggcgagaacctgtacttccagggcgcaacc accgccataagcacggtacaggcgccgctgctatctctcaaattggtgacggtcaaatccaagccactaccaaaaccac tgctgctgctgtttctcaaattggtgacggtcaaatccaagccactactaaaaccaaagctgctgctgtctctcaaattggtg acggccaaatccaagccaccaccaagactacctcagctaagactaccgctgcagccgtctcccaaattggtgacggtca aattcaagccactactaaaaccaaagctgctgtctctcaaattggtgacggtcaaatccaagccactaccaaaacaac tgctgcagctgtctctcaaattggtgacggtcaaatccaagccactactaaaaccactgctgctgctgtttctcaaattggtg acggtcaaatccaagccaccaccaatactactgttgctccagtctcccaaatcactgatggccaaatccaagccacaactt taacttctgcaaccattataccatctccagctccagctccaattactaatggcactgacccagtaactgctgaaacatgcaa aagcagtggcacttttagaaatgaacttaaaagggtggtatctgactgacggtaaagtaagtaagttggttctatcgttgccaa cagacaattccaattcgatggtcctccaccacaagctggtgctatctatgctgctggttggtccatcaccccagaaggtaa cttggccatcggtgaccaggatacttttttaccaatgtttgtcaggaaacttctacaacttatacgatgagcacattggaactc aatgtaatgcagtccacctacaagctatcgatttgctcaactgttag | Pir1a-T. vulgaris lectin |
| 9 | atggccaagctgaccagcgccgttccggtgctcaccgcgcgcgacgtcgccgagcggtcgagttct TABLE 1-continued Sequence Data

| SEQ ID NO | Codon-biased, Synthesized Gene Sequence | Sequence Description |
|---|---|---|
| | cttggcttgatctttgcgttgcatcatgtatcctgttcgcagtggcggcgctacgatcacggttgtcaagaccggaaccacg acccagctgaagctgggcaacagcgtggtcagcgtggtcggggcggaggttgcgattggcagcaggtgggtgcacct gacctcttcattgccaccttcctgcagcgctgatgatggcttctttgcgacgttatcgacgtgcttaaaaacgcaacacaac aagtgccatcgccgcgagcctgcatgctgtgtttatggtgtcaacgcgccccatacccatgccatgcccctggtgtttg cagcgcgacgctcatcgtcatcgacggtgtcctggtgccgtccggcgtttccaccgtgacctcgggaggcggtggcgg cgccgcagcggcaactacgccgtccttcgtgctcatgctgtggagcgttgtggcggcagcgctgctgctagcattccag cgcctgcagtag | |
| 10 | atggccaagctgaccagcgccgttccggtgctcaccgcgcgcgacgtcgccggagcggtcgagttctggaccgaccg gctcgggttctcccgggacttcgtggaggacgacttcgccggtgtggtccgggacgacgtgaccctgttcatcagcgcg gtccaggaccaggtgagtcgacgagcaagcccggcggatcaggcagcgtgcttgcagatttgacttgcaacgcccgc attgtgtcgacgaaggcttttggctcctctgtcgctgtctcaagcagcatctaaccctgcgtcgccgtttccatttgcaggac caggtggtgccggacaacaccctggcctgggtgtgggtgccggcctggacgagctgtacgccgagtggtcggaggt cgtgtccacgaacttccgggacgcctccggggccggccatgaccgagatcggcgagcagccgtggggcgggagttc gccctgcgcgacccggccggcaactgcgtgcacttcgtggccgaggagcaggacgccccggtgaagcagaccctga acttcgacctgctgaagctggcggggacgtggagagcaaccgggcccccctcgacatggcgtctcatgccgcggcc cagagcgcttttcacagctgtggccactgcagcggacccgggcctcgacgactacaaggacgacgacgacaagtccg gcctcgaggtgacttcctacacgctgaacgaggtggtgccgctgaaggacgtggtgcccgagtgggtgcggatcggct tcagcgccaccacgggcgctgagttcgccgcccacgaggtgcactcctggtcctttcacagcgagctgggtggcacca gcagctccggcacgggcaccggtgactataaggacgacgacaagtgccgtgagaacctgtactttcagggcccac aaccaccggccacaagcacaccggtgtcgaacctgttccttttttacctcagccctccaactgagcggccttgtaacgttcttca acgctaccggaaggaacatcacgttattcgcgcccagtgatcaggttggtgcttgtacgtagctggagggcttctgattat caactcccctcgaaccctccactgaccccaacctacgacctcacacccatacgcggccaccgaaggcgctactagcg gcgctgccggcctgaacctgaactcagctggtgactaacagcagtgctcatgcgccaggctgctcatgtaccacg ctttcgtgccagcgaccaacaacgcctctgtccctcccggaatttcgtactacaacgcgttgaagtgaggcggggcgc gagtttagaaggttgacctggatgcggccacacgctcgcattgcagcctttcatgtttgtgagtacctcaatgttaggcc aaaaaccgcgccaacgtgccaacctacagcacggatggcagcgtcagcggcaaccagctggcgattacgaggacgg tgtcgggcggtctgcgggtcacctccatcggcagcgacgccaacgtgatcaaggtggaccttcccaactccgggtgag agagcgcgtggctggcggcgccaatgcgctggctccttcgcctatgtcaggatgagtgtcgtttcgttcgggactggat cgggtcgcggtgcatggggaagcggcacccggtagaacgtgtatgggcaagtggatgggtacccgaacagtctgcct ccgcgcgtcacacctcaactatctcctctagacatgtggcattgtattgtcgctgacaacaggtcccacggtagtgcacgtc gtggacgcggtgcttctcccgttctacccgtcagtgtactccgtgagttgcagtgcaagtgcgggcgcaggcgcaagct gcagaaaccaaacgggcaaggcgcatgctcggctcctgcagccacatatggcgagactgccttttcgcagcgc cgacctacatgaggcagcgacccaacacgttgcccaaccctgcgcctgacgtgcgccatgcaggcctgtggcgcgc acctctgcctgagcacgctggccgcgtggtcggctctgccagcgccagcctggtgtccaagctgcaggtcgtgtgt gtgttgagcgggtggtgaagatttggtggcgggctgggcacgccgccgttcttgggttacggcaagtgccgtgttttgc tgactggcggggagttgtcgcgctggctcgcgcctctctgcgcatcacagcgcccctgatggtgtcgcactgaagtggc gattgcgttccgtcctgggcatgttctacaggacactacgggtgtctacaccctcttgctccctacaatgcgtgagttgtg gttcagcacccactggttgtgccaggccgacaggccgacgttgcgtcaagtcgcgaaccgtgcgcggctcaagcatt gccctgaccggctttggattgccagcggctcctacgctgaccttccctgctgtggctcctccctcgtgtgcacagcg cctcacggcgcgcctggcccctccggcctcaacacgacgattgcgcagctggcggcgcagcgccctgctgcag tccatcctgtcgtaccacgtcgtgcccggcctgtacaacgcctctcgttccaccacacccatcaccgtcaccaccctg acgtatgcgctcgctgcatgcatgcgcacccagcgtgtgtgcgccaccgtgcagaggcaggcctcaaccttcagatcag tctgatcagtttgaccagttgcattccgacacacgacgatgccctggcatgcctcaatgcccccgctccgcagtggccaga agctgacgctggtgaaggacggcaacttcgctgtcggtgaagacggcgacggcatgacgcccaacattgctgcaggc gcgcgacctgccgtgcggcttcacggaccagtgagttggtcgcgcgagtgaccagcatagcacgggacaaggactcg tggcatcccgttgttcaggatgggtttgcaccggcgtaggagcccaaatccaacatgcacagctaacgcatttcacac tacacgtccaacctgtcaggggcacgttccgcgcgaccgtgccacgtgatcgacaaggtactcgtccctcccctgttacc tccgtggctgcgggcgctggcctgcgcaccgacgtcaacacactgctggcggccgtcaaggcggaggggtcctactc ggctgcgatcaacaggtgacttgcgggcaacggcgccgttacaaacgctatgcgcttactgcgtcttctcgggcacata ctgcgtccatttgactgcattacgaaggactggacttaccccagaattgttccctgcctgctgctgcatgccctgaaaccct cagcaccacattcaccggcacgcttctggcgccatcgactcggccttcacggcgctgctggcggccaatggcagcat cagcgccgcgcagctgctgggcaacaccacggcgctgaagaagatcctggacgtgagtgctcgtgctatgcaggcgt cctcaggccacagacctctatgtacagccagcgtgcctgacctttgtggctttctggctgtgttcaggcgacggtggtcac ggggtcggtgctgacggtggcgggtctcaccaacggccagaacattacccaccaggtggggcattagccattgggcctt gaggtgtccccacattgggtggttgccgctgcgcgcttttggtcattatgctgagtagaatgctatgctcttggcttgatcttt gcgttgcatcatgtatcctgttcgcagtggcggcgctacgatcacggttgtcaagaccggaaccacgacccagctgaag ctgggcaacagcgtgcagcgtggtcggggcggaggttgcgattggcagcaggtgggtgcacctgacctcttcattg ccaccttcctgcagcgctgatgatggcttctttgcgacgttatcgacgtgcttaaaaacgcaacacaacaagtgccatcgc cgcgagcctgcatgctgtgtttatggtgtcaacgcgccccatacccatgccatgcccctggtgtttgcagcgcgacgct catcgtcatcgacggtgtcctggtgccgtccggcgtttccaccgtgacctcgggaggcggtggcggcgccgcagcgg caactacgccgtccttcgtgctcatgctgtggagcgttgtggcggcagcgctgctgctagcattccagcgcctgcagtag | L. culinaris truncated lectin-Fas1 |
| 11 | atggccaagctgaccagcgccgttccggtgctcaccgcgcgcgacgtcgccggagcggtcgagttctggaccgaccg gctcgggttctcccgggacttcgtggaggacgacttcgccggtgtggtccgggacgacgtgaccctgttcatcagcgcg gtccaggaccaggtgagtcgacgagcaagcccggcggatcaggcagcgtgcttgcagatttgacttgcaacgcccgc attgtgtcgacgaaggcttttggctcctctgtcgctgtctcaagcagcatctaaccctgcgtcgccgtttccatttgcaggac caggtggtgccggacaacaccctggcctgggtgtgggtgccggcctggacgagctgtacgccgagtggtcggaggt cgtgtccacgaacttccgggacgcctccggggccggccatgaccgagatcggcgagcagccgtggggcgggagttc gccctgcgcgacccggccggcaactgcgtgcacttcgtggccgaggagcaggacgccccggtgaagcagaccctga acttcgacctgctgaagctggcggggacgtggagagcaaccgggcccccctcgacatggcgtctcatgccgcggcc cagagcgcttttcacagctgtggccactgcagcggacccgggcctcgacgactacaaggacgacgacgacaagtccg gcctcgaggtggagactattagcttttcctttttcggagtttgagcctggtaacgataacctgaccctgcagggtgctgccct cattacccagagcggcgtgctgcagctcactaagatcaaccagaacggtatgccggcttgggactcgacgggccgga ccctgtacacgaagcccgtgcacatgtgggacagcaccacggggaccgtgcttccttcgagactcgcttttcgttctcc | E. cristagalli lectin-Fas 1 |

TABLE 1-continued

Sequence Data

| SEQ ID NO | Codon-biased, Synthesized Gene Sequence | Sequence Description |
|---|---|---|
| | atcgagcagccctacacccgccctctcccggccgacggcctggtgttctttatgggccccaccaagagcaagccggcc<br>cagggctacggttacctgggcgtgttcaacaactccaagcaggacaacagctaccagaccctggcggtcgagtttgac<br>accttctcgaaccctgggaccgcctcaggtgccccacatcgggatcgacgtgaactcgattcgctcgatcaagaccc<br>agccgtttcagctggacaacggccaagtggcgaacgtggtgattaagtacgacgcccccagcaagatcctgcatgtggt<br>cctggtgtacccgagctccggcgccatctcacacgatcgccgagattgtggacgtgaagcaggtgctgccggactgggt<br>ggatgtgggtctgtcggggccactggcgcgcagcgggatgcggcggagacgcacgacgtgtactcgtggtccttcc<br>aggcttccctgccggaggggaccggcaccggtgactacaaggacgacgatgacaagtcgggcgagaacctgtacttt<br>cagggccacaaccaccgccacaagcacaccggtgtcgacctgttcctttttacctcagccctccaactgagcggccttgt<br>aacgttcttcaacgctaccggaaggaacatcacgttattcgcgcccagtgatcaggttggtgcttgtacgtagctggagg<br>gcttctgattatcaactccctcgaaccctccactgacccaacctacgacctcacacccatacgcggcccaccgaagg<br>cgctactagcggcgctgccggccctgaacctgaatcagtcccagctggtgactaacgcagtgctcatggcgccagtgct<br>catgtaccacgctttcgtgccagcgaccaacaacgcctctgtccctcccggaatttcgtactacaacgcgttgaagtgag<br>gcggggcgcgagtttagaaggttgacctggatgcggccacacggctcgcattgcagccttttcatgtttgtgagtacct<br>caatgttaggccaaaaccgcgccaacgtgccaacctacagcacggatggcagcgtcagcggcaaccagctggcgat<br>tacgaggacggtgtcgggcggtctgcgggtcacctccatcggcagcgacgccaacgtgatcaaggtggaccttcccaa<br>ctccgggtgagagagcgcgtggctggccggccaatgcgctggctccttttcgcctatgtcaggatgagtgtcgtttcgtt<br>gcggactggatcgggtcgcggtgcatggggaagcggcaccggtagaacgtgtatgggcaagtggatgggtacccg<br>aacagtctgcctccgcgcgtcacacctcaactatctcctctagacatgtggcattgtattgtcgctgacaacaggtccacg<br>gtagtgcacgtcgtggacgcggtgcttctcccgttctacccgtcagtgtactccgtgagttgcagtgcaagtgcgggcgc<br>aggcgcaagctgcagaaaccaaaccgggcaaggcgcatgctcggctcctgcgaccaaccatatggcgcagacctgc<br>ctttcgcagcgccgacctacatgaggcagcgaccccaacacgttgcccaacccctgcgcctgcacgtgcgccatgcagg<br>ctgtggcgcgcacctctgccctgagcacgctggccgcgctggtcggctctgccagcgccagctggtgtccaagctgc<br>aggtcgtgtgtgtgttgagcgggtggtgaagatttggtgggcgggctgggcacgccgccgttcttgggtacggcaag<br>tgccgtgttttgctgactggcggcgagttgtgcgcgtgctcgcgcctctggccgcatcacagcgcccctgatgggtg<br>cactgaagtggcgattgcgttccgtccgtcgggcatgttctacaggacactacggtgtctacaccgtctttgctccctacaat<br>gcgtgagttgtggttcagcacccactggttgtgccaggccgacaggccgacgttgcgtcaagtcgcgaaccgtcgcg<br>gctgcaagcattgccctgaccggctttggattgccagcggctcctacgctgaccttccctcgctgtggctccctccctcg<br>tgtgcacagcgccttcacggccgccctggccccctccggcctcaacacgacgattgcgcagctggcggcgcagcccg<br>ccctgctgcagtccatcctgtcgtaccacgtcgtgcccggcctgtacaacgcctcctcgttttccaccacacccatcaccg<br>tcaccaccctgacgtatggcttcgctgcatgcatgcgccacccagcgtgtgtgcgccaccgtgcagaggcaggcctcaa<br>ccttcagatcagtctgatcagtttgaccagttgcattccgacacacgacgatgccctggcatgcctcaatgccccgctccg<br>cagtggccagaagctgacgctggtgaaggacggcacttcgctgtcggtgaagacggccgacggcatgacggccaac<br>ctgctgcaggcgcgcgacctgccgtgcgcttcacggaccgagttggtcgcgcgagttgaccagcagcatagcgggg<br>acaaggactcgtggcatcccgttgttcaggatgggtttgcaccggcgtaggagcccaaatcccaacatgcacagctaa<br>cgcatttcacactacacgtccaacctgtcaggggcacgttccgcgcgaccgtgcacgtgatcgacaaggtactcgtcct<br>cccctgttacctccgtggctgcggcgctggccctgcgcaccgacgtcaacacactgctggcggccgtcaaggcgga<br>ggggtcctactcggctgcgatcaacaggtgacttgcggcaaccggccgcgttacaaaacgctatgcgcttactgccgctt<br>ctcgggcacatactgcgtccatttgactgcattacgaaggactggacttacccccagaattgttccccctgcctgtgctgcatg<br>ccctgaaaccctcagcaccacattcaccggcacgcttctggcgcccatcgactcggccttcacggcgctgctggcggc<br>caatggcagcatcagcgccgcgcagctgctgggcaacaccacggcgctgaagaagatcctggacgtgagtgctcgtg<br>ctatgcaggcgtcctcaggccacagaccctctatgtacagccaggcctgacctttgtggtgcttctggctgtgttcaggc<br>gcacgtggtcacggggtcggtgctgacggtggcgggtctcaccaacgccagaacattaccaccaggtggggcatt<br>agccattgggcttgaggtgtccccacattgggtggttgccgctgcggcttttggtcattatgctgagtagaatgctatgct<br>cttggcttgatctttgcgttgcatcatgtatcctgttcgcagtggcggcgctacgatcacggttgtcaagaccggaaccacg<br>accagctgaagctgggcaacagcgtgtcagcgtgctcggggcgaggttgcgattgacgcaggtgggtgcacct<br>gacctcttcattgccaccttcctgcagcgctgatgatggcttctttgcgacgttatcgacgtgcttaaaaacgcaacacaac<br>aagtgccatcgccgcgagcctgcatgctgtgttatggtgtcaacgcgcccataccccatgccatgcccctggtgttttg<br>cagcgcgacgctcatcgtcatcgacggtgtcctggtgccgtccggcgtttccaccgtgacctcgggaggcggtggcgg<br>cgccgcagcggcaactacgccgtccttcgtgctcatgctgtggagcgttgtggcggcagcgctgctgctagcattccag<br>cgcctgcagtag | |
| 12 | atggccaagctgaccagcgccgttccggtgctcaccgcgcgcgacgtcgccggagcggtcgagttctggaccgaccg<br>gctcgggttctcccgggacttcgtggaggacgacttcgccggtgtggtccgggacgacgtgaccctgttcatcagcgcg<br>gtccaggaccaggtgagtgacgagcaagccccggcagcagcggtgcttgacgatttgacttgcaacgtgccgc<br>attgtgtcgacgaaggctttttggctcctctgtcgctgtctcaagcagcatctaaccctcgctcgcgtttccatttgcaggac<br>caggtggtgccggacaacaccctggcctgggtgtgggtgcgcggcctggacgagctgtacgccgagtggtcggaggt<br>cgtgtccacgaacttccgggacgcctccgggccggccatgaccgagatcggcgagcagccgtggggcggagttc<br>gccctgcgcgaccgccggcaactgcgtgcacttcgtggccgaggagcaggacccccggtaagcagcagaccctga<br>acttcgacctgctgaagctggcggggacgtggagagcaacccggcccctcgacatgatgcggcggcaacacgc<br>tgcccccttgtgggcggtcacgtcttgatggtggtgctcgccttcgtcgcgagcgctaacgcgcagtgtgtacctg<br>gcggtatcttcaactgcctcgagcagtgcgccctgaagaccattgctttcagcgccgccatcgaccgcgagcagacgttt<br>gacgccaacaggtggtcatctacgacatcgtgattacgaacacggcaacgctacgataacctccaccggccgtgttca<br>ccgcgccggtggacgcatgtacagctttcaactgaacctgctcacgattaaggaagggggctggctggagctcg<br>tgcacaacggtcagctcaaggtgagcgtctacgcgaagcaggacagcacgtacgattcgtcgagcaactcggtcatca<br>tcaagatgaaggagggtgatcgggtgaacgtgcgggcccacaagaagtcgggtctgttcggccgcgacgacgagctg<br>tacaacgttctccggcacttcctgtccggcctgggcaaccggcgagcggtgactacaaggacgacgacaagtcc<br>ggcgagaacctgtacttccagggccacaaccaccgccacaagcacaccggtgtcgacctccctctccggccccacc<br>gtcctcctgccctccctccccggctcccccgtcacccgcacccttcgccagcaccccgagcccagggcccctc<br>gccgcccgccgagcccgcgagccctgcgccccgagccctgcgccgccgagcccggccccccgtccccg<br>ccctcgctcctccggccccgccatcgctcgcctccttccctcgccaccgtcccgccccaccctcgccccga<br>gccggccctccgtcgccagcccgccggccccccctcgcgtcccgcaccccgccccaccctcgcgcgcagcgccccga<br>ctcccagcgccgcccagccctcccccggtcccgcgtcaccgagcccgccctcccagcccgccctc<br>cttcgcccacgcctccgtccccagcccccgtgccgccagcccgcccgcctctcccgcccgccgtgccg<br>ccctcgccggcaccgcctccctgctccccggtgccgcctagccctgcccccgtcgcctcccgcagcgcc<br>ccttcccccagcccgccccccctcgccgtcccccgctccccgagcccgtgcccctttctccggcgccc | H. pomatia lectin-GP1 |

TABLE 1-continued

Sequence Data

| SEQ ID NO | Codon-biased, Synthesized Gene Sequence | Sequence Description |
|---|---|---|
| | cccagccccgcgccccct TABLE 1-continued Sequence Data

| SEQ ID NO | Codon-biased, Synthesized Gene Sequence | Sequence Description |
|---|---|---|
| | acgttcttcaacgctaccggaaggaacatcacgttattcgcgcccagtgatcaggttggtgcttgtacgtagctggaggg cttctgattatcaactcccctcgaacccctccactgaccccaacctacgacctcacacccatacgcggccaccgaaggc gctactagcggcgctgccggccctgaacctgaatcagtcccagctggtgactaacgcagtgctcatggcgccagtgctc atgtaccacgctttcgtgccagcgaccaacaacgcctctgtccctcccggaatttcgtactacaacgcgttgaagtgagg cggggcgcgagtttagaaggttgacctggatgcggccacacgggtcgcattgcagccttttcatgtttgtgagtacctca atgttaggccaaaaaccgcgccaacgtgccaacctacagcacggatggcagcgtcagcggcaaccagctggcgatta cgaggacggtgtcgggcggtctgcgggtcacctccatcggcagcgacgccaacgtgatcaaggtggaccttcccaact ccgggtgagagagcgcgtggctggcggcgccaatgcgctggctcctttcgcctatgtcaggatgagtgtcgtttcgttgc ggactggatcgggtcgcggtgcatggggaagcggcacccggtagaacgtatgggcaagtggatgggtacccgaa cagtctgcctccgcgcgtcacacctcaactatctcctctagacatgtggcattgtattgtcgctgacaacaggtccacgta gtgcacgtcgtggacgcggtgcttctcccgttctaccgtcagtgtactccgtgagttgcagtgcaagtgcgggcgcagg cgcaagctgcagaaaccagggcaaggcgcatgctcggctcctgcagccaacatatggcgcagacctgccttc gcagcgccgacctacatgaggcagcgacccaacacgttgcccaaccctcgcgcctgcacgtgcgccatgcaggctgt ggcgcgcacctctgccctgagcacgctggccgcgctggtcggctctgccagcgccagctggtgtccaagctgcagg tgcgtgtgtgtgttgagcgggtggtgaagatttggtgggcgggctgggcacgccgccgttcttgggttacggcaagtgc cgtgttttgctgactggcggcggagttgctgcgcgctctctggcgcatcacagcgccctgatggtgtgcac tgaagtggcgattgcgttccgtcctgggcatgttctacaggacactacggggtctacaccgtctttgctccctacaatgcg tgagttgtggttcagcacccactggttgtgccaggccgacaggccgacgttgcgtcaagtcgcgaaccgtgcgcggct gcaagcattgccctgaccggctttggattcccagcggctcctacgctgaccttccctcgctgtggctccctccctcgtgt gcacagcgccttcacggcgcgcctggccccctccggcctcaacacgacgattggcgacttgggcggcgcagcccgcc ctgctgcagtccatcctgtcgtaccacgtcgtgcccggcctgtacaacgcctcctcgttttccaccacacccatcaccgtc accaccctgacgtatggcttcgctgcatgcatgcgcacccagcgtgtgtgcgccaccgtgcagaggcaggcctcaacc ttcagatcagtctgatcagtttgaccagttgcattccgacacacgacgatgccctggcatgcctcaatgcccgctccgca gtggccagaagctgacgctggtgaaggacggccatcttcgctgtcggtgaagacggccgacggcatgacggccaacct gctgcaggcgcgcgacctgccgtgcgggcttcacggacccagtgagttggtcgcgcgagtgaccagcatagcacggga caaggactcgtggcatcccgttgttcaggatgggttgcaccggtaggagcccaaatcccaacgtgcacagctaac gcatttcacactacacgtccaacctgtcaggggcacgttccgcgcgaccgtgcacgtgatcgacaaggtactcgtccctc ccccgttacctccgtggctgcggcgctggccctgcgcaccgacgtcaacacactgctggcggccgtcaaggcggag gggtcctactcggctgcgatcaacaggtgacttgcggcaaccggcgccgttacaaacgctatgcgcttactgccgcttct cgggcacatactgcgtccatttgactgcattacgaaggactggacttaccccagaattgttccctgcctgtgctgcatgc cctgaaaccctcagcaccacattcaccggcacgcttctggcgcccatcgactcggccttcacggcgctgctggcggcc aatggcagcatcagcgccgcagctgctgggcaacaccacgcgctgaagaagatcctggacgtgagtgctcgtgc tatgcaggcgtcctcaggccacagcctctatgtacagccagctgcctgaccttgtggtgcttctggctgtgttcaggcg cacgtggtcacggggtcggtgctgacggtggcgggtctcaccaacggccagaacattaccaccaggtgggggcatta gccattgggcttgaggtgtccccacattgggtggttgccgctgcggcttttggtcattatgctgagtagaatgctatgctct tggcttgatctttgcgttgcatcatgtatcctgttcgcagtggcggcgctacgatcacggttgtcaagaccggaaccacga cccagctgaagctgggcaacagcggtggtcagcgtggtcggggcggagtgtgcgattggcagcaggtgggtgcacctg acctcttcattgccaccttcctgcagcgctgatgatgcttctttgcgacgttatcgacgtgcttaaaaacgcaacacaaca agtgccatgccgcgagcctgcatgctgtgttatggtgtcaacgcgccccataccccatgccatgcccctggtgtttgc agcgcgacgctcatcgtcatcgacggtgtcctggtgccgtccggcgtttccaccgtgacctcgggaggcggtggcggc gccgcagcggcaactacgccgtccttcgtgctcatgctgtggagcgttgtggcggcagcgctgctgctagcattccagc gcctgcagtag | |
| 15 | tctagatatgcacgccaggcttgcggttgaaggggcatcaggctcgaggcgagacgtcgagggcgtgggctctgtatg gctgggtaacggtacgtataattccaggtacaagctagagcagacggtggtgagaagcattagaagcattgtcccgagt gtggtggctagaatcccggcccacgaatcacagtgaatgggtacatgtacaggtgccccgcccagccccgctcctctg ctgcctctgatgcctcatgccaaaagtcctgacgcggcgccctcacatccccgtccgggtaatctatgagtttcccttatcg agcatgtacgcgatagtggacggggctcagggtgggggtgggtgggtgggagggcgttccttcagacaccctgga ggggtggctagaaaagcggccgcgcgccagaaatgtctcgctgccctgtcgcaataagcaccggctatattgctcagcg ctgttcggcgcaacgggggtcagcccttgggaagcgttggactatatggtaggggtgcgagtgaccccgcgcgacttg gagctcgatggccccgggttgtttggggcgtccgcctctcgcgctattctgagctggagaccgaggcgcatgaaaatgc attcgcttccataggacgctgcattgtggcttgaaggttcaagggaagggttcaaacgaccccgccgtacgaactttgtc gggggcgctcccggcccgggtcttgtgcgcgcattagggcttcgggtcgcaagcaagacgatacaggaaccga ccaatcgatagtcttgtgcgaccgtgcacgtgtcagcaatagttaggtcgataaccacgttgaacttgcgtctctcttcgt ggcgcctcctgcttggtgctccacttcacttgtcgctatatagcacagcgttgaaagcaaaggccacactaatacagccg ggctcgagagtccgtctgcgtttgcattgttggccaagggctgctttgtagccaaagccatacacgaagcttcacttgatta gctttacgaccctcagccgaatcctgccagtatgaccgttgccgagcagcccgtggcactcgtgcccagcggcaaggt gcaggcgcccgacgctatcgtatcgtcaaggcggtcgagctcggcgctcgctatgagcctccgctctcgcccgaggatgc cgactggtcgcagcacgttcttccctcagctgtggacaagcggcgaccaggacacgcccgacaactgggtcgggcgcg accccgcatcctgcgcctcaccggccggcaccgctcaactgcgagccgcccatgtccgtgctcatgcaggtgagg gggatttgcagggggaggcgagcttgaggttaggttagtgaacaaagagcagaggagggaactgacagccatggct cgaagctggctgggttgataatttagggagaattatgcggcggtggttggcggtgggggttgggggtggcgtggtttgag gcctggggcctggggcgaggggcggggttaacgggtgacggcaggctgggcgtacgtggagacgcgtcaacccac agtccagctacagctcgtcctcactgaccatctcccgctctcctcttcccctccaatcccccaaaccaaccaacccctaca caaaccaacagtacggtttcatcacgccgccggccgtacttcgtgcgcaaccacggcgccgcgccgcgcatccgct gggatgagcaccgcatcgagatcaacagcgcggttcaacaagccgttgacttttgaccatgacgagctggtggcgtgc cctccgtcaccttcccggtgacgctggtgcgctggcaaccgccgcaaggaggagaacatgcgaagaagagcattg gcttcaactggggccccttgtgccaccagcaccacctactggacgggcgtgcggctgcgcgacctgttgcagcacgcc gcatcaaggtgtgtgtgtgtgtgtgtgtatagctgacagggggttgtaaataccagcccaaataaaccaaccagtggg ggggtgaatgggtgatgtgcccgagccaataagtcccaagagtcaaggagtcgtcaccccaaccagaatgcagcg cgagctccgctataaccgtgggaagaggggggaacgagagaggggacgagggtgggtgatggcaggggagcaggag ggatggaggggaaggaaggaggggaggagggaagcagagcgcgtggttgatggcggggcgaggaattgc aagacaggggcttgatgtggcgtggtgtgagtgcatgtatgcctgtgtgggaacgcaagcacatttccctgatccccgcc acccgccttgcttctcccccattcccacgcctgctgctgcagacgccggccgagggcgcccgcttcgtgtgcttccgcgg ccccaaggggcgagctgccacgtggcgaggacggctcgtacggcacctctctgacgtacgccaaggccatggacccc | Nit-2A-H. pomatia lectin |

TABLE 1-continued

Sequence Data

| SEQ ID NO | Codon-biased, Synthesized Gene Sequence | Sequence Description |
|---|---|---|
| | gcctcggacgttatcatcgcatacaagcagaaccacaggtgtgtgcgtgtgcgtatgtgtgtgtgtgtgtgtgtgtgt | |
| | gtgtgtgtctctgtgtgtgcgtgtgtgaaagagcgaaaggcaaagaataggctgtgcgtgtgcgtgtgtgttcgagcgca | |
| | caaggcaaacactaggctgtgtgtgtttgtgtgcgcgtgtgtcgggggcggggcgcggggagggcagcgggagg | |
| | ttggcgctaggctgggcactgggtcgcacgggtcggaggcctggagctcgtccgaatggcgatggcgacggatgcgc | |
| | aagattgccgcacagaatagccgtcgtcgccgtgctgctcagcttcctcacccctccctccctccctcccgctcctcccc | |
| | gccccctcccgcctgctgcctgctgcctgcgcaggtggctgacgcccgaccacggcttcccggtgcgcatcatcatccc | |
| | gggcttcatcggcggccgcatggtcaagtggctgagcgagatcaccgtcatggacacggagtcgcaggtgcgtgggc | |
| | gtgtgggtttcgagaatgcttttaaggctaacaatgcgaagccatcaagccagcgagcacaacgtgtgtgtatgtagttgt | |
| | ctgggtgtgtgcgggcgaattgattcaggccgatgggctggcatgtagctcccagcctggcatcaaagcttgtggggcg | |
| | taactatgcttacacgcttcggccctaccacgataccccttgtaacctgtgccgccactccctctccatcccccccccaaaac | |
| | acacacccctacacacacagaacttctaccacttcatggacaaccgcgtgctgcccagccacgtggacgaggagctgg | |
| | ccaagaaggagggtgagcgcggggggagagccgtggcgtgtattgggagagcacagggtaggaaacaggga | |
| | aagatttccgcagaaatcttgtgtgtgtgcatgtgaccgccatcattcgaacccgtgtcatccccgttccgaagtccccgtc | |
| | ctgaaactcgccgtatacacgcgcgcaggctggtggtacaagcccgagttcatcatcaacgacctcaacatcaacagc | |
| | gcgatggctcggccctggcacgacgagctggtccccgctggacgccaaccgccctacaccatcaagggttacgccta | |
| | cgccggtgagcagcaacaacagcgataatgacaagcgggggcagcgatgctgcctagcgagcgagtgagagag | |
| | ccaacgtcgttggtttcgggccgtttggtcgtggcactggcaggcatcatacccgtacatgcgatttaggacgtgtggaac | |
| | gggacacgtgtgagcggctagttaagtaacggcaggactgaagatgaggatgacgaagtatatttaagttatttgctggc | |
| | gttggtctgtgtcgtcatcctcatcatgtgcaggcggcggccgaagatcatccgctgcgaggtctcgctggacgacgg | |
| | caagacctggcgcctgggcgacatccagccgcttcgaggagcccaacgagtacggcaagcactggtgctgggtgcact | |
| | ggacgctgaggtgaggcgccgagcgaggaggagtgggcgcctgtgggcgaaatgggcgatgtcggttgggatg | |
| | gcgggatgggcctttgcgtccctccagcccacgaccccactgcttcgctctgcccccccccccaaaaaaacacaggt | |
| | gaacacgtttgacttcctgtccgccaaggaggtgctgtgccgcgcctgggatgagaccatgaacacgcagccggcggt | |
| | gatcacctggaacctgatgggcatgaacaactgctacttccggtgagcgtgtgtgtgcgtgtgcggtggaaggggg | |
| | gaggcggcgatgagggaggcggcgagaggcgccttttgtcaatgttcagcatcgcagcgccgctcatcgcatttcc | |
| | ccgaacacctgcgtgacagccctggttccacacgtcggcccgcccctccccacccccatcccactaaactaatcatgaat | |
| | gtccccacgtaacacgcgcagcatcaagatccacccggaggtggacccagccacgggcgtcatgggcctgcgcttc | |
| | cagcacccggcccccgtggagctgggcgacaagggcaacatgggctggcgcgaggaggacaacctggtggcgca | |
| | ggcctggcgcgcggcgcgacggcggaggcgcgagggcaccgccgcgccgctccggcgggcgctg | |
| | gcgaatggcggccccaagcagtacacgctggaggaggtggcggagcacgcgagcgaggagagctgctggttcgtg | |
| | cacgagggcgggtgaggagagcggatggcgtggtggctggtctggtggctggtctggggctaggggtttgtggttga | |
| | ggttgtaggaagggcgagaggcgtggttgtgggtacgtgcgtgcccagcagctgcaccccaacccgtgctgacgtgc | |
| | acacgaaaccctgaaccaccctggaccccagctttctaacccctttcaccccccccgccctcccgcctccgctcc | |
| | caggtgtacgacgccacgccctacctgaatgaccaaccgggtggcgccgagtccatcctgatcactgcgggcgcgga | |
| | cgccacagacgagttcaacgccatccacaggtgggtaggggggcgagaacgtgtgtgtgcatgtgttttgtgcgtgtgtg | |
| | attggtgttttggggcgtgtacgagagaggggacgttttgcggggctaggatcagcggcaggcgtgtataagggtcc | |
| | gcgcatggcgtggcatccaacccaccgtcccatacaccaccaccgcacaccacgtccccatcccatctcaccccatctcc | |
| | ccacctgcgcccccacatcccccacacacagctccaaagcaaggccatgctggccagtactacatcggtgacctcg | |
| | tggcatcaaaaccagcaaccgccaacggcacggcaaccgcaacggcaacggcacggcaactgccaacggcaccg | |
| | cggcggcggcgccgccgccgaccctctggtttgtgctgacgggtcgcgccaaggtgaagctaccgctggtggagcg | |
| | gattgagctcaaccgcaacacgcgcatattccggttcggcctgcctcgccggacaccgcatcggtgggtgtgtcg | |
| | cgcgcgttatgatactaatgatacggtagtacgcacgtcttggctgccctgctgagtgtgtgccttgatttgtgtgggggaa | |
| | gggggcaagaacaagagcagccagcagaagggaaggagcgggctgacttcgtgtcggttgcgcgtccgcggcac | |
| | cactcactggccaccactcactgcacctcccaccccctccctccccgatgcgcaggcctgccggtgggcaagcacg | |
| | tgttcgtgtacgcgcaggtgggcggcgagaacgtgatgcgcgccatcagcgggcagcgaggagaaggg | |
| | ccggctggacatgctcatcaaggtgcgtgtatgtgtgtgtgtgtgtatgtgtgagggacgtgtgtgcgcctgtgtgtggggt | |
| | ggggacgtgtgtgcatgtgtgtgtaggtgttttctggtgcgtcattcatctttttgtaccgtgtgtgcccctgaccgcgccat | |
| | gccccacaccccacaatcccacctgacccccacacaccgggcgagcacgcgtcctaccccgagggcggcaagatga | |
| | gccagcatttcgactcgctcgccatcggcgactgcctggagttcaaggggccgctggggcacttcgtgtacaacggcc | |
| | gcggaagctacacgccaacggcaaggtgcgcgcaacaggaacggcgtcctgtagccgcgagaatgagtaagcc | |
| | taccacacaagcacatttaaatgcacacacattgtggtgagcttcttacggcacattgtcacacacgctagatagctaaca | |
| | cacacacacccctacctccctgcaggtgaccaagcacgccagtcacatgtcgtttgttgcgggcggcacgggcatcac | |
| | gccctgctacgcggtcatcaaggccgcactgcgcgaccccgaggacaacaccaagtgagcagcggcggcggcggg | |
| | gggaagcgggaggagaagcggcctcattgccgttggctgttgactgatgacacgctttgctgccgccgtatcaca | |
| | gtgccatagcatagcaaggcagtggatgggcattggctacagccagggactaaagggccacacgcacgtcccggca | |
| | catacacccgcgcccacacctgtgtccatcatccatcacgcacacccactctgacaccaacacaccaacacacacccc | |
| | cacaaccccctttcccacctgcaggctggcgctgctgttcgccaacacacacgaggacgacattctgctgcgcgaggag | |
| | ctggacgagctcgcaaacaaccaccccgagcgcttccggctgtggtgagtgcgcaccgggggggccacacgtacgg | |
| | cgcgcgcagccgcagctttggcttcgccttccgtcccagcctgagccaaccgtcaacgaaccaaccaacaccgaaccc | |
| | ctccccaccccctcccgccatcctcaggtacacggtgtcacagcccaaggacgcggcgacctggaagtacgacgtg | |
| | gggcgtgtgagcaaggacatgttcacggagcacctcttcgccagcacgggcgaggactgcctcagcctcatgtgcgg | |
| | gccgcacggcatgatcgagcactgctgccgtcctcgtgaggccatgggctacagcaaggaccgccagatccagtt | |
| | cgcccggtgaagcagaccctgaacttcgacctgctgaagctggcgggcgacgtggagagcaacccgggcccctc | |
| | gagcagtgcgccctgaagaccattgctttcagcgccgccatcgaccgcgagcagacgtttgacgcaaccaggtggtc | |
| | atctacgacatcgtgattacgaaccacggcaacgcctaccgataactccaccggcctgttcaccgcgccggtggacggc | |
| | atgtacagcttttcaactgctcacgattaaggagaagaggggctggctgagctcgtgcacacgaccgtcagcagctca | |
| | aggtgagcgtctacgcgaagcaggacagcacgtacgattcgtcgagcaactcggtcatcatcaagatgaaggagggta | |
| | atcgggtgaacgtgcgggcccacaagaagtcggtctgttcggccgcgacgacgagctgtacaacacgttctccggcc | |
| | acttcctgtccggcctgggcaccggcaccggtgactacaaggacgacgacgacaagtccggcgagaacctgtacttcc | |
| | agggccacaaccaccgcacaagcacaaggtgtcgactagggatctcgctagagattgtggccacggttggatca | |
| | tgcgaccagcaggattggatccgaatccaggcatctgggcgtatgccagggcaggggcaggtggcagcgctcgtgg | |
| | gagcgtgtgtgagccggataagggctggcacaggccacggccgcagcggccttttgtgcagtttgacgacgaagtgt | |
| | gcgtctgtgtggttgtgtgtgagagctaggcaggaccgcagggtcagacagagtgcgcccggcttggctgcggcgca | |
| | ctgggacgcgttggcagtttaaaacctgcgctgaggggacaaacgagtttggcaacagtaggcagttaaaagatagaat | |
| | gtgtaggtcagtttcccagtgggcaaatgagttgtgcaagcctgcaaacggcaggaagcatggcaaggatattactgatt | |

TABLE 1-continued

Sequence Data

| SEQ ID NO | Codon-biased, Synthesized Gene Sequence | Sequence Description |
|---|---|---|
| | gactgcagcaggggatagcagtagtggcacagcagagtgcccgagagagtgtgtgcacgtgctagttttggagtcagg<br>caccgccgttgagatgatgtattgatgacgcagcatttcatgtgacatagggaggcttttccatgcggttattatattatgtca<br>ggaaagtgcctgacagcgtttagcgcgtggggagaagtacgaccctccgtgggctgaacccacgttagggcgtgggtt<br>ggtcaggagggtgggtgccatgcatgaagcagagggccggggcgttagcccgttttggtgagagcttgtttgatgcaat<br>gcgatacataatcataagggggttttggcgcgtgagagtgcgacctgtgtatggcagcacgccatcggtgccaaccggc<br>gaaggtgcaggaggtgcaggtaaagctacatatagacacccctgccgcacagttgtaaattaagcaagcgacttgcat<br>tgtgtccatcactttgtgcagcaggcaggcaagggcaggtgctgccatgggctggcacggcgtggggcaacaaggg<br>ggcttagactcccaggggcgaccagtcgagccagggccgcaaggaccatggagagctgctagtgccccagggcg<br>ccaggccgcaacagcagttgggcggccagatggcagaccgcgaatgggagcccttggctgtaagtcgggctgcgag<br>aggagtttacctcgactgtggccgggaagaggggcgctgggcaagagtcggactagggagtgcgcgactgaaacg<br>cgcggggcactgcgcggggacacaggcgcggtcaaagcacctgtgtacctcgcgagtagatagcagtttagcgcatg<br>tccttgataatggtggagtctctcagcgaccaaagaagcgacttcagagcgaccggcccactaacggtcacacccgaac<br>ggccgctccctcgttttcggtcgcacagccgctatagaagtcgcaagtagcaaacactaatgttgcttttacagcgacaag<br>tgaaacgggttggttgaagagaattc | |
| 16 | atgacatgtgaattcatgaaagctactaaactggtactgggcgcggtaatcctgggttctactctgctggcaggttgctcca<br>gcaacgctaaaatcgatcagggaattccaggcaacccgtatgttggctttgaaatgggttacgactggttaggtcgtatgc<br>cgtacaaaggcagcgttgaaaacggtgcatacaaagctcagggcgttcaactgaccgctaaactgggtaccaatcac<br>tgacgacctagacatctacactcgtctgggtggtatggtatgcgtgcagacactaaatccaacgtttatggtaaaaacca<br>cgacaccggcgtttctccggtcttcgctggcggtgttgagtacgcgatcactcctgaaatcgctacccgtctggaatacca<br>gtggaccaacaacatcggtgacgcacacaccatcggcactcgtcgggacaacggtattaactcgagcagcgtgcctgg<br>cgatccgcgcgtgcctcgcagctggacggagccctttccgttctgcggtacaggcgactacaaggatgatgacgacaa<br>gtcgggcgagaacctctatttccagggtcacaaccaccgccacaagcaccctaggatgaaatacctattgcctacggca<br>gccgctggattgttattactcgcggcccagccggccatggccgaggtgcagctgttggagtctggggggaggcttggtac<br>agcctggggggtccctgagactctcctgtgcagcctctggattcacctttagcagctatgccatgagctgggtccgccag<br>gctccagggaagggctggagtgggtctcatggatttcgggactgttcgcggacagactacgcagactccgtgaag<br>ggccggttcaccatctccagagacaattccaagaacacgctgtatctgcaaatgaacagcctgagagccgaggacacg<br>gccgtatattactgtgcgaaaaaggcgcagaagtttgactactggggccagggaaccctggtcaccgtctcgagcggtg<br>gaggcggttcaggcggaggtggcagcggcggtggcgggtcgacggacatccagatgacccagtctccatcctccctg<br>tctgcatctgtaggagacagagtcaccatcacttgccgggcaagtcagagcattagcagctatttaaattggtatcagcag<br>aaaccagggaaagccctaagctcctgatctatgctgcatccagttttgcaaagtggggtcccatcaaggttcagtggcag<br>tggatctgggacagatttcactctcaccatcagcagtctgcaacctgaagattttgcaacttactactgtcaacagagttaca<br>gtaccctaatacgttcggcaagggaccaaggtggaaatcaaacgggcggccgcacatcatcatcaccatcactaa | LppOmpA-scFv5 |

What is claimed is:

1. A method of flocculating a photosynthetic microalga, comprising:
    a. expressing an exogenous nucleic acid encoding a first flocculation moiety as an external cell surface component of a first photosynthetic microalga, wherein said first flocculation moiety is a carbohydrate binding protein comprising a cell surface targeting signal; and
    b. contacting said microalga with a second flocculation moiety, wherein said second flocculation moiety interacts with said first flocculation moiety thereby flocculating said microalga.

2. The method of claim 1, wherein said carbohydrate binding protein is a lectin.

3. The method of claim 1; wherein said carbohydrate binding protein is selected from at least one of the group consisting of DC-SIGN, dectin-1, dectin-2, HECL, langerin, layilin, mincle, MMGL, E-selectin, P-selectin, L-selectin, DEC-205, Endo 180, mannose receptor, phospholipase A2 receptor, sialoadhesin (siglec-1), siglec-2, siglec-3, siglec-4, siglec-5, siglec-6, siglec-7, siglec-8, siglec-9, siglec-10, siglec-11, and galectins.

4. The method of claim 1, wherein said flocculation moiety is a lectin, carbohydrate, polysaccharide side chain of a glycoprotein, or glycopeptide.

5. The method of claim 1, wherein said nucleic acid further comprises a regulatory element, said element comprising a constitutive promoter, a light-inducible promoter, a quorum-sensitive promoter, temperature-sensitive promoter, a salt sensitive promoter or a nitrogen concentration responsive promoter.

6. The method of claim 1, wherein said second flocculation moiety is present as an external cell surface component of a second photosynthetic microalga.

7. The method of claim 6, wherein said second microalga is the same species as said first microalga.

8. The method of claim 6, wherein said second microalga is a different species as said first microalga.

9. The method of claim 1, wherein said second flocculation moiety is a protein.

10. The method of claim 9, wherein said protein is a glycosylated protein.

* * * * *

SEQUENCE LISTING

<160> NUMBER OF SEQ ID NOS: 16

<210> SEQ ID NO 1
<211> LENGTH: 534
<212> TYPE: DNA
<213> ORGANISM: Artificial Sequence
<220> FEATURE:
<223> OTHER INFORMATION: Codon biased H. pomatia lectin

<400> SEQUENCE: 1

```
atgacatgtg aattccctag gctcgagcag tgcgccctga agaccattgc tttcagcgcc      60
gccatcgacc gcgagcagac gtttgacgcc aaccaggtgg tcatctacga catcgtgatt     120
acgaaccacg gcaacgccta cgataactcc accggcctgt tcaccgcgcc ggtggacggc     180
atgtacagct tcaactgaa cctgctcacg attaaggaga aggagggctg ctggagctc      240 gtgcacaacg tcagctcaa ggtgagcgtc tacgcgaagc aggacagcac gtacgattcg     300
tcgagcaact cggtcatcat caagatgaag gagggtgatc gggtgaacgt gcgggcccac     360
aagaagtcgg gtctgttcgg ccgcgacgac gagctgtaca cacgttctc cggccacttc     420 ctgtccggcc tgggcaccgg caccggtgac tacaaggacg acgacgacaa gtccggcgag     480
aacctgtact ccagggcca caaccaccgc cacaagcaca ccggtgtcga ctag           534
```

<210> SEQ ID NO 2
<211> LENGTH: 642
<212> TYPE: DNA
<213> ORGANISM: Artificial Sequence
<220> FEATURE:
<223> OTHER INFORMATION: Codon biased T. vulgaris lectin

<400> SEQUENCE: 2

```
atgacatgtg aattccctag gctcgagcaa cggtgcgggg agcaggggtc caacatggag     60
tgccccaaca acctgtgctg ctcgcagtac gggtactgcg gcatgggcgg cgactactgc    120
ggcaagggct gccagaacgg cgcctgctgg acctccaagc gctgcggttc ccaggccggt    180
ggcgccacct gcaccaacaa ccagtgctgc tcccagtatg gctactgcgg cttcggcgcg    240
gagtactgcg gtgcgggctg ccagggcggc ccctgccgcg ctgacatcaa gtgcgggtcg    300
caggctggcg gcaagctgtg cccgaacaac ctctgctgca gccagtgggg cttctgcggt    360
ctgggcagcg agttttgcgg tggtggttgc cagagcggcg cctgcagcac ggacaagccg    420
tgcggcaagg acgctggcgg ccgggtctgc actaacaact attgctgctc caagtggggc    480
tcctgcggca tcggcccggg ctattgcggt gcgggctgcc agtcgggcgg ctgcgacggc    540
ggcactggca ccggtgacta caaggacgac gacgacaagt cgggcgagaa cctgtacttc    600
cagggtcaca accaccgcca caagcacacc ggtgtcgact ga                       642
```

<210> SEQ ID NO 3
<211> LENGTH: 1211
<212> TYPE: DNA
<213> ORGANISM: Artificial Sequence
<220> FEATURE:
<223> OTHER INFORMATION: LppOmpA-H. pomatia lectin fusion

<400> SEQUENCE: 3

```
ttggttctcg atcccgcgaa attaatacga ctcactatag gggaattgtg agcggataac     60
aattcccctc tagaaataat tttgtttaac tttaagaagg agatatacat atgacatgtg    120
aattcatgaa agctactaaa ctggtactgg gcgcggtaat cctgggttct actctgctgg    180
caggttgctc cagcaacgct aaaatcgatc agggaattcc aggcaacccg tatgttggct    240
ttgaaatggg ttacgactgg ttaggtcgta tgccgtacaa aggcagcgtt gaaaacggtg    300
catacaaagc tcagggcgtt caactgaccg ctaaactggg ttacccaatc actgacgacc    360
tagacatcta cactcgtctg ggtggtatgg tatggcgtgc agacactaaa tccaacgttt    420
atggtaaaaa ccacgacacc ggcgtttctc cggtcttcgc tggcggtgtt gagtacgcga    480
tcactcctga aatcgctacc cgtctggaat accagtggac caacaacatc ggtgacgcac    540
acaccatcgg cactcgtccg gacaacggta ttaactcgag cagcgtgcct ggcgatccgc    600
gcgtgcctcg cagctggacg gagccctttc cgttctgcgg tacaggcgac tacaaggatg    660
atgacgacaa gtcgggcgag aacctctatt tccagggtca caaccaccgc cacaagcacc    720
ctaggctcga gatgctgttt gtcactatta tttccctggg tctgctggct attgtgcacg    780
gccagtgcgc cctgaagacc attgctttca gcgccgccat cgaccgcgag cagacgtttg    840
acgccaacca ggtggtcatc tacgacatcg tgattacgaa ccacggcaac gcctacgata    900
actccaccgg cctgttcacc gcgccggtgg acggcatgta cagctttcaa ctgaacctgc    960
tcacgattaa ggagaaggag ggctggctgg agctcgtgca caacggtcag ctcaaggtga   1020
gcgtctacgc gaagcaggac agcacgtacg attcgtcgag caactcggtc atcatcaaga   1080
tgaaggaggg tgatcgggtg aacgtgcggg cccacaagaa gtcgggtctg ttcggccgcg   1140
acgacgagct gtacaacacg ttctccggcc acttcctgtc cggcctgggc accggcaccg   1200
gtgtcgacta g                                                         1211
```

<210> SEQ ID NO 4
<211> LENGTH: 801
<212> TYPE: DNA
<213> ORGANISM: Artificial Sequence
<220> FEATURE:
<223> OTHER INFORMATION: LppOmpA-truncated L. culinaris lectin fusion

<400> SEQUENCE: 4
atgacatgtg aattcatgaa agctactaaa ctggtactgg gcgcggtaat cctgggttct 60
actctgctgg caggttgctc cagcaacgct aaaatcgatc agggaattcc aggcaacccg 120
tatgttggct ttgaaatggg ttacgactgg ttaggtcgta tgccgtacaa aggcagcgtt 180
gaaaacggtg catacaaagc tcagggcgtt caactgaccg ctaaactggg ttacccaatc 240
actgacgacc tagacatcta cactcgtctg ggtggtatgg tatggcgtgc agacactaaa 300
tccaacgttt atggtaaaaa ccacgacacc ggcgtttctc cggtcttcgc tggcggtgtt 360
gagtacgcga tcactcctga aatcgctacc cgtctggaat accagtggac caacaacatc 420
ggtgacgcac acaccatcgg cactcgtccg gacaacggta ttaactcgag cagcgtgcct 480
ggcgatccgc gcgtgcctcg cagctggacg gagccctttc cgttctgcgg tacaggcgac 540
tacaaggatg atgacgacaa gtcgggcgag aacctctatt tccagggtca caaccaccgc 600
cacaagcacc ctaggctcga ggtgacttcc tacacgctga acgaggtggt gccgctgaag 660
gacgtggtgc ccgagtgggt gcggatcggc ttcagcgcca ccacgggcgc tgagttcgcc 720
gcccacgagg tgcactcctg gtcctttcac agcgagctgg gtggcaccag cagctccggc 780
acgggcaccg gtgtcgactg a 801

<210> SEQ ID NO 5
<211> LENGTH: 1962
<212> TYPE: DNA
<213> ORGANISM: Artificial Sequence
<220> FEATURE:
<223> OTHER INFORMATION: L. culinaris lectin-beta-Autotransporter fusion

<400> SEQUENCE: 5
atgacatgtg aattccctag gctcgagact gagactacgt cgtttagcat taccaagttt 60
tcccctgatc agcagaacct gatcttccag ggcgacggct acaccacgaa gggcaagctg 120
accctgacga aggccgtcaa gagcactgtg ggccgggcgc tgtatagcac ccccattcac 180
atttgggacc gcgacaccgg gaacgtggcc aacttcgtga cctccttcac cttcgtgatc 240
gacgccccca gctcgtacaa cgtggcggac ggcttcacct tcttcatcgc gcctgtggac 300
acgaagccgc agacgggcgg cgggtatctg ggcgtcttca actcgaagga gtacgacaag 360
acttcgcaga ccgtggccgt ggagttcgat actttctaca acgcggcctg ggaccccagc 420
aacaaggagc gccacattgg catcgacgtg aactcgatca agtcggtgtc caccaagagc 480
tggaacctgc agaacggcga gcgcgcgaac gtggtcatcg cgttcaacgc cgccacgaac 540
gtcctgaccg tcaccctgac ctaccctacc ggtgtcgacg attacaagga tgatgatgac 600
aagagcggcg agaacctgta cttccagggg cacaaccatc gccacaagca cggcatcaac 660
agctcgagcg tgcccggcga cccgcgcgtg cctcggtcgt ggaccgagcc gttccccttc 720
tgcggtacag gcgtattttc attggatgat tatgatgcaa aagacaatag tgaatcatca 780
ataggtaatt tagctcgtgt aatacctaga atgggaaggg agttaattaa tgattatgaa 840
gaaatcccct tggaggagtt ggaagatgaa gcggaagaag aacgtcgcca agcaacgcaa 900
ttccactcca aaagtcgtaa ccgtagagct atatcatcgg aaccatcatc tgatgaagat 960

-continued

```
gcatctgaat cggtttccac atcagacaaa caccctcaag ataatacgga acttcatgaa    1020
aaagttgaga cggcgggttt acaaccaaga gccgcgcagc cgcgaaccca gccgccgcg    1080 caagccgatg cagtcagcac caatactaac tcggctttat ctgacgcaat ggcaagcacg    1140
caatctatct tgttggatac aggtgcttac ttaacacggc acattgcaca aaatcacgc    1200 gctgatgccg aaaaaaacag tgtttggatg tcaaacactg gttatggccg tgattatgct    1260
tccgcacaat atcgccggtt tagttcgaaa cgcacgcaaa cacaaatcgg cattgaccgc    1320
agcttgtccg aaaatatgca gataggcgga gtattgactt actctgacag tcagcatact    1380
tttgatcagg cgggcggcaa aaatactttt gtgcaagcca acctttatgg taagtattat    1440
ttaaatgatg cttggtatgt ggccggcgat attggtgcgg gcagcttgag aagccggtta    1500
caaacgcagc aaaaagcaaa ctttaaccga acaagcatcc aaaccggcct tactttgggc    1560
aatacgctga aaatcaatca attcgagatt gtccctagtg cgggtatccg ttacagccgc    1620
ctgtcatctg cagattacaa gttgggtgac gacagtgtta agtaagttc tatggcagtg    1680 aaaacactaa cggccggact ggattttgct tatcggttta agtcggcaa ccttaccgta    1740 aaacccttgt tatctgcagc ttactttgcc aattatggca aaggcggcgt gaatgtgggc    1800
ggtaaatcct tcgcctataa agcagataat caacagcaat attcagcagg cgtcgcgtta    1860
ctgtaccgta atgttacatt aaacgtaaat ggcagtatta caaaaggaaa acaattggaa    1920
aaacaaaaat ccggacaaat taaaatacag attcgtttct aa    1962
```

<210> SEQ ID NO 6
<211> LENGTH: 1116
<212> TYPE: DNA
<213> ORGANISM: Artificial Sequence
<220> FEATURE:
<223> OTHER INFORMATION: Pir1b-H.pomatia lectin fusion

<400> SEQUENCE: 6

```
atgacatgtg aattccctag gctcgagcaa cggtgcgggg agcaggggtc caacatggag      60
tgccccaaca acctgtgctg ctcgcagtac gggtactgcg gcatgggcgg cgactactgc     120
ggcaagggct gccagaacgg cgcctgctgg acctccaagc gctgcggttc ccaggccggt     180
ggcgccacct gcaccaacaa ccagtgctgc tcccagtatg ctactgcgg cttcggcgcg     240 gagtactgcg gtgcgggctg ccagggcggc ccctgccgcg ctgacatcaa gtgcgggtcg     300
caggctggcg gcaagctgtg cccgaacaac ctctgctgca gccagtgggg cttctgcggt     360
ctgggcagcg agttttgcgg tggtggttgc agagcggcg cctgcagcac ggacaagccg     420
tgcggcaagg acgctggcgg ccgggtctgc actaacaact attgctgctc caagtggggc     480
tcctgcggca tcgcccgggg ctattgcggt gcgggctgcc agtcgggcgg ctgcgacggc     540
ggcactggca ccggtgtcga cgattataag gacgatgacg acaagagcgg cgagaacctg     600
tactttcagg gccacaacca tcggcacaag acggtacag cgccgctgc tatctctcaa     660 attggtgacg gtcaaatcca agccactacc aaaaccactg ctgctgctgt ttctcaaatt     720
ggtgacggtc aaatccaagc cactactaaa accaaagctg ctgctgtctc tcaaattggt     780
gacggccaaa tccaagccac caccaagact acctcagcta agactaccgc tgcagccgtc     840
tcccaaattg gtgacggtca aattcaagcc actactaaaa ccaaagctgc tgctgtctct     900
caaattggtg acggtcaaat ccaagccact accaaaacaa ctgctgcagc tgtctctcaa     960
attggtgacg gtcaaatcca agccactact aaaaccactg ctgctgctgt ttctcaaatt    1020
```

-continued

```
ggtgacggtc aaatccaagc caccaccaat actactgttg ctccagtctc ccaaatcact   1080
gatggccaaa tccaagccac aactttaact tcttga                             1116
```

<210> SEQ ID NO 7
<211> LENGTH: 1320
<212> TYPE: DNA
<213> ORGANISM: Artificial Sequence
<220> FEATURE:
<223> OTHER INFORMATION: Pir1b-L. culinaris lectin fusion

<400> SEQUENCE: 7

```
atgacatgtg aattccctag gctcgagact gagactacgt cgtttagcat taccaagttt     60
tcccctgatc agcagaacct gatcttccag ggcgacggct acaccacgaa gggcaagctg    120
accctgacga aggccgtcaa gagcactgtg ggccgggcgc tgtatagcac ccccattcac    180
atttgggacc gcgacaccgg gaacgtggcc aacttcgtga cctccttcac cttcgtgatc    240
gacgccccca gctcgtacaa cgtggcggac ggcttcacct tcttcatcgc gcctgtggac    300
acgaagccgc agacgggcgg cgggtatctg ggcgtcttca actcgaagga gtacgacaag    360
acttcgcaga ccgtggccgt ggagttcgat actttctaca acgcggcctg ggaccccagc    420
aacaaggagc gccacattgg catcgacgtg aactcgatca agtcggtgtc caccaagagc    480
tggaacctgc agaacggcga gcgcgcgaac gtggtcatcg cgttcaacgc cgccacgaac    540
gtcctgaccg tcaccctgac ctaccctaac tccctggagg aggagaacgt gacttcctac    600
acgctgaacg aggtggtgcc gctgaaggac gtggtgcccg agtgggtgcg gatcggcttc    660
agcgccacca cgggcgctga gttcgccgcc cacgaggtgc actcctggtc ctttcacagc    720
gagctgggtg gcaccagcag ctccggcacg ggcaccggtg tcgacgatta taaggacgat    780
gacgacaaga gcggcgagaa cctgtacttt cagggccaca accatcggca caagcacggt    840
acaggcgccg ctgctatctc tcaaattggt gacggtcaaa tccaagccac taccaaaacc    900
actgctgctg ctgtttctca aattggtgac ggtcaaatcc aagccactac taaaaccaaa    960
gctgctgctg tctctcaaat tggtgacggc caaatccaag ccaccaccaa gactacctca   1020
gctaagacta ccgctgcagc cgtctcccaa attggtgacg gtcaaattca agccactact   1080
aaaaccaaag ctgctgctgt ctctcaaatt ggtgacggtc aaatccaagc cactaccaaa   1140
acaactgctg cagctgtctc tcaaattggt gacggtcaaa tccaagccac tactaaaacc   1200
actgctgctg ctgtttctca aattggtgac ggtcaaatcc aagccaccac caatactact   1260
gttgctccag tctcccaaat cactgatggc caaatccaag ccacaacttt aacttcttga   1320
```

<210> SEQ ID NO 8
<211> LENGTH: 1479
<212> TYPE: DNA
<213> ORGANISM: Artificial Sequence
<220> FEATURE:
<223> OTHER INFORMATION: Pir1a-T. vulgaris lectin fusion

<400> SEQUENCE: 8

```
atgacatgtg aattccctag gctcgagcaa cggtgcgggg agcaggggtc caacatggag     60
tgccccaaca acctgtgctg ctcgcagtac gggtactgcg gcatgggcgg cgactactgc    120
ggcaagggct gccagaacgg cgcctgctgg acctccaagc gctgcggttc ccaggccggt    180
ggcgccacct gcaccaacaa ccagtgctgc tcccagtatg gctactgcgg cttcggcgcg    240
gagtactgcg gtgcgggctg ccagggcggc ccctgccgcg ctgacatcaa gtgcgggtcg    300
caggctggcg gcaagctgtg cccgaacaac ctctgctgca gccagtgggg cttctgcggt    360
```

```
ctgggcagcg agttttgcgg tggtggttgc cagagcggcg cctgcagcac ggacaagccg    420
tgcggcaagg acgctggcgg ccgggtctgc actaacaact attgctgctc caagtggggc    480
tcctgcggca tcggcccggg ctattgcggt gcgggctgcc agtcgggcgg ctgcgacggc    540
ggcactggca ccggtgtcga cgattacaag gatgatgatg acaagagcgg cgagaacctg    600
tacttccagg gccacaacca ccgccataag cacggtacag gcgccgctgc tatctctcaa    660
attggtgacg gtcaaatcca agccactacc aaaaccactg ctgctgctgt ttctcaaatt    720
ggtgacggtc aaatccaagc cactactaaa accaaagctg ctgctgtctc tcaaattggt    780
gacggccaaa tccaagccac caccaagact acctcagcta agactaccgc tgcagccgtc    840
tcccaaattg gtgacggtca aattcaagcc actactaaaa ccaaagctgc tgctgtctct    900
caaattggtg acggtcaaat ccaagccact accaaaacaa ctgctgcagc tgtctctcaa    960
attggtgacg gtcaaatcca agccactact aaaaccactg ctgctgctgt ttctcaaatt   1020
ggtgacggtc aaatccaagc caccaccaat actactgttg ctccagtctc ccaaatcact   1080
gatggccaaa tccaagccac aactttaact tctgcaacca ttataccatc tccagctcca   1140
gctccaatta ctaatggcac tgacccagta actgctgaaa catgcaaaag cagtggcact   1200
ttagaaatga acttaaaggg tggtatcctg actgacggta aaggtagaat tggttctatc   1260
gttgccaaca gacaattcca attcgatggt cctccaccac aagctggtgc tatctatgct   1320
gctggttggt ccatcacccc agaaggtaac ttggccatcg gtgaccagga tactttttac   1380
caatgtttgt caggaaactt ctacaactta tacgatgagc acattggaac tcaatgtaat   1440
gcagtccacc tacaagctat cgatttgctc aactgttag                          1479
```

<210> SEQ ID NO 9
<211> LENGTH: 4817
<212> TYPE: DNA
<213> ORGANISM: Artificial Sequence
<220> FEATURE:
<223> OTHER INFORMATION: L. culinaris lectin-Fas1 fusion

<400> SEQUENCE: 9

```
atggccaagc tgaccagcgc cgttccggtg ctcaccgcgc gcgacgtcgc cggagcggtc     60
gagttctgga ccgaccggct cgggttctcc cgggacttcg tggaggacga cttcgccggt    120
gtggtccggg acgacgtgac cctgttcatc agcgcggtcc aggaccaggt gagtcgacga    180
gcaagcccgg cggatcaggc agcgtgcttg cagatttgac ttgcaacgcc cgcattgtgt    240
cgacgaaggc ttttggctcc tctgtcgctg tctcaagcag catctaaccc tgcgtcgccg    300
tttccatttg caggaccagg tggtgccgga caacaccctg gcctgggtgt gggtgcgcgg    360
cctggacgag ctgtacgccg agtggtcgga ggtcgtgtcc acgaacttcc gggacgcctc    420
cgggccggcc atgaccgaga tcggcgagca gccgtggggg cgggagttcg ccctgcgcga    480
cccggccggc aactgcgtgc acttcgtggc cgaggagcag gacgccccgg tgaagcagac    540
cctgaacttc gacctgctga agctggcggg cgacgtggag agcaacccgg gcccccctcga    600 catggcgtct catgccgcgg cccagagcgc tttcacagct gtggccactg cagcggaccc    660
gggcctcgac gactacaagg acgacgacga caagtccggc ctcgagactg agactacgtc    720
gtttagcatt accaagtttt cccctgatca gcagaacctg atcttccagg gcgacggcta    780
caccacgaag ggcaagctga ccctgacgaa ggccgtcaag agcactgtgg gccgggcgct    840
gtatagcacc cccattcaca tttgggaccg cgacaccggg aacgtggcca acttcgtgac    900
```

| | |
|---|---|
| ctccttcacc ttcgtgatcg acgccccag ctcgtacaac gtggcggacg gcttcacctt | 960 |
| cttcatcgcg cctgtggaca cgaagccgca gacgggcggc gggtatctgg gcgtcttcaa | 1020 |
| ctcgaaggag tacgacaaga cttcgcagac cgtggccgtg gagttcgata ctttctacaa | 1080 |
| cgcggcctgg gacccagca acaaggagcc ccacattggc atcgacgtga actcgatcaa | 1140 |
| gtcggtgtcc accaagagct ggaacctgca gaacggcgag cgcgcgaacg tggtcatcgc | 1200 |
| gttcaacgcc gccacgaacg tcctgaccgt caccctgacc tacccctaact ccctggagga | 1260 |
| ggagaacgtg acttcctaca cgctgaacga ggtggtgccg ctgaaggacg tggtgcccga | 1320 |
| gtgggtgcgg atcggcttca cgccaccac gggcgctgag ttcgccgccc acgaggtgca | 1380 |
| ctcctggtcc ttttcacagcg agctgggtgg caccagcagc tccggcacgg gcaccggtga | 1440 |
| ctataaggac gacgacgaca agtccggtga gaacctgtac tttcagggcc acaaccaccg | 1500 |
| ccacaagcac accggtgtcg acctgttcct ttttacctca gccctccaac tgagcggcct | 1560 |
| tgtaacgttc ttcaacgcta ccggaaggaa catcacgtta ttcgcgccca gtgatcaggt | 1620 |
| tggtgcttgt acgtagctgg agggcttctg attatcaact cccctcgaac cctccactga | 1680 |
| ccccaaccta cgacctcaca cccatacgcg gcccaccgaa ggcgctacta gcggcgctgc | 1740 |
| cggccctgaa cctgaatcag tcccagctgg tgactaacgc agtgctcatg gcgccagtgc | 1800 |
| tcatgtacca cgctttcgtg ccagcgacca acaacgcctc tgtccctccc ggaatttcgt | 1860 |
| actacaacgc gttgaagtga ggcggggcg cgagtttaga aggttgacct ggatgcggcc | 1920 |
| acacggctcg cattgcagcc ttttcatgtt tgtgagtacc tcaatgttag gccaaaaacc | 1980 |
| gcgccaacgt gccaacctac agcacggatg gcagcgtcag cggcaaccag ctggcgatta | 2040 |
| cgaggacggt gtcgggcggt ctgcgggtca cctccatcgg cagcgacgcc aacgtgatca | 2100 |
| aggtggacct tcccaactcc gggtgagaga gcgcgtggct ggcggcgcca atgcgctggc | 2160 |
| tcctttcgcc tatgtcagga tgagtgtcgt ttcgttgcgg actggatcgg gtcgcggtgc | 2220 |
| atggggaagc ggcacccgt agaacgtgta tgggcaagtg gatgggtacc cgaacagtct | 2280 |
| gcctccgcgc gtcacacctc aactatctcc tctagacatg tggcattgta ttgtcgctga | 2340 |
| caacaggtcc acggtagtgc acgtcgtgga cgcggtgctt ctcccgttct acccgtcagt | 2400 |
| gtactccgtg agttgcagtg caagtgcggg cgcaggcgca agctgcagaa accaaaccgg | 2460 |
| gcaaggcgca tgctcggctc ctgcagccaa ccatatggcg cagacctgcc tttcgcagcg | 2520 |
| ccgacctaca tgaggcagcg acccaacacg ttgcccaacc cctgcgcctg cacgtgcgcc | 2580 |
| atgcaggctg tggcgcgcac ctctgccctg agcacgctgg ccgcgctggt cggctctgcc | 2640 |
| agcgccagcc tggtgtccaa gctgcaggtg cgtgtgtgtg ttgagcgggt ggtgaagatt | 2700 |
| tggtgggcgg gctgggcacg ccgccgttct tgggttacgg caagtgccgt gttttgctga | 2760 |
| ctggcggcgg agttgtgcgc gtgctcgcgc tctctggcg catcacagcg ccctgatgg | 2820 |
| tgtgcactga agtggcgatt gcgttccgtc ctgggcatgt tctacaggac actacgggtg | 2880 |
| tctacaccgt ctttgctccc tacaatgcgt gagttgtggt tcagcaccca ctggttgtgc | 2940 |
| caggccgaca ggccgacgtt gcgtcaagtc gcgaaccgtg cgcggctgca agcattgccc | 3000 |
| tgaccggctt tggattgccc agcggctcct acgctgacct tccctcgctg tggctccctc | 3060 |
| cctcgtgtgc acagcgcctt cacggccgcc ctggcccccc ccggcctcaa cacgacgatt | 3120 |
| gcgcagctgg cggcgcagcc cgccctgctg cagtccatcc tgtcgtacca cgtcgtgccc | 3180 |
| ggcctgtaca cgcctcctc gttttccacc acacccatca ccgtcaccac cctgacgtat | 3240 |
| ggcttcgctg catgcatgcg cacccagcgt gtgtgcgcca ccgtgcagag gcaggcctca | 3300 |

```
accttcagat cagtctgatc agtttgacca gttgcattcc gacacacgac gatgccctgg    3360
catgcctcaa tgccccgctc cgcagtggcc agaagctgac gctggtgaag acggcactt    3420 cgctgtcggt gaagacggcc gacggcatga cggccaacct gctgcaggcg cgcgacctgc    3480
cgtgcggctt cacggaccag tgagttggtc gcgcgagtga ccagcatagc acgggacaag    3540
gactcgtggc atcccgttgt tcaggatggg tttgcaccgg cgtaggagcc ccaaatccca    3600
acatgcacag ctaacgcatt tcacactaca cgtccaacct gtcaggggca cgttccgcgc    3660
gaccgtgcac gtgatcgaca aggtactcgt ccctcccccct gttacctccg tggctgcggc    3720
gctggccctg cgcaccgacg tcaacacact gctggcggcc gtcaaggcgg agggtccta    3780 ctcggctgcg atcaacaggt gacttgcggc aaccggcgcc gttacaaacg ctatgcgctt    3840
actgccgctt ctcgggcaca tactgcgtcc atttgactgc attacgaagg actggactta    3900
ccccagaatt gttcccctgc ctgtgctgca tgccctgaaa ccctcagcac acattcacc    3960 ggcacgcttc tggcgcccat cgactcggcc ttcacggcgc tgctggcggc caatggcagc    4020
atcagcgccg cgcagctgct gggcaacacc acggcgctga agaagatcct ggacgtgagt    4080
gctcgtgcta tgcaggcgtc ctcaggccac agacctctat gtacagccag cgtgcctgac    4140
cttgtggtgc ttctggctgt gttcaggcgc acgtggtcac ggggtcggtg ctgacggtgg    4200
cgggtctcac caacggccag aacattacca ccaggtgggg gcattagcca ttgggcttga    4260
ggtgtccccc acattgggtg gttgccgctg cggcttttgg tcattatgct gagtagaatg    4320
ctatgctctt ggcttgatct ttgcgttgca tcatgtatcc tgttcgcagt ggcggcgcta    4380
cgatcacggt tgtcaagacc ggaaccacga cccagctgaa gctgggcaac agcgtggtca    4440
gcgtggtcgg ggcggaggtt gcgattggca gcaggtgggt gcacctgacc tcttcattgc    4500
caccttcctg cagcgctgat gatggcttct ttgcgacgtt atcgacgtgc ttaaaaacgc    4560
aacacaacaa gtgccatcgc cgcgagcctg catgctgtgt tatggtgtca acgcgcccca    4620 tacccatgc catgccccct ggtgtttgca gcgcgacgct catcgtcatc gacggtgtcc    4680
tggtgccgtc cggcgtttcc accgtgacct cgggaggcgg tggcggcgcc gcagcggcaa    4740
ctacgccgtc cttcgtgctc atgctgtgga gcgttgtggc ggcagcgctg ctgctagcat    4800
tccagcgcct gcagtag                                                  4817
```

<210> SEQ ID NO 10
<211> LENGTH: 4256
<212> TYPE: DNA
<213> ORGANISM: Artificial Sequence
<220> FEATURE:
<223> OTHER INFORMATION: L. culinaris truncated lectin-Fas1 fusion

<400> SEQUENCE: 10

```
atggccaagc tgaccagcgc cgttccggtg ctcaccgcgc gcgacgtcgc cggagcggtc     60
gagttctgga ccgaccggct cgggttctcc cgggacttcg tggaggacga cttcgccggt    120
gtggtccggg acgacgtgac cctgttcatc agcgcggtcc aggaccaggt gagtcgacga    180
gcaagcccgg cggatcaggc agcgtgcttg cagatttgac ttgcaacgcc cgcattgtgt    240
cgacgaaggc ttttggctcc tctgtcgctg tctcaagcag catctaaccc tgcgtcgccg    300
tttccatttg caggaccagg tggtgccgga caacaccctg gcctgggtgt gggtgcgcgg    360
cctggacgag ctgtacgccg agtggtcgga ggtcgtgtcc acgaacttcc gggacgcctc    420
cgggccggcc atgaccgaga tcggcgagca gccgtggggg cgggagttcg ccctgcgcga    480
```

```
cccggccggc aactgcgtgc acttcgtggc cgaggagcag gacgcccgg tgaagcagac    540 cctgaacttc gacctgctga agctggcggg cgacgtggag agcaacccgg ccccctcga    600 catggcgtct catgccgcgg cccagagcgc tttcacagct gtggccactg cagcggaccc    660
gggcctcgac gactacaagg acgacgacga caagtccggc ctcgaggtga cttcctacac    720
gctgaacgag gtggtgccgc tgaaggacgt ggtgcccgag tgggtgcgga tcggcttcag    780
cgccaccacg ggcgctgagt cgccgcccca cgaggtgcac tcctggtcct ttcacagcga    840
gctgggtggc accagcagct ccggcacggg caccggtgac tataaggacg acgacgacaa    900
gtccggtgag aacctgtact ttcagggcca aaccaccgc cacaagcaca ccggtgtcga    960
cctgttcctt tttacctcag ccctccaact gagcggcctt gtaacgttct tcaacgctac   1020
cggaaggaac atcacgttat cgcgcccag tgatcaggtt ggtgcttgta cgtagctgga    1080
gggcttctga ttatcaactc ccctcgaacc ctccactgac cccaacctac gacctcacac   1140
ccatacgcgg cccaccgaag cgctactag cggcgctgcc ggccctgaac ctgaatcagt     1200
cccagctggt gactaacgca gtgctcatgg cgccagtgct catgtaccac gctttcgtgc    1260
cagcgaccaa caacgcctct gtccctcccg gaatttcgta ctacaacgcg ttgaagtgag    1320 gcggggcgc gagtttagaa ggttgacctg gatgcggcca cacggctcgc attgcagcct    1380
tttcatgttt gtgagtacct caatgttagg ccaaaaaccg cgccaacgtg ccaacctaca    1440
gcacggatgg cagcgtcagc ggcaaccagc tggcgattac gaggacggtg tcgggcggtc    1500
tgcgggtcac ctccatcggc agcgacgcca acgtgatcaa ggtggacctt cccaactccg    1560
ggtgagagag cgcgtggctg gcggcgccaa tgcgctggct cctttcgcct atgtcaggat    1620
gagtgtcgtt tcgttgcgga ctggatcggg tcgcggtgca tggggaagcg gcacccggta    1680
gaacgtgtat gggcaagtgg atgggtaccc gaacagtctg cctccgcgcg tcacacctca    1740
actatctcct ctagacatgt ggcattgtat tgtcgctgac aacaggtcca cggtagtgca    1800
cgtcgtggac gcggtgcttc tcccgttcta cccgtcagtg tactccgtga gttgcagtgc    1860
aagtgcgggc gcaggcgcaa gctgcagaaa ccaaaccggg caaggcgcat gctcggctcc    1920
tgcagccaac catatggcgc agacctgcct ttcgcagcgc cgacctacat gaggcagcga    1980
cccaacacgt gcccaaccc ctgcgcctgc acgtgcgcca tgcaggctgt ggcgcgcacc     2040
tctgccctga gcacgctggc cgcgctggtc ggctctgcca cgccagcct ggtgtccaag     2100 ctgcaggtgc gtgtgtgtgt tgagcgggtg gtgaagattt ggtgggcggg ctgggcacgc    2160
cgccgttctt gggttacggc aagtgccgtg ttttgctgac tggcggcgga gttgtgcgcg    2220
tgctcgcgcc tctctggcgc atcacagcgc ccctgatggt gtgcactgaa gtggcgattg    2280
cgttccgtcc tgggcatgtt ctacaggaca ctacgggtgt ctacaccgtc tttgctcccct   2340 acaatgcgtg agttgtggtt cagcacccac tggttgtgcc aggccgacag gccgacgttg    2400
cgtcaagtcg cgaaccgtgc gcggctgcaa gcattgccct gaccggcttt ggattgccca    2460
gcggctccta cgctgacctt ccctcgctgt ggctccctcc ctcgtgtgca cagcgccttc    2520
acggccgccc tggcccccctc cggcctcaac acgacgattg cgcagctggc ggcgcagccc   2580
gccctgctgc agtccatcct gtcgtaccac gtcgtgcccg gctgtacaa cgcctcctcg     2640 ttttccacca cacccatcac cgtcaccacc ctgacgtatg gcttcgctgc atgcatgcgc    2700
acccagcgtg tgtgcgccac cgtgcagagg caggcctcaa ccttcagatc agtctgatca    2760
gtttgaccag ttgcattccg acacacgacg atgccctggc atgcctcaat gccccgctcc    2820
gcagtggcca gaagctgacg ctggtgaagg acggcacttc gctgtcggtg aagacggccg    2880
```

```
acggcatgac ggccaacctg ctgcaggcgc gcgacctgcc gtgcggcttc acggaccagt   2940
gagttggtcg cgcgagtgac cagcatagca cgggacaagg actcgtggca tcccgttgtt   3000
caggatgggt ttgcaccggc gtaggagccc caaatcccaa catgcacagc taacgcattt   3060
cacactacac gtccaacctg tcaggggcac gttccgcgcg accgtgcacg tgatcgacaa   3120
ggtactcgtc cctcccctg ttacctccgt ggctgcggcg ctggccctgc gcaccgacgt    3180
caacacactg ctggcggccg tcaaggcgga ggggtcctac tcggctgcga tcaacaggtg   3240
acttgcggca accggcgccg ttacaaacgc tatgcgctta ctgccgcttc cgggcacat    3300 actgcgtcca tttgactgca ttacgaagga ctggacttac cccagaattg ttcccctgcc   3360
tgtgctgcat gccctgaaac cctcagcacc acattcaccg gcacgcttct ggcgcccatc   3420
gactcggcct tcacggcgct gctggcggcc aatggcagca tcagcgccgc gcagctgctg   3480
ggcaacacca cggcgctgaa gaagatcctg gacgtgagtg ctcgtgctat gcaggcgtcc   3540
tcaggccaca gacctctatg tacagccagc gtgcctgacc ttgtggtgct tctggctgtg   3600
ttcaggcgca cgtggtcacg gggtcggtgc tgacggtggc gggtctcacc aacggccaga   3660
acattaccac caggtggggg cattagccat tgggcttgag gtgtccccca cattgggtgg   3720
ttgccgctgc ggcttttggt cattatgctg agtagaatgc tatgctcttg gcttgatctt   3780
tgcgttgcat catgtatcct gttcgcagtg cggcgctac gatcacggtt gtcaagaccg    3840
gaaccacgac ccagctgaag ctgggcaaca gcgtggtcag cgtggtcggg gcggaggttg   3900
cgattggcag caggtgggtg cacctgacct cttcattgcc accttcctgc agcgctgatg   3960
atggcttctt tgcgacgtta tcgacgtgct taaaaacgca acacaacaag tgccatcgcc   4020
gcgagcctgc atgctgtgtt atggtgtcaa cgcgccccat accccatgcc atgccccctg   4080
gtgtttgcag cgcgacgctc atcgtcatcg acggtgtcct ggtgccgtcc ggcgtttcca   4140
ccgtgacctc ggggaggcggt ggcggcgccg cagcggcaac tacgccgtcc ttcgtgctca   4200
tgctgtggag cgttgtggcg gcagcgctgc tgctagcatt ccagcgcctg cagtag        4256
```

<210> SEQ ID NO 11
<211> LENGTH: 4817
<212> TYPE: DNA
<213> ORGANISM: Artificial Sequence
<220> FEATURE:
<223> OTHER INFORMATION: E. cristagalli lectin-Fas1 fusion

<400> SEQUENCE: 11

```
atggccaagc tgaccagcgc cgttccggtg ctcaccgcgc gcgacgtcgc cggagcggtc     60
gagttctgga ccgaccggct cgggttctcc cgggacttcg tggaggacga cttcgccggt    120
gtggtccggg acgacgtgac cctgttcatc agcgcggtcc aggaccaggt gagtcgacga    180
gcaagcccgg cggatcaggc agcgtgcttg cagatttgac ttgcaacgcc cgcattgtgt    240
cgacgaaggc ttttggctcc tctgtcgctg tctcaagcag catctaaccc tgcgtcgccg    300
tttccatttg caggaccagg tggtgccgga caacaccctg cctgggtgt gggtgcgcgg     360 cctggacgag ctgtacgccg agtggtcgga ggtcgtgtcc acgaacttcc gggacgcctc    420
cgggccggcc atgaccgaga tcggcgagca gccgtggggg cggagttcg ccctgcgcga     480 cccggccggc aactgcgtgc acttcgtggc cgaggagcag gacgccccgg tgaagcagac    540
cctgaacttc gacctgctga agctggcggg cgacgtggag agcaacccgg ccccctcga    600 catggcgtct catgccgcgg cccagagcgc tttcacagct gtggccactg cagcggaccc    660
```

```
gggcctcgac gactacaagg acgacgacga caagtccggc ctcgaggtgg agactattag    720
cttttccttt tcggagtttg agcctggtaa cgataacctg accctgcagg gtgctgccct    780
cattacccag agcggcgtgc tgcagctcac taagatcaac cagaacggta tgccggcttg    840
ggactcgacg ggccggaccc tgtacacgaa gcccgtgcac atgtgggaca gcaccacggg    900
gaccgtggct tccttcgaga ctcgcttttc gttctccatc gagcagccct acacccgccc    960
tctcccggcc gacggcctgg tgttctttat gggccccacc aagagcaagc cggcccaggg   1020
ctacggttac ctgggcgtgt tcaacaactc caagcaggac aacagctacc agaccctggc   1080
ggtcgagttt gacaccttct cgaaccctg ggacccgcct caggtgcccc acatcgggat   1140
cgacgtgaac tcgattcgct cgatcaagac ccagccgttt cagctggaca acggccaagt   1200
ggcgaacgtg gtgattaagt acgacgcccc cagcaagatc ctgcatgtgg tcctggtgta   1260
cccgagctcc ggcgccatct acacgatcgc cgagattgtg gacgtgaagc aggtgctgcc   1320
ggactgggtg gatgtgggtc tgtcgggcgc cactggcgcg cagcgggatg cggcggagac   1380
gcacgacgtg tactcgtggt ccttccaggc ttccctgccg gaggggaccg gcaccggtga   1440
ctacaaggac gacgatgaca gtcgggcga gaacctgtac tttcagggcc acaaccaccg   1500
ccacaagcac accggtgtcg acctgttcct ttttacctca gccctccaac tgagcggcct   1560
tgtaacgttc ttcaacgcta ccggaaggaa catcacgtta ttcgcgccca gtgatcaggt   1620
tggtgcttgt acgtagctgg agggcttctg attatcaact cccctcgaac cctccactga   1680
ccccaaccta cgacctcaca cccatacgcg gcccaccgaa ggcgctacta gcggcgctgc   1740
cggccctgaa cctgaatcag tcccagctgg tgactaacgc agtgctcatg cgccagtgc   1800 tcatgtacca cgctttcgtg ccagcgacca acaacgcctc tgtccctccc ggaatttcgt   1860
actacaacgc gttgaagtga ggcggggggcg cgagtttaga aggttgacct ggatgcggcc   1920
acacggctcg cattgcagcc ttttcatgtt tgtgagtacc tcaatgttag gccaaaaacc   1980
gcgcaaacgt gccaacctac agcacggatg gcagcgtcag cggcaaccag ctggcgatta   2040
cgaggacggt gtcgggcggt ctgcgggtca cctccatcgg cagcgacgcc aacgtgatca   2100
aggtggacct tcccaactcc gggtgagaga gcgcgtggct ggcggcgcca atgcgctggc   2160
tcctttcgcc tatgtcagga tgagtgtcgt ttcgttgcgg actggatcgg gtcgcggtgc   2220
atggggaagc ggcacccggt agaacgtgta tgggcaagtg gatgggtacc cgaacagtct   2280
gcctccgcgc gtcacacctc aactatctcc tctagacatg tggcattgta ttgtcgctga   2340
caacaggtcc acggtagtgc acgtcgtgga cgcggtgctt ctcccgttct acccgtcagt   2400
gtactccgtg agttgcagtg caagtgcggg cgcaggcgca agctgcagaa accaaaccgg   2460
gcaaggcgca tgctcggctc ctgcagccaa ccatatggcg cagacctgcc tttcgcagcg   2520
ccgacctaca tgaggcagcg acccaacacg ttgcccaacc cctgcgcctg cacgtgcgcc   2580
atgcaggctg tggcgcgcac ctctgccctg agcacgctgg ccgcgctggt cggctctgcc   2640
agcgccagcc tggtgtccaa gctgcaggtg cgtgtgtgtg ttgagcgggt ggtgaagatt   2700
tggtgggcgg gctgggcacg ccgccgttct tgggttacgg caagtgccgt gttttgctga   2760 ctggcggcg agttgtgcgc gtgctcgcgc ctctctggcg catcacagcg cccctgatgg   2820
tgtgcactga agtggcgatt cgttccgtc ctgggcatgt tctacaggac actacgggtg   2880
tctacaccgt ctttgctccc tacaatgcgt gagttgtggt tcagcaccca ctggttgtgc   2940
caggccgaca ggccgacgtt gcgtcaagtc gcgaaccgtg cgcggctgca agcattgccc   3000
tgaccggctt tggattgccc agcggctcct acgctgacct tccctcgctg tggctccctc   3060
```
cctcgtgtgc acagcgcctt cacggccgcc ctggccccct ccggcctcaa cacgacgatt    3120
gcgcagctgg cggcgcagcc cgccctgctg cagtccatcc tgtcgtacca cgtcgtgccc    3180
ggcctgtaca acgcctcctc gttttccacc acacccatca ccgtcaccac cctgacgtat    3240
ggcttcgctg catgcatgcg cacccagcgt gtgtgcgcca ccgtgcagag gcaggcctca    3300
accttcagat cagtctgatc agtttgacca gttgcattcc gacacacgac gatgccctgg    3360
catgcctcaa tgccccgctc cgcagtggcc agaagctgac gctggtgaag acggcacttt    3420
cgctgtcggt gaagacggcc gacggcatga cggccaacct gctgcaggcg cgcgacctgc    3480
cgtgcggctt cacggaccag tgagttggtc gcgcgagtga ccagcatagc acgggacaag    3540
gactcgtggc atcccgttgt tcaggatggg tttgcaccgg cgtaggagcc ccaaatccca    3600
acatgcacag ctaacgcatt tcacactaca cgtccaacct gtcaggggca cgttccgcgc    3660
gaccgtgcac gtgatcgaca aggtactcgt ccctccccct gttacctccg tggctgcggc    3720
gctggccctg cgcaccgacg tcaacacact gctggcggcc gtcaaggcgg aggggtccta    3780
ctcggctgcg atcaacaggt gacttgcggc aaccggcgcc gttacaaacg ctatgcgctt    3840
actgccgctt ctcgggcaca tactgcgtcc atttgactgc attacgaagg actggactta    3900
ccccagaatt gttcccctgc ctgtgctgca tgccctgaaa ccctcagcac acattcacc    3960 ggcacgcttc tggcgcccat cgactcggcc ttcacggcgc tgctggcggc caatggcagc    4020
atcagcgccg cgcagctgct gggcaacacc acggcgctga agaagatcct ggacgtgagt    4080
gctcgtgcta tgcaggcgtc ctcaggccac agacctctat gtacagccag cgtgcctgac    4140
cttgtggtgc ttctggctgt gttcaggcgc acgtggtcac ggggtcggtg ctgacggtgg    4200
cgggtctcac caacggccag aacattacca ccaggtgggg gcattagcca ttgggcttga    4260
ggtgtccccc acattgggtg gttgccgctg cggcttttgg tcattatgct gagtagaatg    4320
ctatgctctt ggcttgatct ttgcgttgca tcatgtatcc tgttcgcagt ggcggcgcta    4380
cgatcacggt tgtcaagacc ggaaccacga cccagctgaa gctgggcaac agcgtggtca    4440
gcgtggtcgg ggcggaggtt gcgattgcag caggtgggt gcacctgacc tcttcattgc    4500
caccttcctg cagcgctgat gatggcttct ttgcgacgtt atcgacgtgc ttaaaaacgc    4560
aacacaacaa gtgccatcgc cgcgagcctg catgctgtgt tatggtgtca acgcgcccca    4620 tacccccatgc catgccccct ggtgtttgca gcgcgacgct catcgtcatc gacggtgtcc    4680
tggtgccgtc cggcgtttcc accgtgacct cgggaggcgg tggcggcgcc gcagcggcaa    4740
ctacgccgtc cttcgtgctc atgctgtgga gcgttgtggc ggcagcgctg ctgctagcat    4800
tccagcgcct gcagtag                                                   4817

<210> SEQ ID NO 12
<211> LENGTH: 3121
<212> TYPE: DNA
<213> ORGANISM: Artificial Sequence
<220> FEATURE:
<223> OTHER INFORMATION: H. pomatia lectin-GP1

<400> SEQUENCE: 12
atggccaagc tgaccagcgc cgttccggtg ctcaccgcgc gcgacgtcgc cggagcggtc      60
gagttctgga ccgaccggct cgggttctcc cgggacttcg tggaggacga cttcgccggt     120
gtggtccggg acgacgtgac cctgttcatc agcgcggtcc aggaccaggt gagtcgacga     180
gcaagcccgg cggatcaggc agcgtgcttg cagatttgac ttgcaacgcc cgcattgtgt     240

```
cgacgaaggc ttttggctcc tctgtcgctg tctcaagcag catctaaccc tgcgtcgccg      300
tttccatttg caggaccagg tggtgccgga caacaccctg gcctgggtgt gggtgcgcgg      360
cctggacgag ctgtacgccg agtggtcgga ggtcgtgtcc acgaacttcc gggacgcctc      420
cgggccggcc atgaccgaga tcggcgagca gccgtggggg cgggagttcg ccctgcgcga      480
cccggccggc aactgcgtgc acttcgtggc cgaggagcag gacgccccgg tgaagcagac      540
cctgaacttc gacctgctga agctggcggg cgacgtggag agcaacccgg gccccctcga      600
catgatgcgg cggcaacacg ctgccccccT tgtggggcg gtcaacgtct tgatggtggt      660
gctcgccttc gtcgcgagcg ctaacgcgca gtgtgtacct ggcggtatct tcaactgcct      720
cgagcagtgc gccctgaaga ccattgcttt cagcgccgcc atcgaccgcg agcagacgtt      780
tgacgccaac caggtggtca tctacgacat cgtgattacg aaccacggca acgcctacga      840
taactccacc ggcctgttca ccgcgccggt ggacggcatg tacagctttc aactgaacct      900
gctcacgatt aaggagaagg agggctggct ggagctcgtg cacaacggtc agctcaaggt      960
gagcgtctac gcgaagcagg acagcacgta cgattcgtcg agcaactcgg tcatcatcaa     1020
gatgaaggag ggtgatcggg tgaacgtgcg ggcccacaag aagtcgggtc tgttcggccg     1080
cgacgacgag ctgtacaaca cgttctccgg ccacttcctg tccggcctgg gcaccggcac     1140
cggtgactac aaggacgacg acgacaagtc cggcgagaac ctgtacttcc agggccacaa     1200
ccaccgccac aagcacaccg tgtcgaccct ccctctccgg ccccaccgt ctcctgcccc     1260 tccctccccg gctccccgt cacccgcacc cccttcgcca gcaccccga gcccagggcc      1320 cccctcgccc gccccgccga gcccgccgag ccctgcgccc cgagccctg cgccgccgag     1380 cccggccccc ccgtccccg ccccccgtc tcccgcgccg ccatcgcctg cgcctccttc      1440
ccctgcgcca ccgtcccccg ccccaccctc gccccgagc ccggcccctc cgtcgcccag     1500
cccgccggcc cccccctcgc cgtcgcccc gtcgccagcc caccccctgc caccctcccc     1560
agcgccgccc agcccctccc cccggtccc gccgtcaccg agcccgcccg tccctcccag     1620 cccgcccct ccttcgccca cgcctccgtc cccagccct ccgtgccgc cagcccgc       1680 cccgccctct cccgccccgc ccgtgccgcc ctcgccggca ccgccctccc ctgctccccc     1740
ggtgccgcct agccctgccc cccgtcgcc tccctcgcca gcgcccctt ccccccag        1800 ccccgccccc cctcgccgt ccccccgc tccccgagc ccgtgcccc cttctccggc         1860 gcccccagc cccgcgcccc cctccctaa gccgcccgcg ccaccccgc ctcccagccc       1920 accgcctccc ccgccgcccc gtccccatt ccccgccaac actccatgc ccatcccc      1980 tccctccccg cccccctccc cggcgccacc cacaccccc accccccctt caccgtcgcc     2040
gccgtcgccc gttccgccca gcccagcgcc tgtgccgccc agcccgccc cgccctccc      2100 agctcccagc ccccccccta gccccgctcc gccgacccg tccccaagcc cctcgccttc      2160
gccctccccg agccctcgc cctccccgag ccctcgccc tccccgagcc cagcccgat       2220 ccctctcccc tcgccgaagc ccagcccctc accgtggc gtcaagctgg tttgggctga      2280
tgatgccatc gccttcgacg acctgaacgg cacctcgacc aggcccggct ccgcctcgcg     2340
catggtcggc gagcccgaca tcgccggcac caagtgcaag gcaacctga agggctggat      2400 gcccaagccc agcagggtgg gtcctaggaa gactttgctg tttgctgcgc tgcctaggca     2460
tcatgacgcc tgtatgacgt tgtcttttga aggaagttcg aggattgcgc tgagttggga     2520
ccgcacgcaa gcaacttatc cacgccacgg tccctctcca tcttcctctt cgcagaaccc     2580
tcgctggggc caggctgtgt tctccggtgg ccgcaccgtg ggctccgtcg ctaacgtcac     2640
```

-continued

| | |
|---|---|
| catccgcgtc gcgtgagtcg gacttttgag ccgcctgtac tgtcgtccgg tgcttggcct | 2700 |
| cgttttgtcg gatgatctgc cgatatccaa ctggagcttg cttgactgac cgcttttctc | 2760 |
| atccgttggg cgcctcacct tgcctacccg cagtttcgcg accgagaagc ccgcgctgat | 2820 |
| ctactccagc atcgagctgg tcgtgtacaa cactggtgcc accctcatcc gcgtgccat | 2880 |
| cgccgccaat gtgacccgca gccagatcag gtgccctggc ttcctgacct atggcaccac | 2940 |
| ccccattgcc ggctacccca ctggcatcga cgccaccacc tggcccaact ggaagattgc | 3000 |
| cggcgtgcgc atcaacatgg gcgcgggcaa caagaagccc aagacctcga ttgacgcggt | 3060 |
| cggcctcaac ctgaagagcg gttccggcga ctacaaggac gacgacgaca gtccggcta | 3120 |
| a | 3121 |

<210> SEQ ID NO 13
<211> LENGTH: 2872
<212> TYPE: DNA
<213> ORGANISM: Artificial Sequence
<220> FEATURE:
<223> OTHER INFORMATION: L. culinaris truncated lectin-GP1

<400> SEQUENCE: 13

| | |
|---|---|
| atggccaagc tgaccagcgc cgttccggtg ctcaccgcgc gcgacgtcgc cggagcggtc | 60 |
| gagttctgga ccgaccggct cgggttctcc cgggacttcg tggaggacga cttcgccggt | 120 |
| gtggtccggg acgacgtgac cctgttcatc agcgcggtcc aggaccaggt gagtcgacga | 180 |
| gcaagcccgg cggatcaggc agcgtgcttg cagatttgac ttgcaacgcc cgcattgtgt | 240 |
| cgacgaaggc ttttggctcc tctgtcgctg tctcaagcag catctaaccc tgcgtcgccg | 300 |
| tttccatttg caggaccagg tggtgccgga caacaccctg gcctgggtgt gggtgcgcgg | 360 |
| cctggacgag ctgtacgccg agtggtcgga ggtcgtgtcc acgaacttcc gggacgcctc | 420 |
| cgggccggcc atgaccgaga tcggcgagca gccgtggggg cgggagttcg ccctgcgcga | 480 |
| cccggccggc aactgcgtgc acttcgtggc cgaggagcag gacgccccgg tgaagcagac | 540 |
| cctgaacttc gacctgctga agctggcggg cgacgtggag agcaacccgg ccccctcga | 600 |
| catgatgcgg cggcaacacg ctgcccccct tgtgggggcg gtcaacgtct tgatggtggt | 660 |
| gctcgccttc gtcgcgagcg ctaacgcgca gtgtgtacct ggcggtatct tcaactgcct | 720 |
| cgaggtgact tcctacacgc tgaacgaggt ggtgccgctg aaggacgtgg tgcccgagtg | 780 |
| ggtgcggatc ggcttcagcg ccaccacggg cgctgagttc gccgcccacg aggtgcactc | 840 |
| ctggtccttt cacagcgagc tgggtggcac cagcagctcc ggcacgggca ccggtgacta | 900 |
| taaggacgac gacgacaagt ccggtgagaa cctgtacttt cagggccaca accaccgcca | 960 |
| caagcacacc ggtgtcgacc ctccctctcc ggccccaccg tctcctgccc ctccctcccc | 1020 |
| ggctccccg tcaccgcac cccttcgcc agcacccccg agcccagggc ccccctcgcc | 1080 |
| cgccccgccg agcccgccga gccctgcgcc cccgagccct cgccgccga gccggcccc | 1140 |
| cccgtccccc gcccccccgt ctcccgcgcc gccatcgcct gcgcctcctt cccctgcgcc | 1200 |
| accgtccccc gccccaccct cgcccccgag cccggcccct ccgtcgccca gcccgccggc | 1260 |
| cccccctcg ccgtcgcccc cgtcgccagc cccaccccctg ccaccctccc cagccgccgc | 1320 |
| cagcccctcc cccccggtcc cgccgtcacc gagcccgccc gtccctccca gcccgccccc | 1380 |
| tccttcgccc acgcctccgt ccccagccc tccgtgccg ccagccccg cccgccctc | 1440 |
| tcccgccccg cccgtgccgc cctcgccggc accgccctcc cctgctcccc cggtgccgcc | 1500 |

| | |
|---|---|
| tagccctgcc ccccgtcgc ctccctcgcc agcgccccct tcccccccca gccccgcccc | 1560 |
| cccctcgccg tccccccccg ctccccgag cccgtgccc ccttctccgg cgccccccag | 1620 |
| ccccgcgccc ccctccccta agccgcccgc gccaccccg cctcccagcc caccgcctcc | 1680 |
| cccgccgccc cgtccccat tccccgccaa cactcccatg cccccatccc ctccctcccc | 1740 |
| gccccctcc ccggcgccac ccacacccc caccccct tcaccgtcgc cgccgtcgcc | 1800 |
| cgttccgccc agcccagcgc ctgtgccgcc cagccccgcc ccgccctccc cagctcccag | 1860 |
| ccccccccct agccccgctc cgccgacccc gtcccaagc ccctcgcctt cgccctcccc | 1920 |
| gagcccctcg ccctccccga gccctcgcc ctccccgagc ccagcccga tcccctctcc | 1980 |
| ctcgccgaag cccagcccct caccgtggc cgtcaagctg gtttgggctg atgatgccat | 2040 |
| cgccttcgac gacctgaacg gcacctcgac caggcccggc tccgcctcgc gcatggtcgg | 2100 |
| cgagcccgac atcgccggca ccaagtgcaa gggcaacctg aagggctgga tgcccaagcc | 2160 |
| cagcagggtg ggtcctagga agactttgct gtttgctgcg ctgcctaggc atcatgacgc | 2220 |
| ctgtatgacg ttgtctttg aaggaagttc gaggattgcg ctgagttggg accgcacgca | 2280 |
| agcaacttat ccacgccacg gtccctctcc atcttcctct tcgcagaacc ctcgctgggg | 2340 |
| ccaggctgtg ttctccggtg gccgcaccgt gggctccgtc gctaacgtca ccatccgcgt | 2400 |
| cgcgtgagtc ggacttttga gccgcctgta ctgtcgtccg gtgcttggcc tcgttttgtc | 2460 |
| ggatgatctg ccgatatcca actggagctt gcttgactga ccgcttttct catccgttgg | 2520 |
| gcgcctcacc ttgcctaccc gcagtttcgc gaccgagaag cccgcgctga tctactccag | 2580 |
| catcgagctg gtcgtgtaca acactggtgc caccctcatc cgcgtgccca tcgccgccaa | 2640 |
| tgtgacccgc agccagatca ggtgccctgg cttcctgacc tatggcacca cccccattgc | 2700 |
| cggctacccc actggcatcg acgccaccac ctggcccaac tggaagattg ccggcgtgcg | 2760 |
| catcaacatg ggcgcgggca caagaagcc caagacctcg attgacgcgg tcggcctcaa | 2820 |
| cctgaagagc ggttccggcg actacaagga cgacgacgac aagtccggct aa | 2872 |

<210> SEQ ID NO 14
<211> LENGTH: 4823
<212> TYPE: DNA
<213> ORGANISM: Artificial Sequence
<220> FEATURE:
<223> OTHER INFORMATION: scFv5-Fas1 fusion

<400> SEQUENCE: 14

| | |
|---|---|
| atggccaagc tgaccagcgc cgttccggtg ctcaccgcgc gcgacgtcgc cggagcggtc | 60 |
| gagttctgga ccgaccggct cgggttctcc cgggacttcg tggaggacga cttcgccggt | 120 |
| gtggtccggg acgacgtgac cctgttcatc agcgcggtcc aggaccaggt gagtcgacga | 180 |
| gcaagcccgg cggatcaggc agcgtgcttg cagatttgac ttgcaacgcc cgcattgtgt | 240 |
| cgacgaaggc ttttggctcc tctgtcgctg tctcaagcag catctaaccc tgcgtcgccg | 300 |
| tttccatttg caggaccagg tggtgccgga acacccctg gcctgggtgt gggtgcgcgg | 360 |
| cctggacgag ctgtacgccg agtggtcgga ggtcgtgtcc acgaacttcc gggacgcctc | 420 |
| cgggccggcc atgaccgaga tcggcgagca gccgtggggg cggagttcg ccctgcgcga | 480 |
| cccggccggc aactgcgtgc acttcgtggc cgaggagcag gacgccccgg tgaagcagac | 540 |
| cctgaacttc gacctgctga agctggcggg cgacgtggag agcaaccccgg gccccctcga | 600 |
| catggcgtct catgccgcgg cccagagcgc tttcacagct gtggcactg cagcggaccc | 660 |
| gggcctcgac gactacaagg acgacgacga caagtccggc ctcgagatga aatacctatt | 720 |

```
gcctacggca gccgctggat tgttattact cgcggcccag ccggccatgg ccgaggtgca    780
gctgttggag tctgggggag gcttggtaca gcctgggggg tccctgagac tctcctgtgc    840
agcctctgga ttcacctttta gcagctatgc catgagctgg gtccgccagg ctccagggaa    900
ggggctgag tgggtctcat ggatttcggg gactggttcg cggacagact acgcagactc    960
cgtgaagggc cggttcacca tctccagaga caattccaag aacacgctgt atctgcaaat   1020
gaacagcctg agagccgagg acacggccgt atattactgt gcgaaaaagg cgcagaagtt   1080
tgactactgg ggccagggaa ccctggtcac cgtctcgagc ggtggaggcg gttcaggcgg   1140
aggtggcagc ggcggtggcg ggtcgacgga catccagatg acccagtctc catcctccct   1200
gtctgcatct gtaggagaca gagtcaccat cacttgccgg gcaagtcaga gcattagcag   1260
ctatttaaat tggtatcagc agaaaccagg gaaagcccct aagctcctga tctatgctgc   1320
atccagtttg caaagtgggg tcccatcaag gttcagtggc agtggatctg ggacagattt   1380
cactctcacc atcagcagtc tgcaacctga agattttgca acttactact gtcaacagag   1440
ttacagtacc cctaatacgt tcggccaagg gaccaaggtg gaaatcaaac gggcggccgc   1500
acacaaccat cgccacaagc acctcgagct gttcctttt acctcagccc tccaactgag   1560
cggccttgta acgttcttca cgctaccgg aaggaacatc acgttattcg cgcccagtga   1620
tcaggttggt gcttgtacgt agctggaggg cttctgatta tcaactcccc tcgaaccctc   1680
cactgacccc aacctacgac ctcacaccca tacgcggccc accgaaggcg ctactagcgg   1740
cgctgccggc cctgaacctg aatcagtccc agctggtgac taacgcagtg ctcatgcgc   1800
cagtgctcat gtaccacgct ttcgtgccag cgaccaacaa cgcctctgtc cctcccggaa   1860
tttcgtacta caacgcgttg aagtgaggcg ggggcgcgag tttagaaggt tgacctggat   1920
gcggccacac ggctcgcatt gcagccttt catgtttgtg agtacctcaa tgttaggcca   1980
aaaaccgcgc caacgtgcca acctacagca cggatggcag cgtcagcggc aaccagctgg   2040
cgattacgag gacggtgtcg ggcggtctgc gggtcacctc catcggcagc gacgccaacg   2100
tgatcaaggt ggaccttccc aactccgggt gagagagcgc gtggctggcg gcgccaatgc   2160
gctggctcct ttcgcctatg tcaggatgag tgtcgtttcg ttgcggactg gatcgggtcg   2220
cggtgcatgg ggaagcggca cccggtagaa cgtgtatggg caagtggatg ggtacccgaa   2280
cagtctgcct ccgcgcgtca cacctcaact atctcctcta gacatgtggc attgtattgt   2340
cgctgacaac aggtccacgg tagtgcacgt cgtggacgcg gtgcttctcc cgttctaccc   2400
gtcagtgtac tccgtgagtt gcagtgcaag tgcgggcgca ggcgcaagct gcagaaacca   2460
aaccgggcaa ggcgcatgct cggctcctgc agccaaccat atggcgcaga cctgcctttc   2520
gcagcgccga cctacatgag gcagcgaccc aacacgttgc ccaaccctg cgcctgcacg   2580
tgcgccatgc aggctgtggc gcgcacctct gccctgagca cgctggccgc gctggtcggc   2640
tctgccagcg ccagcctggt gtccaagctg caggtgcgtg tgtgtgttga gcgggtggtg   2700
aagatttggt gggcgggctg gcacgccgc cgttcttggg ttacggcaag tgccgtgttt   2760
tgctgactgg cggcggagtt gtgcgcgtgc tcgcgcctct ctggcgcatc acagcgcccc   2820
tgatggtgtg cactgaagtg gcgattgcgt tccgtcctgg gcatgttcta caggacacta   2880
cgggtgtcta caccgtcttt gctccctaca atgcgtgagt tgtggttcag cacccactgg   2940
ttgtgccagg ccgacaggcc gacgttgcgt caagtcgcga accgtgcgcg gctgcaagca   3000
ttgccctgac cggctttgga ttgcccagcg gctcctacgc tgaccttccc tcgctgtggc   3060
```

| | |
|---|---:|
| tccctccctc gtgtgcacag cgccttcacg gccgccctgg ccccctccgg cctcaacacg | 3120 |
| acgattgcgc agctggcggc gcagcccgcc ctgctgcagt ccatcctgtc gtaccacgtc | 3180 |
| gtgcccggcc tgtacaacgc ctcctcgttt tccaccacac ccatcaccgt caccaccctg | 3240 |
| acgtatggct tcgctgcatg catgcgcacc cagcgtgtgt gcgccaccgt gcagaggcag | 3300 |
| gcctcaacct tcagatcagt ctgatcagtt tgaccagttg cattccgaca cacgacgatg | 3360 |
| ccctggcatg cctcaatgcc ccgctccgca gtggccagaa gctgacgctg gtgaaggacg | 3420 |
| gcacttcgct gtcggtgaag acggccgacg gcatgacggc caacctgctg caggcgcgcg | 3480 |
| acctgccgtg cggcttcacg gaccagtgag ttggtcgcgc gagtgaccag catagcacgg | 3540 |
| gacaaggact cgtggcatcc cgttgttcag gatgggtttg caccggcgta ggagccccaa | 3600 |
| atcccaacat gcacagctaa cgcatttcac actacacgtc caacctgtca ggggcacgtt | 3660 |
| ccgcgcgacc gtgcacgtga tcgacaaggt actcgtccct ccccctgtta cctccgtggc | 3720 |
| tgcggcgctg gccctgcgca ccgacgtcaa cacactgctg gcggccgtca aggcggaggg | 3780 |
| gtcctactcg gctgcgatca acaggtgact tgcggcaacc ggcgccgtta caaacgctat | 3840 |
| gcgcttactg ccgcttctcg ggcacatact gcgtccattt gactgcatta cgaaggactg | 3900 |
| gacttacccc agaattgttc ccctgcctgt gctgcatgcc ctgaaaccct cagcaccaca | 3960 |
| ttcaccggca cgcttctggc gcccatcgac tcggccttca cggcgctgct ggcggccaat | 4020 |
| ggcagcatca gcgccgcgca gctgctgggc aacaccacgg cgctgaagaa gatcctggac | 4080 |
| gtgagtgctc gtgctatgca ggcgtcctca ggccacagac ctctatgtac agccagcgtg | 4140 |
| cctgaccttg tggtgcttct ggctgtgttc aggcgcacgt ggtcacgggg tcggtgctga | 4200 |
| cggtggcggg tctcaccaac ggccagaaca ttaccaccag gtgggggcat tagccattgg | 4260 |
| gcttgaggtg tcccccacat tgggtggttg ccgctgcggc ttttggtcat tatgctgagt | 4320 |
| agaatgctat gctcttggct tgatctttgc gttgcatcat gtatcctgtt cgcagtggcg | 4380 |
| gcgctacgat cacggttgtc aagaccggaa ccacgaccca gctgaagctg gcaacagcg | 4440 |
| tggtcagcgt ggtcggggcg gaggttgcga ttggcagcag gtgggtgcac ctgacctctt | 4500 |
| cattgccacc ttcctgcagc gctgatgatg gcttctttgc gacgttatcg acgtgcttaa | 4560 |
| aaacgcaaca caacaagtgc catcgccgcg agcctgcatg ctgtgttatg gtgtcaacgc | 4620 |
| gccccatacc ccatgccatg ccccctggtg tttgcagcgc gacgctcatc gtcatcgacg | 4680 |
| gtgtcctggt gccgtccggc gtttccaccg tgacctcggg aggcggtggc ggcgccgcag | 4740 |
| cggcaactac gccgtccttc gtgctcatgc tgtggagcgt tgtggcggca gcgctgctgc | 4800 |
| tagcattcca gcgcctgcag tag | 4823 |

<210> SEQ ID NO 15
<211> LENGTH: 9392
<212> TYPE: DNA
<213> ORGANISM: Artificial Sequence
<220> FEATURE:
<223> OTHER INFORMATION: Nit-2A-H. pomatia lectin fusion

<400> SEQUENCE: 15

| | |
|---|---:|
| tctagatatg cacgccaggc ttgcggttga aggggcatca ggctcgaggc gagacgtcga | 60 |
| gggcgtgggc tctgtatggc tgggtaacgg tacgtataat tccaggtaca agctagagca | 120 |
| gacggtggtg agaagcatta gaagcattgt cccgagtgtg gtggctagaa tcccggccca | 180 |
| cgaatcacag tgaatgggta catgtacagg tgccccgcca gccccgctc ctctgctgcc | 240 |
| tctgatgcct catgccaaaa gtcctgacgc ggcgccctca catccccgtc cgggtaatct | 300 |

-continued

```
atgagtttcc cttatcgagc atgtacgcga tagtggacgg ggctcagggt gggggggtggg    360 tgggtgggag gggcgttcct tcagacaccc tggaggggtg gctagaaaag cggccgcgcg    420
ccagaaatgt ctcgctgccc tgtgcaataa gcaccggcta tattgctcag cgctgttcgg    480
cgcaacgggg ggtcagccct tgggaagcgt tggactatat ggtagggtgc gagtgacccc    540
gcgcgacttg gagctcgatg gccccgggtt gtttggggcg tccgcctctc gcgctattct    600
gagctggaga ccgaggcgca tgaaaatgca ttcgcttcca taggacgctg cattgtggct    660
tgaaggttca agggaagggt tcaaacgacc ccgccgtacg aacttttgtc ggggggcgct    720
cccggccccg ggtcttgtg cgcgcattag ggcttcgggt cgcaagcaag acgatacagg    780
aaccgaccaa tcgatagtct tgtgcgaccg tgcacgtgtg cagcaatagt taggtcgata    840
accacgttga acttgcgtct ctcttcgtgg cgcctcctgc ttggtgctcc acttcacttg    900
tcgctatata gcacagcgtt gaaagcaaag gccacactaa tacagccggg ctcgagagtc    960
cgtctgcgtt tgcattgttg gccaagggct gctttgtagc caaagccata cacgaagctt    1020
cacttgatta gctttacgac cctcagccga atcctgccag tatgaccgtt gccgagcagc    1080
ccgtggcact cgtgcccagc ggcaaggtgc aggcgcccga cgctatcgta tcgcaagcgg    1140
tcgagctcgg cgctccgtat gagcctccgc tctcgcccga ggatgccgac tggtcgcagc    1200
acgttcttcc ctcagctgtg gacaagcgcg accaggacac gcccgacaac tgggtgcggc    1260 gcgaccccg catcctgcgc ctcaccggcc ggcacccgct caactgcgag ccgcccatgt    1320
ccgtgctcat gcaggtgagg gggatttgca gggggggaggc gagcttgagg ttaggttagt    1380
gaacaaagag cagaggaggg aactgacagc catggctcga agctggctgg gttgataatt    1440
tagggagaat tatgcggcgg tggttgggcg tggggtgggg gtggcacggg tttgaggcct    1500
ggggcctggg gcgagggggcg gggttaacgg gtgacggcag gctgggcgta cgtggagacg    1560
cgtcaaccca cagtccagct acagcctcgt cctcactgac catctcccgc tctcctcttc    1620
ccctccaatc ccccaaacca accaaccctat cacaaaccaa cagtacggtt tcatcacgcc    1680
gccggccgta cacttcgtgc gcaaccacg cgccgcgccg cgcatccgct gggatgagca    1740
ccgcatcgag atcaacggcc tggtcaacaa gccgttgact ttgaccatgg acgagctggt    1800
ggcgctgccc tccgtcacct tcccggtgac gctggtgtgc gctggcaacc gccgcaagga    1860
ggagaacatg ctgaagaaga gcattggctt caactgggc ccttgtgcca ccagcaccac    1920
ctactggacg ggcgtgcggc tgcgcgacct gttgcagcac gccggcatca aggtgtgtgt    1980
gtgtgtgtgt gtatagctga cagggggttg taaataccag cccaaactaa accaaaccag    2040 tggggggtg aatgggtgat gtgcccgagc ccaataagtc ccaagagtca aggagtcgtc    2100
acccaaccca gaaatgcagc gcgagctccg cgtataaccg tgggaagagg ggggaacgag    2160
agagggacga gggatgggga gggatggcag ggagggatgg gagggaagga aggaggggag    2220
gagggaagca gagcgcgtgt ggtggtgatg cggggggcga ggaattgcaa gacagggct    2280 tgatgtggcg tggtgtgagt gcatgtatgc ctgtgtggga acgcaagcac atttccctga    2340
tccccgccac ccgccttgct tctccccatt cccacgcctg ctgctgcaga cgccggccga    2400
gggcgcccgc ttcgtgtgct tccgcggccc caagggcgag ctgccacgtg gcgaggacgg    2460
ctcgtacggc acctctctga cgtacgccaa ggccatggac cccgcctcgg acgttatcat    2520
cgcatacaag cagaaccaca ggtgtgtgcg tgtgcgtatg tgtgtgtgtg tgtgtgtgtg    2580
tgtgtgtgtg tgtctctgtg tgtgcgtgtg tgaaagagcg aaaggcaaag aataggctgt    2640
```

```
gcgtgtgcgt gtgtgttcga gcgcacaagg caaacactag gctgtgtgtg tttgtgtgcg    2700
cgtgtgtcgg ggggcggggg cgcggggagg gcagcgggag gttggcgcta ggctgggcac    2760
tgggtcgcac gggtcggagg cctggagctc gtccgaatgg cgatggcgac ggatgcgcaa    2820
gattgccgca cagaatagcc gtcgtgccgt gctgctcagc ttcctcaccc cctccctccc    2880
tccctccccg ctcctccccg cccctccccg cctgctgcct gctgcctgcg caggtggctg    2940
acgcccgacc acggcttccc ggtgcgcatc atcatcccgg gcttcatcgg cggccgcatg    3000
gtcaagtggc tgagcgagat caccgtcatg gacacggagt cgcaggtgcg tgggcgtgtg    3060
ggtttcgaga atgcttttaa ggctaacaat gcgaagccat caagccagcg agcacaacgt    3120
gtgtgtatgt agttgtctgg gtgtgtgcgg gcgaattgat tcaggccgat gggctggcat    3180
gtagctccca gcctggcatc aaagcttgtg gggcgtaact atgcttacac gcttcggccc    3240
taccacgata cccttgtaac ctgtgccgcc actccctctc catccccccc ccaaaacaca    3300 caccccctaca cacacagaac ttctaccact tcatggacaa ccgcgtgctg cccagccacg    3360
tggacgagga gctggccaag aaggagggtg agcgcggggg ggaggaccgt ggcgtgtgtg    3420
tattggagag cacagggtag gaaacaggga aagatttccg cagaaatctt gtgtgtgtgc    3480
atgtgaccgc catcattcga acccgtgtca tccccgttcc gaagtccccg tcctgaaact    3540
cgccgtgtac acgcgcgcag gctggtggta caagcccgag ttcatcatca acgacctcaa    3600
catcaacagc gcgatggctc ggccctggca cgacgagctg gtcccgctgg acgccaaccg    3660
gccctacacc atcaagggtt acgcctacgc cggtgagcag caacaacagc gataatgaca    3720
gcaagcgggg gcagcgagct gcctagcgag cgagtgagag agccaacgtc gttggtttcg    3780
ggccgtttgg tcgtggcact ggcaggcatc ataccgtaca tgcgatttag gacgtgtgga    3840
acgggacacg tgtgagcggc tagttaagta acggcaggac tgaagatgag gatgacgaag    3900
tatatttaag ttatttgctg gcgttggtct gtgtcgtcat cctcatcatg tgcaggcggc    3960
ggccgcaaga tcatccgctg cgaggtctcg ctggacgacg gcaagacctg gcgcctgggc    4020
gacatccagc gcttcgagga gcccaacgag tacggcaagc actggtgctg ggtgcactgg    4080
acgctggagg tgaggcgccg gagcgaggag gagtgggcgc ctgtgggcga aatgggcgat    4140
gtcggttggg atggcgggat gggccttttgc gtccctccag ccccacggac ccactgcttc    4200
gctctgcccc ccccccaaa aaaacacagg tgaacacgtt tgacttcctg tccgccaagg    4260
aggtgctgtg ccgcgcctgg gatgagacca tgaacacgca gccggcggtg atcacctgga    4320
acctgatggg catgatgaac aactgctact tccggtgagc gtgtgtgtgt gcgtgtgtgg    4380
aaggggggga ggcggcgatg agggaggcgg cgagaggcgc ccttttgtgc aatgttcagc    4440
atcgcagcgc cgctcatcgc atttcccga cacctgcgt gacagccctg gttccacacg    4500
tcggcccgcc cctccccacc ccatcccact aaactaatca tgaatgtccc ccacgtaaca    4560
cgcgcagcat caagatccac ccggaggtgg acccagccac gggcgtcatg ggcctgcgct    4620
tccagcaccc ggccccgtg gagctggcg acaagggcaa catgggctgg cgcgaggagg    4680
acaacctggt ggcgcaggcc gtggcggcgg cgcgcgacgg cggaggcgcg gcggcggcac    4740
cgccgccgcc gcctccggcg gcgctgctgg cgaatggcgg ccccaagcag tacacgctgg    4800
aggaggtggc ggagcacgcg agcgaggaga gctgctggtt cgtgcacgag ggccgggtga    4860
ggagagcgga tggcgtggtg gctggtctgg tggctggtct ggggctaggg gtttgtggtt    4920
gaggttgtag gaagggcgag aggcgtggtt gtgggtacgt gcgtgcccag cagctgcacc    4980
ccaacccgtg ctgacgtgca cacgaaaccc tgaaccaccc tggaccccag ctttctaacc    5040
```

```
cctttcaccc cccccccctcc ccgccctccg ctccctctcc aggtgtacga cgccacgccc   5100
tacctgaatg accaaccggg tggcgccgag tccatcctga tcactgcggg cgcggacgcc   5160
acagacgagt tcaacgccat ccacaggtgg gtagggggcg agaacgtgtg tgtgcatgtg   5220
ttttgtgcgt gtgtgattgg tgttttgggg gcgtgtacga gagaggggac gttttgcggg   5280
gctaggatca gcggcaggcg tgtataaggg gtccgcgcat ggcgtggcat ccaacccacc   5340
gtcccataca caccacgcac accaccgtcc ccatcccatc tcaccccatc tccccacctg   5400
cgcccccaca tccccacac acagctccaa agccaaggcc atgctggccc agtactacat   5460
cggtgacctc gtggcatcaa aaccagcaac cgccaacggc acggcaaccg ccaacggcaa   5520
cggcacggca actgccaacg gcaccgcggc ggcggcgccg cccgccgacc ctctggttgt   5580
gctgacgggt cgcgccaagg tgaagctacc gctggtggag cggattgagc tcaaccgcaa   5640
cacgcgcata ttccggttcg gcctgccctc gccggagcac cgcatcggtg ggtggtgtcg   5700
cgcgcgttat gatactaatg atacggtagt acgcacgtct tggctgccct gctgagtgtg   5760
tgccttgatt tgtgtggggg aagggggcaa gaacaagagc agccagcaga aggggaagga   5820
gcgggctgac ttcgtgtcgg ttgcgcgtcc gcggcaccac tcactggcca ccactcactg   5880
cacctcccac cccctccct ccccgatgc gcaggcctgc cggtgggcaa gcacgtgttc   5940
gtgtacgcgc aggtgggcgg cgagaacgtg atgcgcgcct acgccat cagcggggac   6000 gaggagaagg gccggctgga catgctcatc aaggtgcgtg tatgtgtgtg tgtgtatgtg   6060
tgagggacgt gtgtgcgcct gtgtgtgggg gtggggacgt gtgtgcatgt gtgtgtaggt   6120
gttttctggt gcgtcattca tcttttgtac cgtgtgtgcc ccctgaccgc gccatgcccc   6180
acaccccaca atccccacct gaccccacac accgggcgag cacgcgtcct accccgaggg   6240
cggcaagatg agccagcatt tcgactcgct cgccatcggc gactgcctgg agttcaaggg   6300
gccgctgggg cacttcgtgt acaacggccg cggaagctac acgctcaacg gcaaggtgcg   6360
cgcaacagga acgggcggtc ctgtagccgc gagaatgagt aagcctacca cacaagcaca   6420
tttaaatgca cacacattgt ggtgagcttc ttacggcaca ttgtcacaca cgctagatag   6480
ctaacacaca cacaccccta cctccctgca ggtgaccaag cacgccagtc acatgtcgtt   6540
tgttgcgggc ggcacgggca tcacgccctg ctacgcggtc atcaaggccg cactgcgcga   6600
ccccgaggac aacaccaagt gagcagcggc ggcggcgggg ggaagcggga gaggaagcgg   6660
cctcattgcc gttggctgtt agctgactga tgacacgctt tgctgccgcc gtatcacagt   6720
gccatagcat agcaaggcag tggatgggca ttggctacag ccagggacta aagggccaca   6780
cgcacgtccc cggcacatac acccgcgccc acacctgtgt ccatcatcca tcacgcacac   6840
ccactctgac accaacacac caacacacac acccccacaac cccttcccca cctgcaggct   6900
ggcgctgctg ttcgccaaca cacgaggc cgacattctg ctgcgcgagg agctggacga   6960
gctcgcaaac aaccccccg agcgcttccg gctgtggtga gcggcgcacc cggggggccac   7020 acgtacggcg cgcgcagccg cagctttggc ttcgccttcc gtcccagcct gagccaaccg   7080
tcaacgaacc aaccaacacc gaaccccctcc cccaccccct cccgccatcc tcaggtacac   7140
ggtgtcacag cccaaggacg cggcgacctg gaagtacgac gtggggcgtg tgagcaagga   7200
catgttcacg gagcacctct tcgccagcac gggcgaggac tgcctcagcc tcatgtgcgg   7260
gccgcacggc atgatcgagc actgctgcgt gccgttcctg gaggccatgg gctacagcaa   7320
ggaccgccag atccagttcg ccccggtgaa gcagaccctg aacttcgacc tgctgaagct   7380
```

```
ggcgggcgac gtggagagca acccgggccc cctcgagcag tgcgccctga agaccattgc    7440
tttcagcgcc gccatcgacc gcgagcagac gtttgacgcc aaccaggtgg tcatctacga    7500
catcgtgatt acgaaccacg gcaacgccta cgataactcc accggcctgt tcaccgcgcc    7560
ggtggacggc atgtacagct ttcaactgaa cctgctcacg attaaggaga aggagggctg    7620
gctggagctc gtgcacaacg tcagctcaa ggtgagcgtc tacgcgaagc aggacagcac     7680
gtacgattcg tcgagcaact cggtcatcat caagatgaag gagggtgatc gggtgaacgt    7740
gcgggcccac aagaagtcgg gtctgttcgg ccgcgacgac gagctgtaca acacgttctc    7800
cggccacttc ctgtccggcc tgggcaccgg caccggtgac tacaaggacg acgacgacaa    7860
gtccggcgag aacctgtact ccagggcca aaccaccgc cacaagcaca ccggtgtcga      7920
ctagggatct atcgctagag attgtggcca cggttggatc atgcgaccag caggattgga    7980
tccgaatcca ggcatctggg cggatgccag gcaggggca gggcagcgg tcgtgggagc      8040 gtgtgtgagc cggataaggg ctggcacagg ccacggccgc agcggccttt tgtgcagttt    8100
gacgacggaa gtgtgcgtct gtgtggttgt gtgtgagagc taggcaggac cgcagggtca    8160
gacagagtgc gcccggcttg gctgcggcgc actgggacgc gttggcagtt taaaacctgc    8220
gctgagggga caaacgagtt tggcaacagt aggcagttaa aagatagaat gtgtaggtca    8280
gtttcccagt gggcaaatga gttgtgcaag cctgcaaacg gcaggaagca tggcaaggat    8340
attactgatt gactgcagca ggggatagca gtagtggcac agcagagtgc ccgagagagt    8400
gtgtgcacgt gctagttttg gagtcaggca ccgccgttga gatgatgtat tgatgacgca    8460
gcatttcatg tgacataggg aggctttcca tgcggttatt atattatgtc aggaaagtgc    8520
ctgacagcgt ttagcgcgtg gggagaagta cgaccctccg tgggctgaac ccacgttagg    8580 gcgtggggttg gtcaggaggg tgggtgccat gcatgaagca gagggccggg gcgttagccc    8640
gttttggtga gagcttgttt gatgcaatgc gatacataat cataagggg ttttggcgcg     8700 tgagagtgcg acctgtgtat ggcagcacgc catcggtgcc aaccggcgaa ggtgcaggag    8760
gtgcaggtaa agctacatat agacaccccc tgccgcacag ttgtaaatta agcaagcgac    8820
ttgcattgtg tccatcactt tgtgcagcag ggcaggcaag gcaggtgct gccatgggct     8880 ggcacggcgt ggggcaacaa gggggcttag actcccaggg gcgaccagtc gagccagggc    8940
cgcaaggacc atgagagct gctagtgccc caggcggcc aggccgcaac agcagttggg      9000
cggccagatg gcagaccgcg aatgggagcc cttggctgta agtcgggctg cgagaggagt    9060
ttacctcgac tgtggccggg aagaggggc gctgggcaag agtcggacta gggagtgcgc     9120
gactgaaacg cgcggggcac tgcgcgggga cacaggcgcg gtcaaagcac ctgtgtacct    9180
cgcgagtaga tagcagttta gcgcatgtcc ttgataatgg tggagctctc agcgaccaaa    9240
gaagcgactt cagagcgacc ggcccactaa cggtcacacc cgaacggccg ctccctcgtt    9300
ttcggtcgca cagccgctat agaagtcgca agtagcaaac actaatgttg cttttacagc    9360
gacaagtgaa acgggttggt tgaagagaat tc                                  9392
```

<210> SEQ ID NO 16
<211> LENGTH: 1431
<212> TYPE: DNA
<213> ORGANISM: Artificial Sequence
<220> FEATURE:
<223> OTHER INFORMATION: LppOmpA-scFv5 fusion

<400> SEQUENCE: 16

```
atgacatgtg aattcatgaa agctactaaa ctggtactgg gcgcggtaat cctgggttct    60
```

```
actctgctgg caggttgctc cagcaacgct aaaatcgatc agggaattcc aggcaacccg    120
tatgttggct ttgaaatggg ttacgactgg ttaggtcgta tgccgtacaa aggcagcgtt    180
gaaaacggtg catacaaagc tcagggcgtt caactgaccg ctaaactggg ttacccaatc    240
actgacgacc tagacatcta cactcgtctg ggtggtatgg tatggcgtgc agacactaaa    300
tccaacgttt atggtaaaaa ccacgacacc ggcgtttctc cggtcttcgc tggcggtgtt    360
gagtacgcga tcactcctga aatcgctacc cgtctggaat accagtggac caacaacatc    420
ggtgacgcac acaccatcgg cactcgtccg gacaacggta ttaactcgag cagcgtgcct    480
ggcgatccgc gcgtgcctcg cagctggacg gagcccttc cgttctgcgg tacaggcgac     540
tacaaggatg atgacgacaa gtcgggcgag aacctctatt ccagggtca caaccaccgc    600 cacaagcacc ctaggatgaa atacctattg cctacggcag ccgctggatt gttattactc    660
gcggcccagc cggccatggc cgaggtgcag ctgttggagt ctgggggagg cttggtacag    720 cctgggggt ccctgagact ctcctgtgca gcctctggat tcacctttag cagctatgcc     780
atgagctggg tccgccaggc tccagggaag gggctggagt gggtctcatg gatttcgggg    840
actggttcgc ggacagacta cgcagactcc gtgaagggcc ggttcaccat ctccagagac    900
aattccaaga acacgctgta tctgcaaatg aacagcctga gagccgagga cacggccgta    960
tattactgtg cgaaaaaggc gcagaagttt gactactggg gccagggaac cctggtcacc   1020
gtctcgagcg gtggaggcgg ttcaggcgga ggtggcagcg gcggtggcgg gtcgacggac   1080
atccagatga cccagtctcc atcctccctg tctgcatctg taggagacag agtcaccatc   1140
acttgccggg caagtcagag cattagcagc tatttaaatt ggtatcagca gaaaccaggg   1200 aaagcccta agctcctgat ctatgctgca tccagttttgc aaagtggggt cccatcaagg   1260
ttcagtggca gtggatctgg gacagatttc actctcacca tcagcagtct gcaacctgaa   1320
gattttgcaa cttactactg tcaacagagt tacagtaccc ctaatacgtt cggccaaggg   1380
accaaggtgg aaatcaaacg ggcggccgca catcatcatc accatcacta a            1431
```